United States Patent
O'Malley et al.

(10) Patent No.: US 12,098,171 B2
(45) Date of Patent: Sep. 24, 2024

(54) HYBRID SUGAR TRANSPORTERS WITH ALTERED SUGAR TRANSPORT ACTIVITY AND USES THEREOF

(71) Applicant: The Regents of the University of California, Oakland, CA (US)

(72) Inventors: Michelle A. O'Malley, Santa Barbara, CA (US); Igor A. Podolsky, Goleta, CA (US); Susanna Seppala, Santa Barbara, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 40 days.

(21) Appl. No.: 17/548,410

(22) Filed: Dec. 10, 2021

(65) Prior Publication Data
US 2023/0002454 A1 Jan. 5, 2023

Related U.S. Application Data

(60) Provisional application No. 63/124,662, filed on Dec. 11, 2020.

(51) Int. Cl.
C07K 14/37 (2006.01)

(52) U.S. Cl.
CPC .......... *C07K 14/37* (2013.01); *C07K 2319/03* (2013.01)

(58) Field of Classification Search
None
See application file for complete search history.

(56) References Cited

U.S. PATENT DOCUMENTS

| | | |
|---|---|---|
| 7,985,567 B2 | 7/2011 | Chou et al. |
| 8,420,833 B2 | 4/2013 | Katz et al. |
| 8,852,902 B2 | 10/2014 | Katz et al. |
| 9,109,175 B2 | 8/2015 | Lee et al. |
| 9,200,298 B2 | 12/2015 | Lee et al. |
| 9,334,514 B2 | 5/2016 | Fortman et al. |
| 9,376,691 B2 | 6/2016 | Peralta-Yahya et al. |
| 9,382,553 B2 | 7/2016 | Kirby et al. |
| 9,631,210 B2 | 4/2017 | Chou et al. |
| 9,951,345 B2 | 4/2018 | Steen et al. |
| 10,167,488 B2 | 1/2019 | Keasling et al. |
| 2004/0058429 A1* | 3/2004 | Bill ............... C12N 15/81 426/11 |

FOREIGN PATENT DOCUMENTS

| | | |
|---|---|---|
| WO | 2009006386 A2 | 1/2009 |
| WO | 2009006429 A1 | 1/2009 |
| WO | 2009006430 A1 | 1/2009 |
| WO | 2009134899 A2 | 11/2009 |
| WO | 2010127318 A2 | 11/2010 |
| WO | 2012050931 A2 | 4/2012 |
| WO | 2012058686 A2 | 5/2012 |
| WO | 2012064740 A1 | 5/2012 |
| WO | 2012071439 A1 | 5/2012 |
| WO | 2012135389 A2 | 10/2012 |
| WO | 2014093402 A2 | 6/2014 |
| WO | 2015013674 A2 | 1/2015 |
| WO | 2017214159 A1 | 12/2017 |
| WO | 2018200888 A1 | 11/2018 |
| WO | 2019050990 A1 | 3/2019 |

OTHER PUBLICATIONS

Nijland, J.G., et al. 2014 Biotechnology for Biofuels 7:168, 11 pages. (Year: 2014).*
Chang et al., "Phylogenomic analysis indicate that early fungi evolveddifesting cell walls of algal ancestors of land plants", Genome Biol. Evol. 7(6)1590-1601 (2015).
Joneson et al., "Genomic Transition to Pathogenicity in Chytrid Fungi", PloS Pathog. 7(11), e1002338 (2011).
Kijpornyongpan et al., "Broad Genomic Sampling Reveals a Smut Pathogenic Ancestry of the Fungal Clade Ustilaginomycotina", Mol. Biol. Evol.35(8): 1840-1854 (2018).
Sharma et al., "Xylose transport in yeast for lignocellulosic ethanol production: Current status." J. Biosci. Bioeng. 125(3):259-67 (2018).
Lian et al., "Directed evolution of a cellodextrin transporter for improved biofuel production under anaerobic conditions in *Saccharomyces cerevisiae*." Biotechnol. Bioeng. 111(8):1521-31 (2014).
Gárdonyi et al., "Control of xylose consumption by xylose transport in recombinant *Saccharomyces cerevisiae*." Biotechnol. Bioeng. 82(7):818-24 (2003).
Kim et al., "Simultaneous co-fermentation of mixed sugars: a promising strategy for producing cellulosic ethanol." Trends Biotechnol. 30(5):274-82 (2012).
Jeffries, "Utilization of xylose by bacteria, yeasts, and fungi". In Pentoses and Lignin, pp. 1-32. Berlin/Heidelberg: Springer-Verlag (1983).
Eliasson et al., "Anaerobic xylose fermentation by recombinant *Saccharomyces cerevisiae* carrying XYL1, XYL2, and XKS1 in mineral medium chemostat cultures." Appl. Environ. Microbiol. 66(8):3381-86 (2000).
Kim et al., "Combinatorial design of a highly efficient xylose-utilizing pathway in *Saccharomyces cerevisiae* for the production of cellulosic biofuels." Appl. Environ. Microbiol. 79(3):931-41 (2013).
Shen et al., "An efficient xylose-fermenting recombinant *Saccharomyces cerevisiae* strain obtained through adaptive evolution and its global transcription profile." Appl. Microbiol. Biotechnol. 96(4):1079-91 (2012).

(Continued)

*Primary Examiner* — Marsha Tsay
(74) *Attorney, Agent, or Firm* — Robin C. Chiang; LAWRENCE BERKELEY NATIONAL LABORATORY

(57) ABSTRACT

The present invention provides for a hybrid sugar transporter having an altered sugar transporter activity and comprising at least a first transmembrane domain (TMD) from a first sugar transporter and a second TMD from a second sugar transporter, wherein the first sugar transporter and the second sugar transporter are heterologous to each other.

15 Claims, 19 Drawing Sheets

Specification includes a Sequence Listing.

(56) References Cited

OTHER PUBLICATIONS

Young et al., "Functional survey for heterologous sugar transport proteins, using *Saccharomyces cerevisiae* as a host." Appl. Environ. Microbiol. 77(10):3311-19 (2011).
Moysés et al., "Xylose Fermentation by *Saccharomyces cerevisiae*: Challenges and Prospects." Int. J. Mol. Sci. 17(3):207 (2016).
Hou et al., "Engineering of *Saccharomyces cerevisiae* for the efficient co-utilization of glucose and xylose." FEMS Yeast Res. 17(4) (2017), 11 pages.
Seppälä et al., "Mapping the membrane proteome of anaerobic gut fungi identifies a wealth of carbohydrate binding proteins and transporters." Microb. Cell Fact. 15(1):212 (2016).
Seppälä S, Yoo JI, Yur D, O'Malley MA. 2019. Heterologous transporters from anaerobic fungi bolster fluoride tolerance in *Saccharomyces cerevisiae*. Metab. Eng. Commun. 9:e00091 (2019).
Yoo et al., "Engineered fluoride sensitivity enables biocontainment and selection of genetically-modified yeasts." Nat. Commun. 11:5459 (2020), 9 pages.
Flint, "The rumen microbial ecosystem—some recent developments." Trends Microbiol. 5(12):483-88 (1997).
Theodorou et al., Anaerobic fungi in the digestive tract of mammalian herbivores and their potential for exploitation. Proc. Nutr. Soc. 55(03):913-926 (1996).
Henske et al., "Biomass-degrading Enzymes are Catabolite Repressed in Anaerobic Gut Fungi." AIChE J. 64(12)4263-4270 (2018).
Jeena et al., "Structure, evolution and diverse physiological roles of SWEET sugar transporters in plants", Structure, evolution and diverse physiological roles of SWEET sugar transporters in plants. Plant Mol. Biol. 100(4-5):351-65 (2019).
Solomon et al., "Early-branching gut fungi possess a large, comprehensive array of biomass-degrading enzymes." Science, 351(6278):1192-1196 (2016).
El-Gebali et al., "The Pfam protein families database in 2019", Nucleic Acids Res. 47:D427-D432 (2018).
Finn et al., "HMMER web server: interactive sequence similarity searching", Nucleic Acids Research, 39: W29-W37 (2011).
Chen et al., "Sugar transporters for intercellular exchange and nutrition of pathogens." Nature. 468(7323):527-532 (2010).
Grigoriev et al., "MycoCosm portal: gearing up for 1000 fungal genomes", Nucleic Acids Res. 42 (Database issue): D699-704 (2014).
Tsirigos et al., "The TOPCONS web server for consensus prediction of membrane protein topology and signal peptides", Nucleic Acids Res. 43(W1):W401-407 (2015).
Fu et al., "CD-HIT: Accelerated for clustering the next-generation sequencing data." Bioinformatics. 28(23):3150-3152 (2012).
Sievers et al., "Fast, scalable generation of high-quality protein multiple sequence alignments using Clustal Omega", Mol. Syst. Biol. 7(1):539 (2014), 6 pages.
Stamatakis, "RAxML version 8: a tool for phylogenetic analysis and post-analysis of large phylogenies", Bioinformatics. 30(9):1312-1313 (2014).
Miller et al., "Creating the CIPRES Science Gateway for inference of large phylogenetic trees" IEEE, (2010).
Kumar et al., "MEGA7: Molecular Evolutionary Genetics Analysis Version 7.0 for Bigger Datasets." Mol. Biol. Evol. 33(7):1870-74 (2016).
Jia et al., "Integrative View of the Diversity and Evolution of SWEET and SemiSWEET Sugar Transporters. Front", Plant Sci. 8:2178 (2017).

Wieczorke et al., "Concurrent knock-out of at least 20 transporter genes is required to block uptake of hexoses in *Saccharomyces cerevisiae*." FEBS Lett. 464(3):123-28 (1999).
Kim et al., "Rational and Evolutionary Engineering Approaches Uncover a Small Set of Genetic Changes Efficient for Rapid Xylose Fermentation in *Saccharomyces cerevisiae*", PLoS One. 8(2):e57048 (2013).
Xu, "Engineering *Saccharomyces cerevisiae* for Cellulosic Ethanol Production." University of Illinois at Urbana—Champaign. 1-87 pp (2015).
Reider et al., "Evolved hexose transporter enhances xylose uptake and glucose/xylose co-utilization in *Saccharomyces cerevisiae*", Sci. Rep. 6(1):19512 (2016).
Gietz et al., "Transformation of yeast by lithium acetate/single-stranded carrier DNA/polyethylene glycol method" Methods Enzymol. 350:87-96 (2002).
Nørholm, "A mutant Pfu DNA polymerase designed for advanced uracil-excision DNA engineering", BMC Biotechnol. 10(1):21 (2010), 7 pages.
Cavaleiro et al., "Accurate DNA Assembly and Genome Engineering with Optimized Uracil Excision Cloning", ACS Synth. Biol. 4(9):1042-1046 (2015).
Sikorski et al., "A system of shuttle vectors and yeast host strains designed for efficient manipulation of DNA in *Saccharomyese cervisae*", Genetics, 122: 19-27 (1999).
Henske et al., "Transcriptomic characterization of Caecomyces churrovis: A novel, non-rhizoid-forming lignocellulolytic anaerobic fungus." Biotechnol. Biofuels. 10(1) (2017), 12 pages.
Hu et al., Phylogenetic evidence for a fusion of archaeal and bacterial SemiSWEETs to form eukaryotic SWEETs and Identification of SWEET hexose transporters in the amphibian chytrid pathogen Batrachochytrium dendrobatidis. FASEB J. (2016).
Tao et al., Structure of a eukaryotic SWEET transporter in a homotrimeric complex. Nature. 527(7577):259-263 (2015).
Han et al., "Molecular mechanism of substrate recognition and transport by the AtSWEET13 sugar transporter", Proc. Natl. Acad. Sci. U. S. A. 114(38):10089-10094 (2017).
Xuan et al., "Functional role of oligomerization for bacterial and plant SWEET sugar transporter family", Proc. Natl. Acad. Sci. U. S. A. 110(39): E3685-94 (2013).
Chorev et al., "The Function of Introns", Front. Genet. 3:55 (2012), 15 pages.
Haitjema et al., "A parts list for fungal cellulosomes revealed by comparative genomics", Nat. Microbiol. 2(8):17087, (2017), 8 pages.
Wallin et al., "Genome-wide analysis of integral membrane proteins from eubacterial, archaean, and eukaryotic organisms" Protein Sci. 7(4):1029-1038 (1998).
Harley et al., "Transmembrane protein insertion orientation in yeast depends on the charge difference across transmembrane segments, their total hydrophobicity, and its distribution" J. Biol. Chem. 273(38):24963-71 (1998).
Hamacher et al., "Characterization of the xylose-transporting properties of yeast hexose transporters and their influence on xylose utilization" Microbiology. 148(9):2783-2788 (2002).
Mondo et al., "Widespread adenine N6-methylation of active genes in fungi", Nat. Genet, 49(6)964-968 (2017).
Ahrendt et al., "Leveraging single-cell genomics to expand the fungal tree of life", 3(12)1417-1428 (2018).

* cited by examiner

HYBRID SUGAR TRANSPORTERS WITH ALTERED SUGAR TRANSPORT ACTIVITY AND USES THEREOF

RELATED PATENT APPLICATIONS

This application claims priority to U.S. Provisional Patent Application Ser. No. 63/124,662, filed Dec. 11, 2020, which is hereby incorporated by reference.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of sugar transporters.

BACKGROUND OF THE INVENTION

Membrane-embedded transport proteins mediate the uptake and extrusion of diverse small molecules across the cellular membrane, facilitating a crucial first step in many metabolic pathways. Membrane-embedded transporter activity can therefore dictate the productivity of microbial production strains, as they govern carbon uptake by the cell (1-3). Accordingly, microbial fuel and chemical production from lignocellulosic biomass is constrained by poor sugar transport and utilization in established production strains (4). The yeast *Saccharomyces cerevisiae*, used extensively in biotechnological processes with D-glucose feeds, demonstrates poor fermentation of lignocellulosic hydrolysates, especially those that contain a substantial fraction of D-xylose (5-8). The poor performance of transport systems in *S. cerevisiae* limits efficient co-utilization of glucose and xylose, which is necessary for the economic fermentation of commodity chemicals such as bioethanol (9, 10). Engineering the known repertoire of native and heterologous transporters has improved strain performance, but further advances are necessary for application in industrial strains (11). Thus, it is valuable to also survey for transporters with novel or enhanced function in non-model organisms, particularly microbes that are naturally adept at lignocellulosic hydrolysate fermentation.

The recently characterized anaerobic gut fungi (Neocallimastigomycota), native to the digestive tract of large herbivores, possess a wealth of enzymes and transporter proteins that can be harnessed for numerous biotechnological applications (12-14). These early diverging fungi excel at deconstructing biomass using an array of carbohydrate-active enzymes (15). With remarkable efficiency, anaerobic gut fungi produce and utilize a variety of breakout sugars from raw lignocellulosic biomass in a highly competitive environment, including D-xylose (16, 17). Recent annotation of genomic and transcriptomic sequences for three unique gut fungal isolates revealed a large trove of putative sugar transporters (12), yet to date none have been evaluated to determine their functional activity. Most notable are members of the recently discovered Sugars Will Eventually be Exported Transporter (SWEET) superfamily that are abundant in plant genomes but absent in the majority of sequenced fungal genomes, including *S. cerevisiae* (12). Functional characterization of plant SWEETs has identified individual transporters with wide-ranging specificity and affinity towards a variety of mono- and di-saccharide sugars (18). Yet, the functional diversity of SWEETs within the fungal kingdom is poorly understood, and SWEETs have not yet been utilized for metabolic engineering.

SUMMARY OF THE INVENTION

The present invention provides for a hybrid sugar transporter having an altered sugar transporter activity and comprising at least a first transmembrane domain (TMD) from a first sugar transporter and a second TMD from a second sugar transporter, wherein the first sugar transporter and the second sugar transporter are heterologous to each other. In some embodiments, the hybrid sugar transporter comprises at least seven TMDs. In some embodiments, the altered sugar transporter activity is the increased or enhanced activity for transporting a sugar. In some embodiments, the increased or enhanced activity is for transporting a pentose, such as a xylose.

The present invention provides for an isolated, purified or purified sugar transporter having an amino acid sequence comprising at least 70%, 80%, 90%, 95%, or 99% identity with the amino acid sequence of *Neocallimastix californiae* SWEET1 (SEQ ID NO:1).

In some embodiments, the sugar transporter or hybrid sugar transporter comprises one or more of the conserved amino acids and amino acid sequences indicated in FIGS. 8, 9, and/or 16B, and/or Table 5. In some embodiments, the sugar transporter comprises any of the hybrid sugar transporters described herein. In some embodiments, the sugar transporter is an anaerobic gut fungi sugar transporter. In some embodiments, the sugar transporter is a *Neocallimastix californiae* (Nc), *Anaeromyces robustus* (Ar), or *Piromyces finnis* (N) sugar transporter.

In some embodiments, the hybrid sugar transporter comprises the following structure:

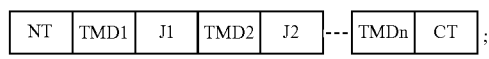

wherein each box represents an amino acid sequence, NT is a N-terminal domain, TMD1 is a first TMD, J1 is a first junction domain, the dotted line represents optionally further TMDx and Jx pairs (wherein x is an integer and is less than n), TMDn is the nth TMD (wherein n is an integer and is the maximum number of TMDs in the hybrid sugar transporter), and CT is a C-terminal domain. In embodiments, n is 5, 6, 7, 8, or 9. In some embodiments, NT is about 3, 4, 5, 6, 7, 8, 9, 10, 11, 12, 13, 14, 15, 16, 17, 18, 19, or 20 amino acid residues in length. In some embodiments, NT is about 4 to 12 amino acid residues in length. In some embodiments, a (or each) TMD is about 19, 20, 21, or 22 amino acid residues in length. In some embodiments, a (or each) J is about 3, 4, 5, 6, 7, 8, 9, 10, 11, 12, 13, 14, 15, 16, 17, 18, 19, 20, 21, 22, 23, 24 or 25 amino acid residues in length. In some embodiments, CT is about 10, 15, 20, 25, 30, 35, 40, 45, 50, 55, 60, 65, or 70 amino acid residues in length. In some embodiments, CT is about 28 to 42 amino acid residues in length.

In some embodiments, n is 7, NT is about 4 to 12 amino acid residues in length, each TMD is about 21 or 22 amino acid residues in length, each J is about 3 to 17 amino acid residues in length, and CT is about 28 to 42 amino acid residues in length. In some embodiments, each is independently a TMD of any TMS of a AGF SWEET, or any TMD of a AGF SWEET described herein, such as one described in FIGS. 8 and 9.

In some embodiments, each sugar transporter is a sugar transporter of a species listed in Table 4. In some embodiments, each sugar transporter is a sugar transporter listed in Table 4. In some embodiments, each TMD is a TMD from a sugar transporter listed in Table 4. In some embodiments, the hybrid sugar transporter comprises one or more conserved amino acid residues indicated in FIGS. 8 and/or 9, and/or Table 5. In some embodiments, any TMD has an amino acid sequence comprising at least 70%, 80%, 90%, 95%, or 99% identity with the amino acid sequence of any AGF SWEET described herein.

In some embodiments, the NT comprises amino acid sequence ECXSXXCEI (SEQ ID NO:2). In some embodiments, a TMD comprises amino acid sequence TETVFPLXGXFTXYFIFLSPF (SEQ ID NO:3), PSXMIXCNCLCXXLYSFVLH (SEQ ID NO:4), TFWPNXGGIXLGXYYXXIL (SEQ ID NO:5), ITLXXFTXLXIXGXALSFI (SEQ ID NO:6), KNXMGIXXIIXLCXXYVSPLT (SEQ ID NO:7), LXTXAXXXNGXXWLXYGXFF (SEQ ID NO:8), or WFPNGLGVXSALLQXXLXXI (SEQ ID NO:9). In some embodiments, TMD1 comprises SEQ ID NO:3. In some embodiments, TMD2 comprises SEQ ID NO:4. In some embodiments, TMD3 comprises SEQ ID NO:5. In some embodiments, TMD4 comprises SEQ ID NO:6. In some embodiments, TMD5 comprises SEQ ID NO:7. In some embodiments, TMD6 comprises SEQ ID NO:8. In some embodiments, TMD7 comprises SEQ ID NO:9. In some embodiments, a J comprises amino acid sequence KEXXXLXXXNXXCXINP (SEQ ID NO:10), NHW, SNXKPKDF (SEQ ID NO:12), KXNYXAA (SEQ ID NO:13), EVIKXKNSXSIN (SEQ ID NO:14), or NDF. In some embodiments, J1 comprises amino acid sequence KEXXXLXXXNXXCXINP (SEQ ID NO:10). In some embodiments, J2 comprises amino acid sequence NHW. In some embodiments, J3 comprises amino acid sequence SNXKPKDF (SEQ ID NO:12). In some embodiments, J4 comprises amino acid sequence KXNYXAA (SEQ ID NO:13). In some embodiments, J5 comprises amino acid sequence EVIKXKNSXSIN (SEQ ID NO:14). In some embodiments, J6 comprises amino acid sequence NDF. In some embodiments, CT comprises amino acid sequence KXXXEXXI (SEQ ID NO:16) and/or EXXSXXXAXXL (SEQ ID NO:17).

In some embodiments, the hybrid sugar transporter, or the isolated, purified or purified sugar transporter, comprises: an NT comprising amino acid sequence ECXSXXCEI (SEQ ID NO:2), a TMD1 comprising amino acid sequence TETVFPLXGXFTXYFIFLSPF (SEQ ID NO:3), a TMD2 comprising amino acid sequence PSXMIXCNCLCXXLYSFVLH (SEQ ID NO:4), a TMD3 comprising amino acid sequence TFWPNXGGIXLGXYYXXIL (SEQ ID NO:5), a TMD4 comprising amino acid sequence ITLXXFTXLXIXGXALSFI (SEQ ID NO:6), a TMD5 comprising amino acid sequence KNXMGIXXIIXLCXXYVSPLT (SEQ ID NO:7), a TMD6 comprising amino acid sequence LXTXAXXXNGXXWLXYGXFF (SEQ ID NO:8), a TMD7 comprising amino acid sequence WFPNGLGVXSALLQXXLXXI (SEQ ID NO:9), a J1 comprising amino acid sequence KEXXXLXXXNXXCXINP (SEQ ID NO:10), a J2 comprising amino acid sequence NHW (SEQ ID NO:10), a J3 comprising amino acid sequence SNXKPKDF (SEQ ID NO:12), a J4 comprising amino acid sequence KXNYXAA (SEQ ID NO:13), a J5 comprising amino acid sequence EVIKXKNSXSIN (SEQ ID NO:14), a J6 comprising amino acid sequence NDF, and/or a CT comprising amino acid sequence KXXXEXXI (SEQ ID NO:16) and/or EXXSXXXAXXL (SEQ ID NO:17).

In some embodiments, the hybrid sugar transport comprises the NT, TMD1, J1, TMD2, J2, TMD3, J3, TMD4, J4, TMD5, J5, TMD6, J6, and TMD7 of a first sugar transporter, and CT of a second sugar transporter. In some embodiments, the hybrid sugar transport comprises the NT, TMD1, J1, TMD2, J2, TMD3, J3, TMD4, J4, TMD5, J5, TMD6, and J6 of a first sugar transporter, and TMD7 and CT of a second sugar transporter. In some embodiments, the hybrid sugar transport comprises the NT, TMD1, J1, TMD2, J2, TMD3, J3, TMD4, J4, TMD5, J5, and TMD6 of a first sugar transporter, and J6, TMD7 and CT of a second sugar transporter. In some embodiments, the hybrid sugar transport comprises the NT, TMD1, J1, TMD2, J2, TMD3, J3, TMD4, J4, TMD5, and J5 of a first sugar transporter, and TMD6, J6, TMD7 and CT of a second sugar transporter. In some embodiments, the hybrid sugar transport comprises the NT, TMD1, J1, TMD2, J2, TMD3, J3, TMD4, J4, and TMD5 of a first sugar transporter, and J5, TMD6, J6, TMD7 and CT of a second sugar transporter. In some embodiments, the hybrid sugar transport comprises the NT, TMD1, J1, TMD2, J2, TMD3, J3, TMD4, and J4 of a first sugar transporter, and TMD5, J5, TMD6, J6, TMD7 and CT of a second sugar transporter. In some embodiments, the hybrid sugar transport comprises the NT, TMD1, J1, TMD2, J2, TMD3, J3, and TMD4 of a first sugar transporter, and J4, TMD5, J5, TMD6, J6, TMD7 and CT of a second sugar transporter. In some embodiments, the hybrid sugar transport comprises the NT, TMD1, J1, TMD2, J2, TMD3, and J3 of a first sugar transporter, and TMD4, J4, TMD5, J5, TMD6, J6, TMD7 and CT of a second sugar transporter. In some embodiments, the hybrid sugar transport comprises the NT, TMD1, J1, TMD2, J2, and TMD3 of a first sugar transporter, and J3, TMD4, J4, TMD5, J5, TMD6, J6, TMD7 and CT of a second sugar transporter. In some embodiments, the hybrid sugar transport comprises the NT, TMD1, J1, TMD2, and J2 of a first sugar transporter, and TMD3, J3, TMD4, J4, TMD5, J5, TMD6, J6, TMD7 and CT of a second sugar transporter. In some embodiments, the hybrid sugar transport comprises the NT, TMD1, J1, and TMD2 of a first sugar transporter, and J2, TMD3, J3, TMD4, J4, TMD5, J5, TMD6, J6, TMD7 and CT of a second sugar transporter. In some embodiments, the hybrid sugar transport comprises the NT, TMD1, and J1 of a first sugar transporter, and TMD2, J2, TMD3, J3, TMD4, J4, TMD5, J5, TMD6, J6, TMD7 and CT of a second sugar transporter. In some embodiments, the hybrid sugar transport comprises the NT and TMD1 of a first sugar transporter, and J1, TMD2, J2, TMD3, J3, TMD4, J4, TMD5, J5, TMD6, J6, TMD7 and CT of a second sugar transporter. In some embodiments, the hybrid sugar transport comprises the NT of a first sugar transporter, and TMD1, J1, TMD2, J2, TMD3, J3, TMD4, J4, TMD5, J5, TMD6, J6, TMD7 and CT of a second sugar transporter.

In some embodiments, the first or second sugar transporter is a sugar transport indicated in Table 4. In some embodiments, the first sugar transporter is NcSWEET1 or PfSWEET2. In some embodiments, the second sugar transporter is NcSWEET1 or PfSWEET2. In some embodiments, the first sugar transporter is NcSWEET1, and the second sugar transporter is PfSWEET1.

The present invention provides for a nucleic acid comprises an open reading frame (ORF) encoding the hybrid sugar transporter of the present invention, or the sugar transporter of the present invention, optionally operatively linked to a promoter heterologous to the hybrid sugar transporter or sugar transporter. In some embodiments, the ORF is codon optimized for a microbe. In some embodiments, the microbe is one described herein. In some embodiments, the ORF is codon optimized for expression in a *Saccharomyces* species. In some embodiments, the ORF is codon optimized for expression in *Saccharomyces cerevisae*. In some embodiments, the ORF comprises a nucleotide sequence of SEQ ID NO:1 or SEQ ID NO:18, or any one of SEQ ID NOs:21-28, or any TMG found within the ORF. In some embodiments, the nucleic acid is double- or single-stranded DNA or RNA.

The present invention provides for a vector comprising the nucleic acid of the present invention. In some embodiments, the ORF is operatively linked to a promoter capable of expressing the ORF, such as in an in vitro or in vivo system. In some embodiments, the vector comprises one or more nucleotides sequences which confers stable residence or replication in a microbe, such a microbe described herein. In some embodiments, the vector is an expression vector. In some embodiments, the vector and/or promoter is heterologous to the hybrid sugar transporter or sugar transporter.

The present invention provides for a host cell comprising the vector of the present invention. The host cell can be any microbe described herein. In some embodiments, the host cell is capable of expressing the hybrid sugar transporter or sugar transporter. In some embodiments, the host cell is capable of expressing the hybrid sugar transporter or sugar transporter, and the unmodified host cell has no or poor ability to uptake or transport a sugar, wherein the hybrid sugar transporter has an increased or enhanced sugar transport activity for transporting the sugar. In some embodiments, the sugar is a pentose, such as xylose. In some embodiments, the host cell is heterologous to the hybrid sugar transporter or sugar transporter.

The present invention provides for a method for constructing a vector of the present invention, the method comprising: introducing the ORF of the hybrid sugar transporter or sugar transporter of the present invention into a vector to produce the sugar transporter of the present invention.

The present invention provides for a method for producing the hybrid sugar transporter or sugar transporter of the present invention, the method comprising: (a) optionally providing a vector of the present invention, (b) introducing the vector into a host cell, and (c) optionally culturing or growing the host cell in a culture medium such that the host cell expresses the sugar transporter and the host cell has an altered capability for transporting sugar into the host cell.

BRIEF DESCRIPTION OF THE DRAWINGS

The foregoing aspects and others will be readily appreciated by the skilled artisan from the following description of illustrative embodiments when read in conjunction with the accompanying drawings.

FIG. 8. Multiple sequence alignment of AGF SWEETs from respective transcriptomes. Coloration denotes AGF group sequence identity above 80%. AtSWEET1 and OsSWEET2b are included as a reference. The amino acid sequences of NcSWEET1, PfSWEET2, AtSWEET1, OsSWEET2b, NcSWEET2, NcSWEET5, ArSWEET1, PfSWEET1, ArSWEET3, NcSWEET4, ArSWEET2, and NcSWEET3 are SEQ ID NO:1, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28, respectively.

FIG. 9. Multiple sequence alignment of AGF SWEETs from respective genomes. Coloration denotes AGF group sequence identity above 80%. AtSWEET1 and OsSWEET2b are included as a reference. The sequence identifiers of the twelve AGF SWEETs are described above.

DETAILED DESCRIPTION OF THE INVENTION

Figure 1:
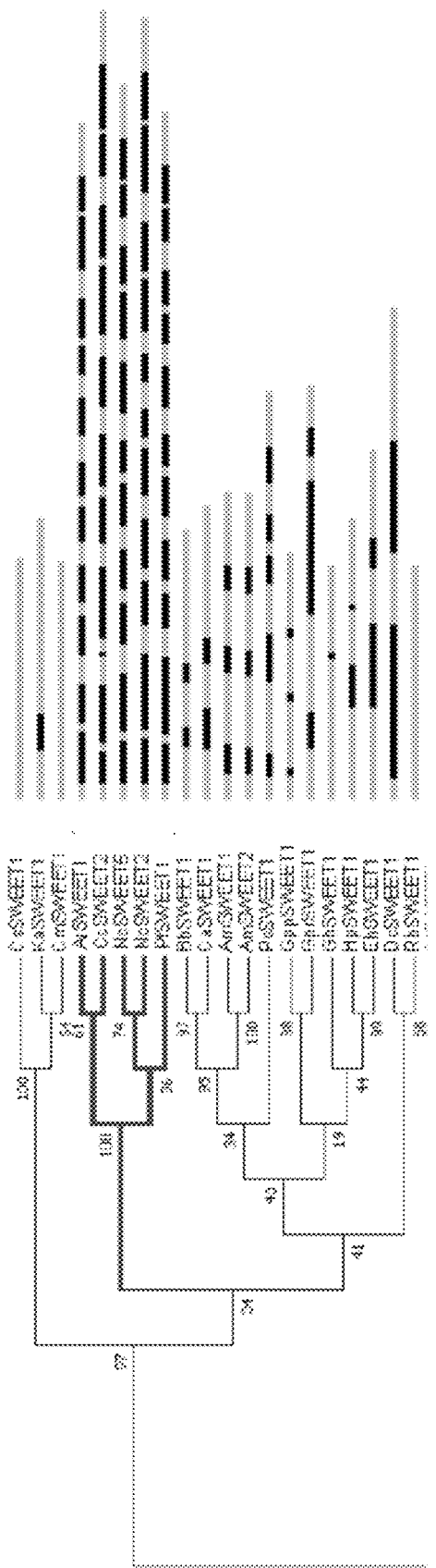
FIG. 1. Phylogenetic analysis of putative fungal SWEETs. The bootstrapped maximum likelihood tree was constructed using RAxML-HPC v.8 with an *Arabidopsis thaliana* SWEET (AtSWEET1, AtSWEET7) outgroup. Coding sequence exon (green line) & intron (black line) organization, derived from corresponding gene models, is shown to scale for each SWEET candidate. (*) The *Piromyces* sp. E2 SWEET (PspSWEET1) contains a predicted 9.9 kb intron which indicated by the break.
Figure 1:
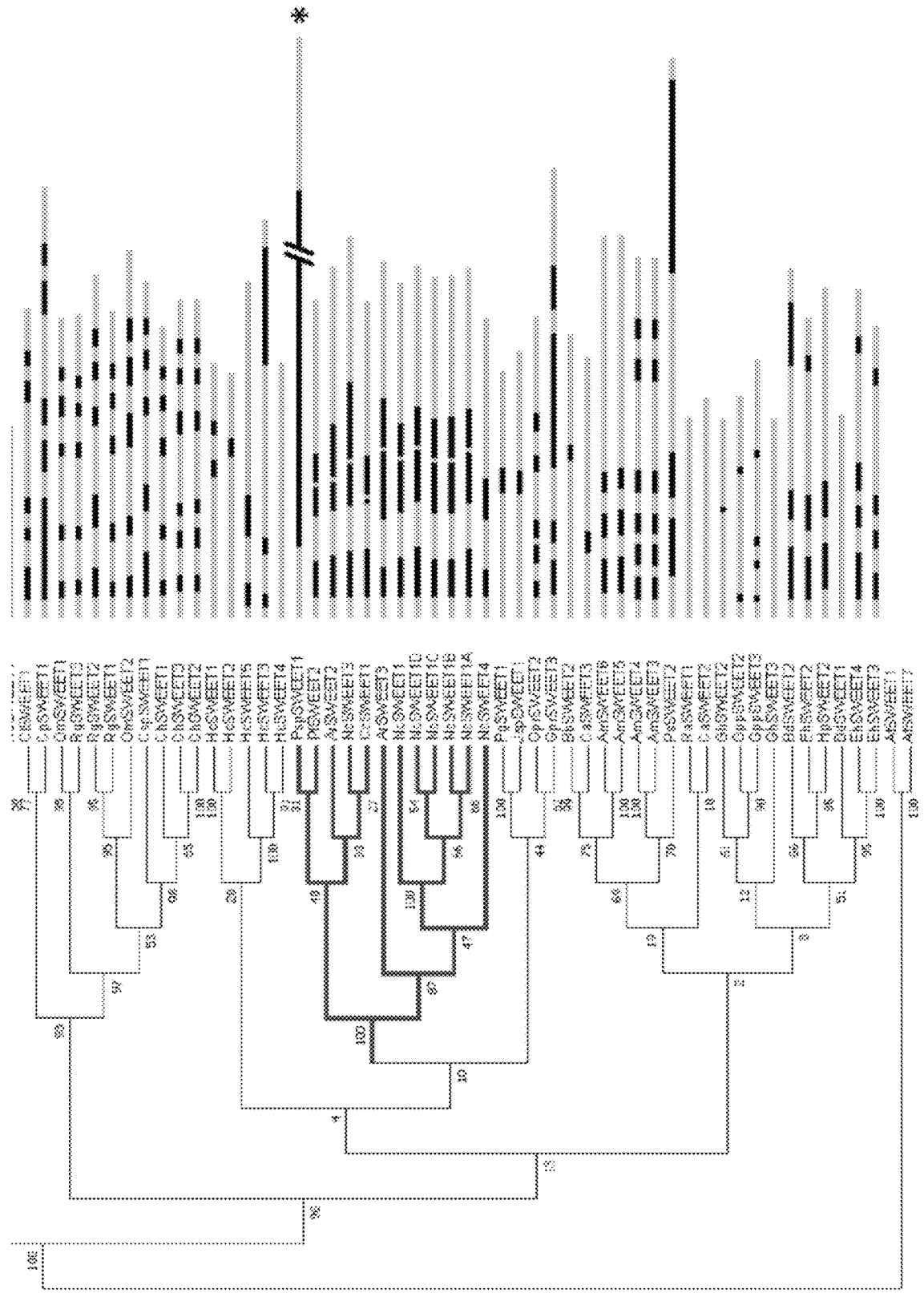

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" when applied to a value, describes a value that includes up to 10% more than the value described, and up to 10% less than the value described.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "heterologous" means a composition that in nature is not connected or is foreign to another composition. For example, a composition is heterologous to another composition as both are not found in nature in the same cell. For example, an ORF and a promoter can be found in the same cell but are heterologous to each other because one is not operatively linked to the other.

The terms "expression vector" or "vector" refer to a compound and/or composition that transforms, or infects a microbe, thereby causing the cell to express nucleic acids and/or proteins other than those native to the cell, or in a manner not native to the cell. An "expression vector" contains a sequence of nucleic acids (ordinarily RNA or DNA) to be expressed by the microbe. Optionally, the expression vector also comprises materials to aid in achieving entry of the nucleic acid into the microbe, such as a virus, liposome, protein coating, or the like. The expression vectors contemplated for use in the present invention include those into which a nucleic acid sequence can be inserted, along with any preferred or required operational elements. Further, the expression vector must be one that can be transferred into a microbe and replicated therein. In some embodiments, the expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "isolated", "purified", or "biologically pure" refer to material that is substantially or essentially free of components that normally accompany it in its native state or free of components from a yeast cell or culture medium from which the material is obtained.

The term "operably linked" refers to a functional linkage between a nucleic acid expression control sequence (such as a promoter) and a second nucleic acid sequence, wherein the expression control sequence directs transcription of the nucleic acid corresponding to the second sequence, such as an ORF.

The term "yeast" refers to any yeast species including: ascosporogenous yeasts (Endomycetales), basidiosporogenous yeasts and yeast belonging to the Fungi imperfecti (Blastomycetes). The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium* and *Filobasidiella*. Yeast belonging to the Fungi Imperfecti are divided into two families, Sporobolomycetaceae (e.g., genera *Sporobolomyces*, Bullera) and Cryptococcaceae (e.g., genus *Candida*). Of particular interest to the present invention are species within the genera *Pichia, Kluyveromyces, Saccharomyces, Schizosaccharomyces* and *Candida*. Of particular interest are the *Saccharomyces* species *S. cerevisiae, S. carlsbergensis, S. diastaticus, S. douglasii, S. kluyveri, S. norbensis* and *S. oviformis*. Species of particular interest in the genus *Kluyveromyces* include *K. lactis*. Since the classification of yeast may change in the future, for the purposes of this invention, yeast shall be defined as described in Biology and Activities of Yeast (F. A. Skinner, S. M. Passmore & R. R. Davenport eds. 1980) (Soc. App. Bacteriol. Symp. Series No. 9). In addition to the foregoing, those of ordinary skill in the art are presumably familiar with the biology of yeast and the manipulation of yeast genetics. See, e.g., Biochemistry and Genetics of Yeast (M. Bacila, B. L. Horecker & A. O. M. Stoppani eds. 1978); The Yeasts (A. H. Rose & J. S. Harrison eds., 2nd ed., 1987); The Molecular Biology of the Yeast *Saccharomyces* (Strathern et al. eds.

Microbe

In some embodiments, the microbe is any prokaryotic or eukaryotic cell, with any genetic modifications, taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/

068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

In some embodiments, the microbe or host cell is a cell that naturally cannot or is impaired for transporting a pentose, such as a xylose, into the microbe or host cell.

Generally, although not necessarily, the microbe is a yeast or a bacterium. In some embodiments, the microbe is *Rhodosporidium toruloides* or *Pseudomonas putida*. In some embodiments, the microbe is a Gram negative bacterium. In some embodiments, the microbe is of the phylum Proteobactera. In some embodiments, the microbe is of the class Gammaproteobacteria. In some embodiments, the microbe is of the order Enterobacteriales. In some embodiments, the microbe is of the family Enterobacteriaceae. Examples of suitable bacteria include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus* taxonomical classes. Suitable eukaryotic microbes include, but are not limited to, fungal cells. Suitable fungal cells are yeast cells, such as yeast cells of the *Saccharomyces* genus.

Yeasts suitable for the invention include, but are not limited to, *Yarrowia, Candida, Bebaromyces, Saccharomyces, Schizosaccharomyces* and *Pichia* cells. In some embodiments, the yeast is *Saccharomyces cerevisae*. In some embodiments, the yeast is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In some embodiments, the yeast is *Candida tropicalis*. In some embodiments, the yeast is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast is an oleaginous yeast. In some embodiments, the oleaginous yeast is a *Rhodosporidium* species. In some embodiments, the *Rhodosporidium* species is *Rhodosporidium toruloides*.

In some embodiments the microbe is a bacterium. Bacterial host cells suitable for the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii, E. marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtherias, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium uropygiale*. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or *S. scabies*. In some embodiments, the *Bacillus* cell is a *B. subtilis, B. megaterium, B. licheniformis, B. anthracis, B. amyloliquefaciens*, or *B. pumilus*.

Example 1

A SWEET Surprise: Anaerobic Fungal Sugar Transporters and Chimeras Enhance Sugar Uptake in Yeast In the yeast *Saccharomyces cerevisiae*, microbial fuels and chemicals production on lignocellulosic hydrolysates is constrained by poor sugar transport. For biotechnological applications, it is valuable to source transporters with novel or enhanced function from nonconventional organisms in complement to engineering known transporters. Here, we identified and functionally screened genes from three strains of early-branching anaerobic fungi (Neocallimastigomycota) that encode sugar transporters from the recently discovered Sugars Will Eventually be Exported Transporter (SWEET) superfamily into *Saccharomyces cerevisiae*. A novel fungal SWEET, NcSWEET1, was identified that localized to the plasma membrane and complemented growth in a hexose transporter deficient yeast strain. Single cross-over chimeras were constructed from a leading NcSWEET1 chassis paired with all other candidate SWEETs to broadly scan the sequence and functional space for enhanced variants. This led to the identification of a chimera, NcSW1/PfSW2:TM5-7, that enhanced the growth rate significantly on glucose, fructose, and mannose. Additional chimeras with varied cross-over junctions identified novel residues in TM1 that affect substrate selectivity. Furthermore, we demonstrate that NcSWEET1 and the enhanced NcSW1/PfSW2:TM5-7 variant facilitated novel co-consumption of glucose and xylose in *S. cerevisiae*. NcSWEET1 utilized 40.1% of both sugars, exceeding the 17.3% utilization demonstrated by the control HXT7(F79S) strain. Our results suggest that SWEETs from anaerobic fungi are beneficial tools for enhancing glucose and xylose co-utilization and offers a promising step towards biotechnological application of SWEETs in *S. cerevisiae*.

Here, we demonstrate that anaerobic gut fungal (AGF) SWEETs act on sugars that are abundant in lignocellulosic hydrolysates, using growth complementation in transporter-deficient *S. cerevisiae* strains. We identified a novel fungal SWEET, NcSWEET1, that demonstrates broad activity on all assayed sugars, including xylose. NcSWEET1 was used as a foundational chassis to recover the functional production of other AGF SWEETs by constructing single cross-over chimeras. This approach broadly scanned the NcSWEET1 protein sequence space, yielding chimeras that significantly enhanced the growth rate on xylose and hexose sugars. Additional protein chimeras, with varied cross-over locations, were used to identify a narrow set of residues that likely modulate substrate selectivity. Further, we evaluated the co-consumption of glucose and xylose by NcSWEET1 and the NcSW1/PfSW2 chimera variants to determine the degree of glucose-mediated inhibition on xylose transport during co-fermentation. This study is the first to demonstrate that SWEETs can transport xylose, and the utility of NcSWEET1 variants as metabolic engineering tools to enhance and overcome sugar transport limitations in *S. cerevisiae*.

2. Materials and Methods

2.1 Identification and Phylogenetic Analysis of Genes Encoding Fungal SWEETs An exhaustive set of coding sequences were previously derived from the transcriptomes of the anaerobic gut fungi *Neocallimastix californiae* (Nc), *Anaeromyces robustus* (Ar), and *Piromyces finnis* (N) (19). The protein domains of these coding sequences were annotated using Pfam libraries (20) with the HMMER web server (21). Annotated sequences were queried for the ubiquitous MtN3/slv motif (pfam03083) (22) to identify putative SWEETs. For the phylogenetic analysis of all Fungal SWEETs, sequences were mined using this method from the Joint Genome Institute (JGI) MycoCosm database (23). Full-length sequences were identified by requiring completeness and a predicted consensus topology of exactly seven transmembrane helix domains using TOPCONS (24). AGF sequences were manually curated using corresponding transcriptomes. Complete fungal SWEETs were clustered using CD-HIT (25) at >95% sequence identity to denote gene duplicates. Exon/intron structures were derived from gene models in MycoCosm. Full-length fungal SWEETs were aligned using ClustalOmega v. 1.2.4 with default parameters (26). RAxML-HPC v.8 (27) was used to construct a maximum likelihood bootstrap phylogenic tree from the alignment after 500 replicates (raxmlHPC-f a-m PROTGAM-MAAUTO-p 12345-x 12345-N 500) on the CIPRES Science Gateway (28). The resulting tree, with bootstrap partition values, was visualized using MEGA7 (29). The same workflow was used to construct a maximum likelihood tree of an alignment that includes the fungal SWEETs and an exhaustive list of sequences detailed by Jia, B. et al (30).

2.2 Strains, Media, and Plasmid Construction

The hexose transporter knock-out *Saccharomyces cerevisiae* strain EBY.VW4000 (CEN.PK2-1C Δhxt1-17 Δstl1 Δagt1 Δydl247w Δyjr160c Δgal2) was a gift from Dr. Eckhard Boles of the Institute of Molecular Biosciences, Goethe-Universität, Germany (31). An HXT-null, xylose screening *S. cerevisiae* strain, SR8D8 (SR8 Δhxt1-7 Δgal2) was constructed by deleting HXT1-7 and GAL2 coding for major hexose transporters via Cas9-based genome editing in the background of *S. cerevisiae* SR8 (32, 33), EBY.VW4000 was routinely grown in SD medium (6.7 g/L Difco yeast nitrogen base (Becton, Dickinson & Co., Sparks, MD, USA), 5 g/L casamino acids (Becton, Dickinson & Co., Sparks, MD, USA), 16.75 g/L sodium citrate dihydrate, 4.2 g/L citric acid monohydrate) supplemented with 2% maltose and required auxotrophic supplements (40 mg/L Tryptophan, 40 mg/L Uracil). SR8D8 was routinely grown in YP-ethanol medium (20 g/L peptone (Becton, Dickinson & Co., Sparks, MD, USA), 10 g/L yeast extract (Becton, Dickinson & Co., Sparks, MD, USA), 2% ethanol). *Escherichia coli* strain DH5α, used for cloning and plasmid propagation, was cultured in lysogeny broth (10 g/L tryptone (Becton, Dickinson & Co., Sparks, MD, USA), 5 g/L yeast extract (Becton, Dickinson & Co., Sparks, MD, USA), 10 g/L NaCl) supplemented with 100 m/mL ampicillin. Anaerobic fungal SWEET genes were codon-optimized for expression in *S. cerevisiae* and synthesized by Genewiz (South Plainfield, NJ, USA). The *S. cerevisiae* HXT7 gene was amplified from a pRS416.HXT7(F79S) plasmid (34) using Phusion DNA polymerase (New England Biolabs, Ipswich, MA, USA). Genes were cloned into pRS316, pRS314, or pRS410 centromeric vectors using EagI and SacII/SpeI restriction enzymes and T4 DNA ligase (New England Biolabs, Ipswich, MA, USA). In the pRS314 and pRS410 vectors, the cloned gene is flanked by an upstream constitutive TEF1 promoter, and a downstream mating factor alpha 1 (MFα1) terminator sequence. In the pRS316 vector, the cloned gene is additionally fused at the 3' end to a gene encoding enhanced green fluorescent protein (eGFP) and a decahistidine tag. Tables 1 and 2 detail the strains and plasmids used in this study. Plasmids were verified by Sanger sequencing (Genewiz, South Plainfield, NJ, USA) and transformed into *S. cerevisiae* strains using the lithium-acetate/PEG method (35). Strain EBY.VW4000 transformants were selected on SD plates (20 g/L Agar) supplemented with 2% maltose and corresponding auxotrophic supplements. Strain SR8D8 transformants were selected on YP-Glycerol (3%), Ethanol (2%) plates (15 g/L Agar) supplemented with 500 μg/mL G-418 antibiotic and subsequently maintained with 200 μg/mL G-418.

TABLE 1

Strains used in this study.

| Strain[a] | Description | Source or Reference |
|---|---|---|
| *Anaeromyces robustus* | Wild type | (1) |
| *Neocallinastix californiae* | Wild type | (1) |
| *Piromyces fruntis* | Wild type | (1) |
| *Escherichia coli* DH5α | Sequenced *E. coli* strain | ATCC (ATCC 68233) |
| *Saccharomyces cerevisiae* BJ546 | Wild type | ATCC (ATCC 208288) |
| *S. cerevisiae* EBY.VW4000 | CEN.PK2-1Chxt1-17Δ gal2Δ::loxP st 11Δ::loxP agt1Δ::loxP mph2Δ::loxP mph3Δ::loxP | (2) |
| *S. cerevisiae* SR8D8 | SR8 hxt1-7Δ gal2Δ | (3) |

[a]This includes anaerobic fungal strains whose transcriptomes were used as a reference for gene synthesis.
1. Haitjema CH. Gilmore SP. Henske JK. Solomon K V.. de Groot R, et al. 2017. A parts list for fungal cellulosomes revealed by comparstive genomics. Nat. Microbiol. 2(8):17087
2. Wieezorke R, Krampe S. Weierstall T. Freidel K Hollenber CP, Boles E. 1995. Concurrent knock-out of at least 20 transporter genes is required to block uptake of hexoses in *Saccharomyces cerevisiae*. FEBS Lett. 464/3): 123-28
3. Xu H. 2015. ENGINEERING *SACCHAROMYCES CEREVISIAE* FOR CELLULOSIC ETHANOL PRODUCTION. University of Illinois at Urbana-Champaign. 1-87 pp.

TABLE 2

Plasmids used in this study.

| Plasmid | Description | Source or Reference |
|---|---|---|
| pRS316 | URA3, CEN6_ARS4 origin | (1) |
| PRS314 | TRP1, CEN6_ARS4 origin | (1) |
| pRS410 | kanMX. CEN6_ARS4 origin | ATCC (ATCC 11258) |
| pRS316-N1 | pRS316-TEF1-NcSWEET1-GFP-His$_{10}$ | This study |
| PRS316-N2 | pRS316-TEF1-NeSWEET2-eGFP-His$_{10}$ | This study |
| PRS316-33 | pRS316-TEF1-NcSWEET3-GFP-His$_{10}$ | This study |
| pRS316-N4 | pRS316-TEF1-NcSWEET4-GFP-His$_{10}$ | This study |
| pRS316-A1 | pRS316-TEF1-ArSWEET1-GFP-His$_{10}$ | This study |

TABLE 2-continued

Plasmids used in this study.

| Plasmid | Description | Source or Reference |
|---|---|---|
| pRS316-A2 | pRS316-TEF1-ArSWEET2-GFP-His$_{10}$ | This study |
| pRS316-A3 | pRS316-TEF1-ArSWEET3-eGFP-His$_{10}$ | This study |
| pRS316-P1 | pRS316-TEF1-PfSWEET1-eGFP-His$_{10}$ | This study |
| pRS316-P2 | pRS316-TEF1-RfSWEET2-eGFP-His$_{10}$ | This study |
| pRS316-H7 | pRS316-TEF1-ScHXT7 | This study |
| PRS314-N1 | pRS314-TEF1-NcSWEET1 | This study |
| pRS314-N2 | pRS314-TEF1-NcSWEET2 | This study |
| pRS314-N3 | pRS314-TEF1-NcSWEET3 | This study |
| pRS314-N4 | pRS314-TEF1-NcSWEET4 | This study |
| pRS314-A1 | pRS314-TEF1-ArSWEET1 | This study |
| pRS314-A2 | pRS314-TEF1-ArSWEET2 | This study |
| pRS314-A3 | pRS314-TEF1-ATSWEET3 | This study |
| pRS314-P1 | pRS314-TEF1-PfSWEET1 | This study |
| pRS314-P2 | pRS314-TEF1-PSWEET2 | This study |
| pRS314-H7 | pRS314-TEF1-ScHXT7 | This study |
| N1/N2:TM5-7 | pRS314-TEF1-NcSWEET1/NcSWEET2 (TM5-7) | This study |
| N1/N3:TM5-7 | pRS314-TEF1-NcSWEET3 (TM5-7) | This study |
| N1/N4:TM5-7 | pRS314-TEF1-NcSWEET1/NESWEET4 (TM5-7) | This study |
| N1/A1:TM5-7 | pRS314-TEF1-NcSWEET1/ArSWEET1 (TM5-7) | This study |
| NI/A1:TM5-7 | pRS314-TEF1-NcSWEET L/ArSWEET2 (TM5-7) | This study |
| NV/A1:TM5-7 | pRS314-TEF1-NcSWEET1/PfSWEET1(TM5-7) | This study |
| N1/PLTM5-7 | pRS314-TEF1-NcSWEET1/PfSWEET1 (TM 5-7) | This study |
| NI/P2:TM5-7 | pRS314-TEF1-NcSWEET1/PfSWEET2 (TM5-7) | This study |
| PRS316-N1/N3 | pRS316-TEF1-NcSWEET1/NcSWEET3-eGFP-Hist | This study |
| pRS316-N1/A3 | pRS316-TEF1-NcSWEET1/ArSWEET3-GFP-Hist | This study |
| pRS316-N1/P2 | pRS316-TEF1-NcSWEET1/PfSWEET2-eGFP-Hisi | This study |
| N1/P2:Ct | pRS314-TEF1-NcSWEET1/PfSWEET2 (C-terminal tail} | This study |
| NcSW1:Tr | pRS314-TEF1-NcSWEET1:Tr | This study |
| N1/P2:TM4-7 | pRS314-TEF1-NcSWEET1/PfSWEET2 (TM4-7) | This study |
| N1/P2:TM3-7 | pRS314-TEF1-NcSWEET1/PfSWEET2 (TM3-7) | This study |
| N1/P2TM2-7 | pRS314-TEF1-NcSWEET1/PfSWEET2 (TM2-7) | This study |
| N1/F2TM1-7 | pRS314-TEF1-NcSWEET1/PfSWEET2 (TM1-7) | This study |
| p416-HXT7(F79S) | p416-pHXT7-ScHXT7(F79S) | (2) |
| PRS410-HXT7 | pRS410-TEF1-HXT7(F79S) | This study |
| pRS410-NcSW1 | pRS410-TEF1-NcSWEET1 | This study |
| pRS410-1/2(57) | pRS410-TEF1-NcSWEET1/PfSWEET2 (TM5-7) | This study |
| pRS410-N1/P2(47) | pRS410-TEF1-NcSWEET1/PfSWEET2 (TM4-7) | This study |
| pRS410-N1/P2(37) | pRS410-TEF1-NcSWEET1/PfSWEET2 (TM3-7) | This study |
| pRS410-N1/P2(27) | pRS410-TEF1-NcSWEET1/PfSWEET2 (TM2-7) | This study |
| pRS410-N1/P2(17) | pRS410-TEF1-NcSWEET1/PfSWEET2 (TM1-7) | This study |

(1) Sikorski. R.S., Hieter, P., 1989. A system of shuttle vectors and yeast host strains designed for efficient manipulation of DNA in *Saccharomyces cerevisiae*. Genetics 122, 19-27.
(2) Rader Apel A, Ouellet M, Szmidt-Middleton H Keating JD. Mukhopadhyay A 2016. Evolved hexose transporter enhances xylose uptake and alucose/xylose co-utilization in *Saccharomyces cerevisise*. Sei. Rep. 5(1)19512

2.3 SWEET Chimera Construction

Single cross-over chimeric transporters were assembled from a pairing between NcSWEET1 and other anaerobic gut fungal SWEETs using USER cloning with the PfuX7 polymerase (36, 37). PfuX7 was a gift from Dr. Morten Nørholm of the Novo Nordisk Foundation Center for Biosustainability, Technical University of Denmark, Denmark. Alignment of AGF SWEET sequences using Clustal Omega (26) guided in silico assembly and the design of USER primers targeting a cross-over location that immediately follows the fourth predicted transmembrane-segment. Additional single cross-over chimeras were constructed between NcSWEET1 and PfSWEET2 that varied the cross-over position. All primers are detailed in Table 3. The nucleotide sequences of primers P1 to P48 are SEQ ID NO:29 to SEQ ID NO:74, and SEQ ID NOs:11 and 15, respectively.

TABLE 3

Primers used in this study

| ID | Description | 5'→3' Sequence |
|---|---|---|
| P1 | MFαlt, SacI, Rev | CATAGAGCTCAATTCTCTTAGGATTCGATTCACATTCATCT |
| P2 | TEF1p, EcoRI Fwd | CATAGAATTCAGATCTGTTTAGCTTGCCTCGTCCC |
| P3 | MFαlt, SpeI, Fwd | CATAACTAGTGAAAATGTTTCAGTTGATACAGCTATGACTTTACAA |
| P4 | NcSW1, SpeI, Rev | CATAACTAGTGAAAATGTTTCAGTTGATACAGCTATGACTTTACAA |
| P5 | NcSW2, SpeI, Rev | CATAACTAGTTAATAATAACTTAAGAGTTGAAGACATGGGTATCTATTACTG |
| P6 | NcSW3, SpeI, Rev | CATAACTAGTATTTTTCATATGAAATGGTGTCATTTGAATAGTATTTTGTG |

TABLE 3-continued

Primers used in this study

| ID | Description | 5'→3' Sequence |
|---|---|---|
| P7 | ArSW1, SpeI, Rev | CATAACTAGTATTTTTCAAATGAAATGGAGTCATTTGAATTGTATT |
| P8 | ArSW2, SpeI, Rev | CATAACTAGTCCATGGAGAATACAACATAGTTGAGTTACCTT |
| P9 | ArSW3, SpeI, Rev | CATAACTAGTAATATTAATAACCTTTTCATTAATATTTTCTTCAATTTTCTTATCTGC |
| P10 | PfSW1, SpeI,, Rev | CATAACTAGTATTTTTTAAATGAAATGGAGTCATTTGAATAGTATTATGTGG |
| P11 | PfSW2, SpeI, Rev | CATAACTAGTACCATACAAAGTAGTAGAATTAGCGTTCAATGG |
| P12 | HXT7, EagI, Fwd | CATACGGCCGATGTCACAAGACGCTGCTATTGCAG |
| P13 | HXT7, SpeI, Rev | CATAACTAGTTTTGGTGCTUAACATTCTCTTGTACAATGG |
| P14 | pRS, USER, Fwd | ACACAGACAAGA[U]GAAACAATTCGGCA |
| P15 | pRS, USER, Rev | ATCTTGTCTGTG[U]AGAAGACCACACACG |
| P16 | N1/N2, USER, Rev | ACCTCTATTGAACAAAA[U]AAAAGACAAAGCACCACCACA |
| P17 | N1/N3, USER, Rev | ATCTTTGAACAAAA[U]AAAAGACAAAGCACCACCACA |
| P18 | N1/N4, USER, Rev | ATTGTCATCGAACAAAA[U]AAAAGACAAAGCACCACCAC |
| P19 | N1/A1, USER, Rev | AGAACCATTGTTC[U]TGAAUAAAATAAAAGACAAAGCAC |
| P20 | N1/A2, USER, Rev | ATCTTTGAACAAAA[U]AAAAGACAAaGCACCACCACA |
| P21 | N1/A3, USER, Rev | ATCATGGAACAAAA[U]AAAAGACAAAGCACCACCACA |
| P22 | N1/P1, USER, Rev | ACCTUTATTGAACAAAA[U]AAAAGACAAAGCACCACCA€ |
| P23 | N1/P2, USER, Rev | ATCTTTGAACAAAA[U]AAAAGACAAAGCACCACCACA |
| P24 | N1/N2, USER, Fwd | ATTTTGTTCAATAGAGG[U]TTGAAATCTTATACTATTTTAGGTTTTATTTCTTC |
| P25 | N1/N3, USER, Fwd | ATTTTGTTCAAAGA[U]AACTATGAAGCTGCAAAAAACTGTATGG |
| P26 | N1/N4, USER, Fwd | ATITTGTTCGATGACAA[U]TATGAAGCTGCTAAAAACTCTATGG |
| P27 | N1/A1, USER, Fwd | AGAACAATGGTTC[U]ACTTCTTATACTGTTTTGGGTTTTATTAC |
| P28 | N1/A2, USER, Fwd | ATTTTGTTCAAAGA[U]AATTATACAGCTGCTAAAAATTGTATGGT |
| P29 | N1/A3, USER, Fwd | ATTTTGTTCCATGA[U]GACTACCCAAAAGCTAAAAACACTATTG |
| P30 | N1/P1, USER, Fwd | ATTTGTTCAATAGAGG[U]ATTACTTCTTATAATGTTTTGGGTTTTATTTG |
| P31 | N1/P2, USER, Fwd | ATTTTGTTCAAAGA[U]AATTATGATGCTGCTAAAAACTGTATGGGT |
| P32 | NcSW3, SacII, Rev | CATACCGCGGTITTTCATATGAAATGGTGTCATTTGAATAGTATTTTGTG |
| P33 | ArSws, SacII, Rev | CATACCGCGGAATATTAATAACCTTTTCATTAATATTTTCTTCAATTTTCTTATCTGC |
| P34 | PfSW2, SacII, Rev | CATACCGCGGACCATACAAAGTAGTAGAATTAGCGTTCAATGG |
| P35 | N1/P2:Ct, USER, Fwd | ATTTTTATGGAAAA[U]AAAAAACAACAAGAATTGCAACAAAGCAG |
| P36 | N1/P2:Ct, USER, Rev | ATTTTCCATAAAAA[U]TCTGGTAAGAATTCTCAAGAATTG |
| P37 | NcSW1:tr, USER, Fwd | AAGAAACTAGTTAA[U]AATAACTTAAGAGTTGAAGACATGGG |
| P38 | NcSW1:Tr, USER, Rev | ATTAACTAGTTTCT[U]TTTTAGGATAAATAAAAAACAACAAGAATTG |
| P39 | N1/P2:TM4-7, USER, Fwd | ATTTTGTTTTCTTC[U]AACATGAAGCCAAAAGATTTTAAATOGACT |

TABLE 3-continued

Primers used in this study

| ID | Description | 5'→3' Sequence |
|---|---|---|
| P40 | N1/P2:TM3-7, USER, Fwd | ACAATCATTGGAC[U]TTCTGGCCAAACTTGG |
| P41 | N1/P2:TM2-7, USER, Fwd | ACCATTTAAGGAA[U]TACAAAATTTGAAAAAATCTAATGGTCAATG |
| P42 | N1/P2:TM1-7, USER, Fwd | AATTATTACTGAAAC[U]GTTTTTCCATTGTGTGGT |
| P43 | N1/P2:TM1-7, USER, Rev | AGAAGAAACAAAA[U]CATAATATAATATTGACCCAAAATAATACCAC |
| P44 | N1/P2-TM3-7, USER, Rev | AGTCCAATGATTG[U]GAATAACAAAAGAATACAAGTCTTGGGAC |
| P45 | N1/P2:TM2-7, USER, Rev | ATTCCTTAAATGG[U]GATAAAAAGATAAAATAAGCTGTAAAACAACC |
| P46 | N1/P2:TM1-7, USER, Rev | AGTTTAGTAATAAT(U]TCACAAGCTTGAGAAGTGC |
| P47 | MFα, SalI, Rev | CATAGTCGACAATTCTCTTAGGATTCGATTCACATTCATCT |
| P48 | TEF1p, BamHI, Fwd | CATAGGATCCAGATCTGTTTAGCTTGCCTCGTCCC |

2.4 GFP Fluorescence Imaging

EBY.VW4000 cultures expressing SWEET-eGFP genes were grown in SD (-Ura) supplemented with 2% maltose to an optical density at 600 nm ($OD_{600}$) of ~2.0. Yeast cells were washed twice using 1×PBS buffer and diluted to $OD_{600}$ 0.1. Samples were transferred to chamber slide wells (Thermo Fisher Scientific, Waltham, MA, USA) coated with 0.1% (w/v) poly-1-lysine (Sigma-Aldrich, St. Louis, MO, USA) and allowed to settle for 15 minutes. Fluorescence imaging of yeast cells was performed on an Olympus Fluoview FV1000 confocal laser scanning microscope using a PLAPON 60XOSC2/1.40NA objective. eGFP fluorescence was visualized by excitation at 488 nm and emission detection at 510 nm.

2.5 Growth Complementation Assay

Strain EBY.VW4000 was used to screen for hexose transport activity. HXT7(F79S) and the empty vector were used as controls. Yeast colonies were picked from agar plates and grown in liquid medium to $OD_{600}$~2.0. Cells were washed twice in deionized water and diluted to $OD_{600}$ 0.1. Serial dilutions were plated onto SD (-Ura) or (-Ura, -Trp) plates supplemented with 2% maltose (control) or 2% glucose; 2% fructose; or 2% mannose. Plates were incubated at 30° C. for 4 days and photographed using the Bio-Rad ChemiDoc MP imaging system (Bio-Rad, Hercules, CA, USA). Xylose growth complementation was evaluated in strain SR8D8 by monitoring the $OD_{600}$ of triplicate 4 mL cultures. Cultures were inoculated at a starting $OD_{600}$ 0.1 as previously described and sampled daily over five days.

2.6 Sugar Consumption Assay

SR8D8 strains were grown on YP-ethanol with 200 μg/mL G-418 to an $OD_{600}$~2-3, washed twice with deionized water, and inoculated in triplicate into 5 mL YP-GX (2.5% D-glucose, 2.5% D-xylose) supplemented with 200 μg/mL G-418. The depletion of D-glucose and D-xylose in solution was monitored using a YSI 2950D biochemistry analyzer (YSI Incorporated, Yellow Springs, OH, USA). Sugar concentrations and the $OD_{600}$ of each culture were measured daily over five days.

3. Results 3.1 Identification and Phylogenetic Analysis of Fungal SWEETs

The characteristics of fungal SWEETs are poorly described and based on only nine complete sequences from three species (30). To deepen the understanding of fungal SWEET diversity, all fungal genomes in the MycoCosm portal were queried for predicted genes with the MtN3/slv motif (pfam03083). The resulting 83 entries were deduplicated and further filtered after membrane topology prediction for the canonical seven transmembrane helices of eukaryotic SWEETs. Sequences from the anaerobic gut fungi *Neocallimastix californiae* (Nc), *Anaeromyces robustus* (Ar), *Piromyces finnis* (N), and *Caecomyces churrovis* (Cc) were manually verified using corresponding transcriptomes (38, 39). This search identified 71 full-length fungal SWEET sequences from 30 fungal species belonging to five phyla: Basidiomycota, Blastocladiomycota, Chytridiomycota, Cryptomycota, and Zoopagomycota (Table 4). This set includes all previously described, complete fungal SWEETs (30, 40). Apart from two SWEET homologs found in the higher-order phylum Basidiomycota, fungal SWEETs belong to early-diverging fungal lineages. Seven gene duplicates were identified after clustering, including four duplicates of the AGF NcSWEET1. Most of these fungi are symbionts of host organisms and saprotrophic.

TABLE 4

SWEET sequences identified from assembled genomes available in the Mycocosm database. Protein ID numbers correspond to unique identifiers within a given assembly.

| SWEET ID | Clade | Organism & Genome Assembly | Phylum | ID# | Ref. |
|---|---|---|---|---|---|
| AmSWEET1 | I | *Allomyces macrogynus* ATCC 38327 | Blastociadiomycota | 7200 | — |
| AmSWEET2 | I | *Allomyces macrogynus* ATCC 38327 | Blastociadiomycota | 13064 | — |
| AmSWEET3 | II | *Allomyces macrogynus* ATCC 38327 | Blastociadiomycota | 1507 | — |
| AmSWEET4 | II | *Allomyces macrogynus* ATCC 38327 | Blastociadiomycota | 18075 | — |
| AmSWEET5 | II | *Allomyces macrogynus* ATCC 38327 | Blastociadiomycota | 16614 | — |
| AmSWEET6 | II | *Allomyces macrogynus* ATCC 38327 | Blastociadiomycota | 6030 | — |
| ArSWEET1 | I | *Anaeromyces robustus* v1.0 | Chytridiomycota | 290897 | (1) |
| AlSWEET2 | II | *Anaeromyces robustus* v1.0 | Chytridiomycota | 236039 | (1) |
| AlSWEET3 | II | *Anaeromyces robustus* v1.0 | Chytridiomycota | 291099 | (1) |
| BbSWEET1 | I | *Blastociadiella britannica* v1.0 | Blastociadiomycota | 372883 | — |
| BBSWEET2 | II | *Blastociadiella britannica* v1.0 | Blastociadiomycota | 378665 | — |
| BdSWEET1 | II | *Batrachochytrium dendrobatidis* JAMS v1.0 | Chytridiomycota | 16153 | — |
| BASWEET2 | II | *Batrachochytrium dendrobatidis* JAM81 v1.0 | Chytridiomycota | 36766 | — |
| CaSWEET1 | I | *Catenaria anguillalae* PL171 v2.0 | Blastociadiomycota | 1084816 | (2) |
| CaSWEET2 | II | *Catenaria anguillalae* PL171 v2.0 | Blastociadiomycota | 51343 | (2) |
| CaSWEET3 | II | *Catenaria anguillalae* PL171 v2.0 | Blastociadiomycota | 121314 | (2) |
| CeSWEETl | II | *Caecomyces churrovis* A v1.0 | Chytridiomycota | 421479 | (3) |
| CeSWEET2 | I | *Caecomyces churrovis* A v1.0 | Chytridiomycota | 452194 | (3) |
| ChSWEET1 | II | *Chytriomyces hyalinus* JEL632 v1.0 | Chytridiomycota | 608356 | — |
| ChSWEET2 | II | *Chytriomyces hyalinus* JEL632 v1.0 | Chytridiomycota | 608348 | — |
| ChSWEET3 | II | *Chytriomyces hyalinus* JEL632 v1.0 | Chytridiomycota | 639362 | — |
| ClSWEET1 | II | *Chytridium lagenaria* Arg66 v1.0 | Chytridiomycota | 212214 | — |
| CmSWEET1 | I | *Coemansia mojavensis* RSA 71 v1.0 | Zoopagomycota | 522374 | — |
| CPSWEET1 | II | *Cladochytrium polystomum* WB228 v1.0 | Chytridiomycota | 858157 | — |
| CspSWEET1 | II | *Chytriomyces sp.* MP 71 v1.0 | Chytridiomycota | 1093906 | — |
| CsSWEET1 | I | *Coemansia spiralis* RSA 1278 v1.0 | Zoopagomycota | 228313 | — |
| DeSWEET1 | I | *Dimargaris cristalligena* RSA 468 single-cell v1.0 | Zoopagomycota | 29179 | (4) |
| EhSWEET1 | I | *Entophlyetis helioforms* JEL805 v1.0 | Chytridiomycota | 455491 | — |
| EhSWEET2 | II | *Entophlyctis helioformis* JEL805 v1.0 | Chytridiomycota | 507073 | — |
| EhSWEET3 | II | *Entophlyctis helioformis* JEL805 v1.0 | Chytridomycota | 515811 | — |
| EhSWEET4 | II | *Entophlyctis helioformis* JEL805 v1.0 | Chytridiomycota | 515810 | — |
| GhSWEET1 | I | *Gorgonomyces haynaldii* MP57 v1.0 | Chytridiomycota | 212799 | — |
| GhSWEET2 | II | *Gorgonomyces haynaldii* MP57 v1.0 | Chytridiomycota | 229800 | — |
| GhSWEET3 | II | *Gorgonomyces haynaldii* MP57 v1.0 | Chytridiomycota | 10744 | — |
| GppSWEET1 | I | *Globomyces pollinis-pini* Arg68 v1.0 | Chytridiomycota | 619450 | — |

TABLE 4-continued

SWEET sequences identified from assembled genomes available in the
Mycocosm database. Protein ID numbers correspond to unique identifiers within a given
assembly.

| SWEET ID | Clade | Organism & Genome Assembly | Phylum | ID# | Ref. |
|---|---|---|---|---|---|
| GppSWEET2 | II | *Globomyces pollinis-pini* Arg68 v1.0 | Chytridiomycota | 572227 | — |
| GppSWEET3 | II | *Globomyces pollinis-pini* Arg68 v1.0 | Chytridiomycota | 616459 | — |
| GprSWEET1 | I | *Gonapodya prolifera* v1.0 | Chytridiomycota | 75834 | (5) |
| GprSWEET2 | I | *Gonapodya prolifera* v1.0 | Chytridiomycota | 201379 | (5) |
| GprSWEET3 | II | *Gonapodya prolifera* v1.0 | Chytridiomycota | 54321 | (5) |
| HcSWEET1 | I | *Hyaloraphidium curvatum* SAG235-1 v1.0 | Chytridiomycota | 669219 | — |
| HcSWEET2 | II | *Hyaloraphidium curvatum* SAG235-1 v1.0 | Chytridiomycota | 692297 | — |
| HcSWEET3 | II | *Hyaloraphidium curvatum* SAG235-1 v1.0 | Chytridiomycota | 709908 | — |
| HcSWEET4 | II | *Hyaloraphidium curvatum* SAG235-1 v1.0 | Chytridiomycota | 472801 | — |
| HcSWEET5 | II | *Hyaloraphidium curvatum* SAG235-1 v1.0 | Chytridiomycota | 663276 | — |
| HpSWEET1 | I | *Homolaphlyctis polyrhiza* JEL142 v1.0 | Chytridiomycota | 5300 | (6) |
| HpSWEET2 | II | *Homolaphlyctis polyrhiza* JEL142 v1.0 | Chytridiomycota | 1185 | (6) |
| JspSWEET1 | II | *Jaminaea* sp. MCA 5214 v1.0 | Basidiomycot | 227740 | (7) |
| KaSWEET1 | I | *Kickxella alabastrina* RSA 675 v1.0 | Zoopagomycota | 180536 | — |
| NcSWEET1 | II | *Neocallimastix californiae* G1 v1.0 | Chytridiomycota | 450485 | (1) |
| NeSWEET1A | II | *Neocallimastix californiae* G1 v1.0 | Chytridiomycota | 672410 | (1) |
| NcSWEET1B | II | *Neocallimastix californiae* G1 v1.0 | Chytridiomycota | 672411 | (1) |
| NcSWEET1C | II | *Neocallimastix californiae* G1 v1.0 | Chytridiomycota | 672409 | (1) |
| NcSWEET1D | II | *Neocallimastix californiae* G1 v1.0 | Chytridiomycota | 672412 | (1) |
| NcSWEET2 | I | *Neocallimastix californiae* G1 v1.0 | Chytridiomycota | 207465 | (1) |
| NcSWEET3 | II | *Neocallimastix californiae* G1 v1.0 | Chytridiomycota | 79940 | (1) |
| NcSWEET4 | I | *Neocallimastix californiae* G1 v1.0 | Chytridiomycota | 460436 | (1) |
| NcSWEET5 | I | *Neocallimastix californiae* G1 v1.0 | Chytridiomycota | 667320 | (1) |
| OmSWEET1 | II | *Obelidium mucronatum* JEL8G2 v1.0 | Chytridiomycota | 852033 | — |
| OmSWEET2 | II | *Obelidium mucronatum* JEL802 v1.0 | Chytridiomycota | 920091 | — |
| PfSWEET1 | I | *Piromyces finnis* v3.0 | Chytridiomycota | 583192 | (1) |
| PfSWEET2 | II | *Piromyces finnis* v3.0 | Chytridiomycota | 331754 | (1) |
| PgSWEET1 | II | *Pseudomicrostronia glucosiphilum* MCA 4718 v1.0 | Basidiomycota | 284347 | (7) |
| PspSWEET1 | II | *Piromyces* sp. E2 v1.0 | Chytridiomycota | 41852 | (1) |
| PsSWEET1 | I | *Paraphysoderma sedebokerense* JEL821 v1.0 | Blastocladiomycota | 1170225 | — |
| PsSWEET2 | II | *Paraphysoderma sedebokerense* JEL821 v1.0 | Blastocladiomycota | 73074 | — |
| RaSWEET1 | II | *Rozella allomycis* CSP55 single-cell v1.0 | Cryptomycota | 31310 | (4) |
| RbSWEET1 | I | *Ramicandelaber brevisporus* CBS 109374 v1.0 | Zoopagomycota | 160626 | — |
| RgSWEET1 | II | *Rhizoclosmatium globosum* JEL800 v1.0 | Chytridiomycota | 724887 | (2) |

TABLE 4-continued

SWEET sequences identified from assembled genomes available in the Mycocosm database. Protein ID numbers correspond to unique identifiers within a given assembly.

| SWEET ID | Clade | Organism & Genome Assembly | Phylum | ID# | Ref. |
|---|---|---|---|---|---|
| RgSWEET2 | II | Rhizoclosmatium globosum JEL800 v 1.0 | Chytridiomycota | 703951 | (2) |
| RgSWEET3 | II | Rhizoclosmatium globosum JEL800 v1.0 | Chytridiomycota | 722081 | (2) |

1. Haitijema CH, Gilmore SP, Henske JK, Solomon K V., de Groot R. et al. 2017. A parts list for fungal cellulosomes revealed by comparative genomics. Nat. Microbiol. 2(8):170877
2. Mondo SJ Dannebaum RO, Kuo RC, Louie KB, Bewick AJ, et al. 2017. Widespread adenine N6-methylation of active genes in fungi Nat Genet. 49(5):964-68
3. Henske JK. Gilmore SP, Knop D, Cunningham FJ. Sexton JA, et al. 2017. Transcriptemic characterization of Caecomyces churrovis: A novel, non-rhizoid-forming lignocellulolytic anaerobic fungus. Biotechnol. Biofuels. 10(1):1-2
4. Ahrendt SR. Quandt CA. Clobanu D, Chum A. Salamov A, et al 2018. Leveraging single-cell genomics to expand the fungal tree of life. Nat Microbiol. 3(12)1417-28
5. Chang Y. Wang S, Sekimoto S. Aerts AL, Choi C. et al. 2015. Phylogenomic analyses indicate that early fungi evolved digesting cell walls of algal ancestors of land plants. Genome Biol. Evol 7(6):1590-1601
6. Toseson S, Stanich JE. Shiu SH, Resenblum EB 2011. Genomic transition to pathogenicity in chytrid fungi. PLoS Pathog. 7(11)
7. Kijpomnyongpan T. Mondo SJ, Barry K. Sandor L, Lee J. et al. 2018. Broad genomic sampling reveals a smut pathogenic ancestry of the fungal clade ustilaginomycotina. Mol. Biol Evol 35(8):1840-54

Structural resolution of eukaryotic plant SWEETs, OsSWEET2b (41) and AtSWEET13 (42), has identified residues that form the substrate-binding pocket and both extracellular and intracellular gates. These residues show conservation across eukaryotic lineages (30), and point mutagenesis at these positions in AtSWEET1 predominantly yielded loss-of-function mutants (30, 41, 43). Fungal SWEETs show significant conservation of residues at positions that correspond to the extracellular gate and substrate-binding pocket (Table 4). Residue conservation may also correspond with functional conservation across the SWEET superfamily.

Figure 7:
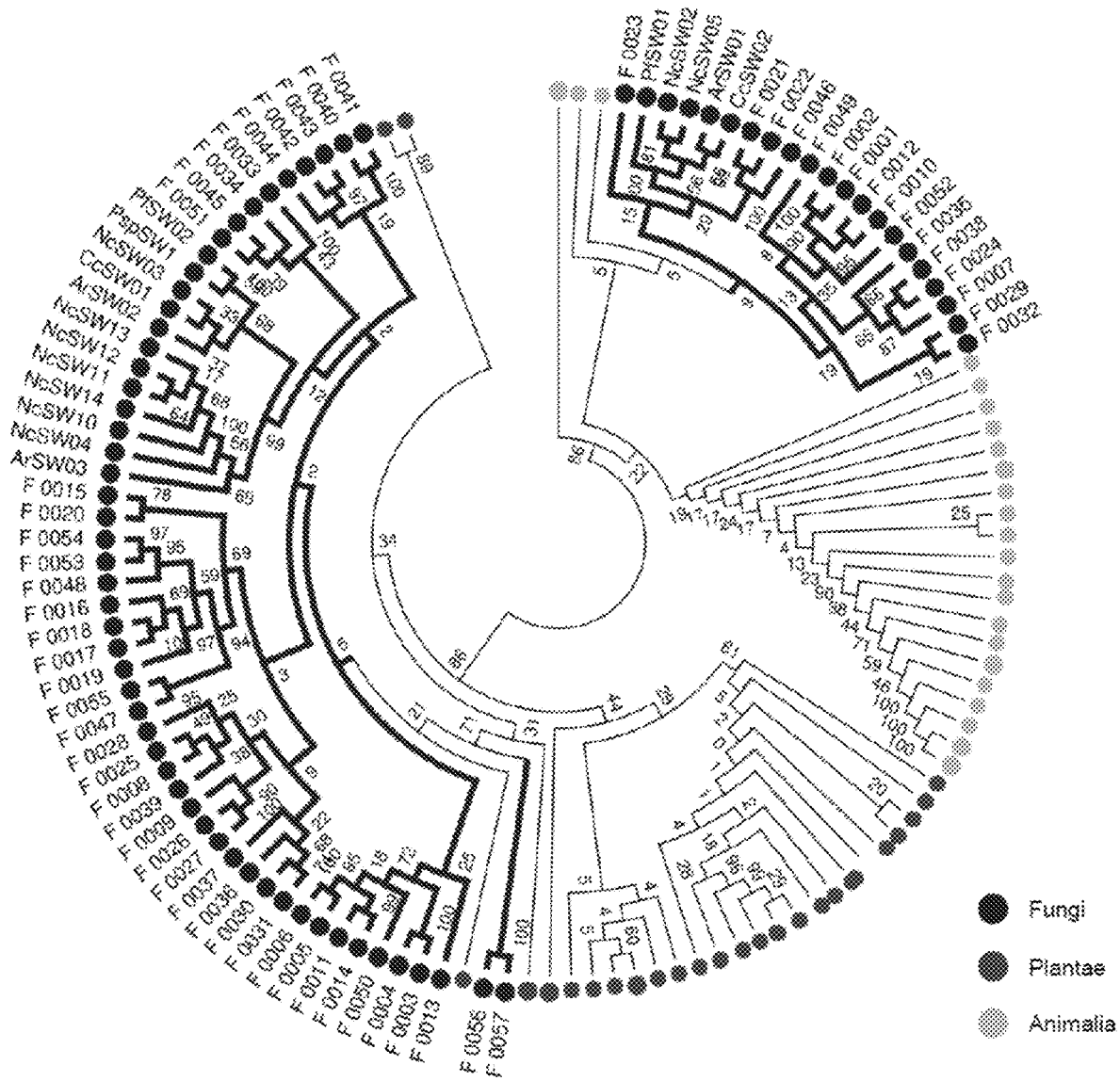
FIG. 7. Phylogenetic analysis of all SWEETs. The bootstrapped maximum likelihood tree was constructed using RAxML-HPC v.8 from an alignment of 72 fungal SWEETs identified in this work and 2,392 SWEETs in the kingdoms Plantae and Animalia retrieved from (30). Nodes are colored based on the kingdom of origin.

A maximum-likelihood phylogenic tree with bootstrap bipartition statistics was constructed using RAxML-HPC after amino acid sequence alignment using ClustalOmega (FIG. 1). Further, corresponding gene annotations in Mycocosm were used to map exon/intron structures for each sequence. Fungal SWEETs form two distinct clades supported by high bipartition values. Of the fungal species that encode more than one SWEET, >70% possess members of both clades. Exon/intron structure was highly variable in both clades, but subgroups composed of single fungal families demonstrated conservation, e.g., AGF SWEETs. Of most interest is the exon/intron organization of AGF SWEETs in clade I that are predicted to all encode 11 introns. This level of fragmentation is typically only observed in Plantae SWEETs (40), possibly denoting functional conservation (44). A tree was also constructed from an alignment of Fungal SWEETs with 2300 Plant and Animalia SWEETs detailed in (30) (FIG. 7). Interestingly, the two clades are recovered and separately nest within Plant and Animalia node abundant branches.

3.2 Heterologous Expression of Anaerobic Gut Fungal SWEETs

Figure 2:
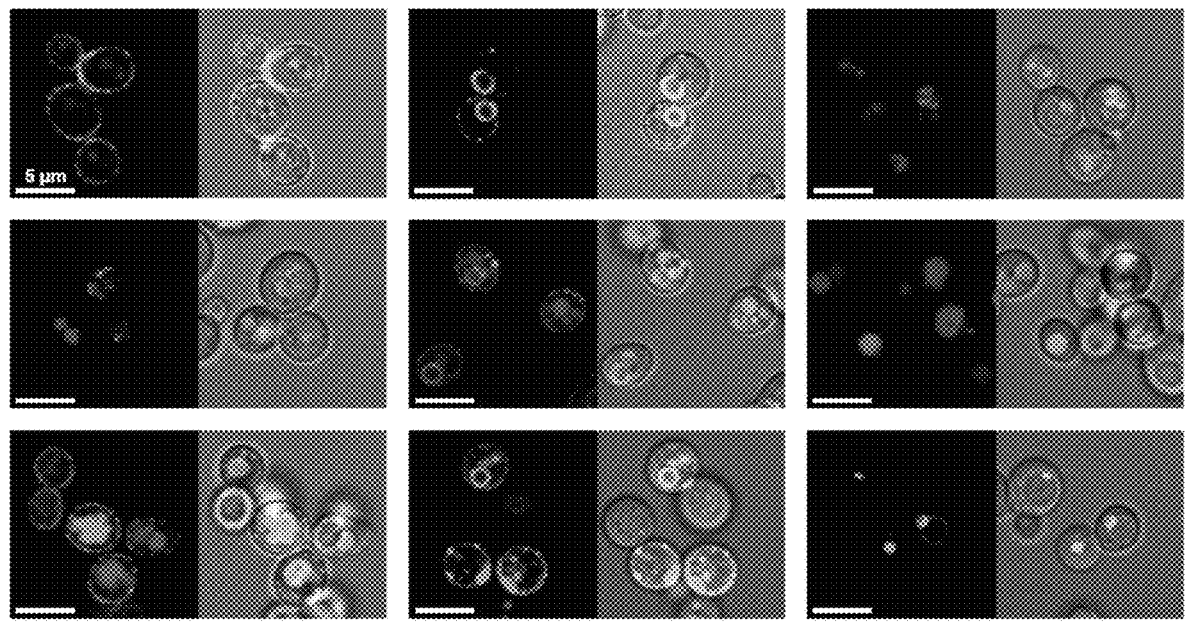
FIG. 2. AGF SWEET strain eGFP fluorescence localization. First row from left to right: NcSWEET1-3; second row from left to right: NcSWEET4, ArSWEET1-2; third row from left to right: ArSWEET3, PfSWEET1-2. Laser intensities were kept identical across samples FIG. 3. Spot growth assay of AGF SWEET candidates. Growth on SD (-ura) plates with respective carbon sources was captured after incubation at 30 C for 4 d. Spotting was organized in ten-fold serial dilutions from left to right.
Figure 8:
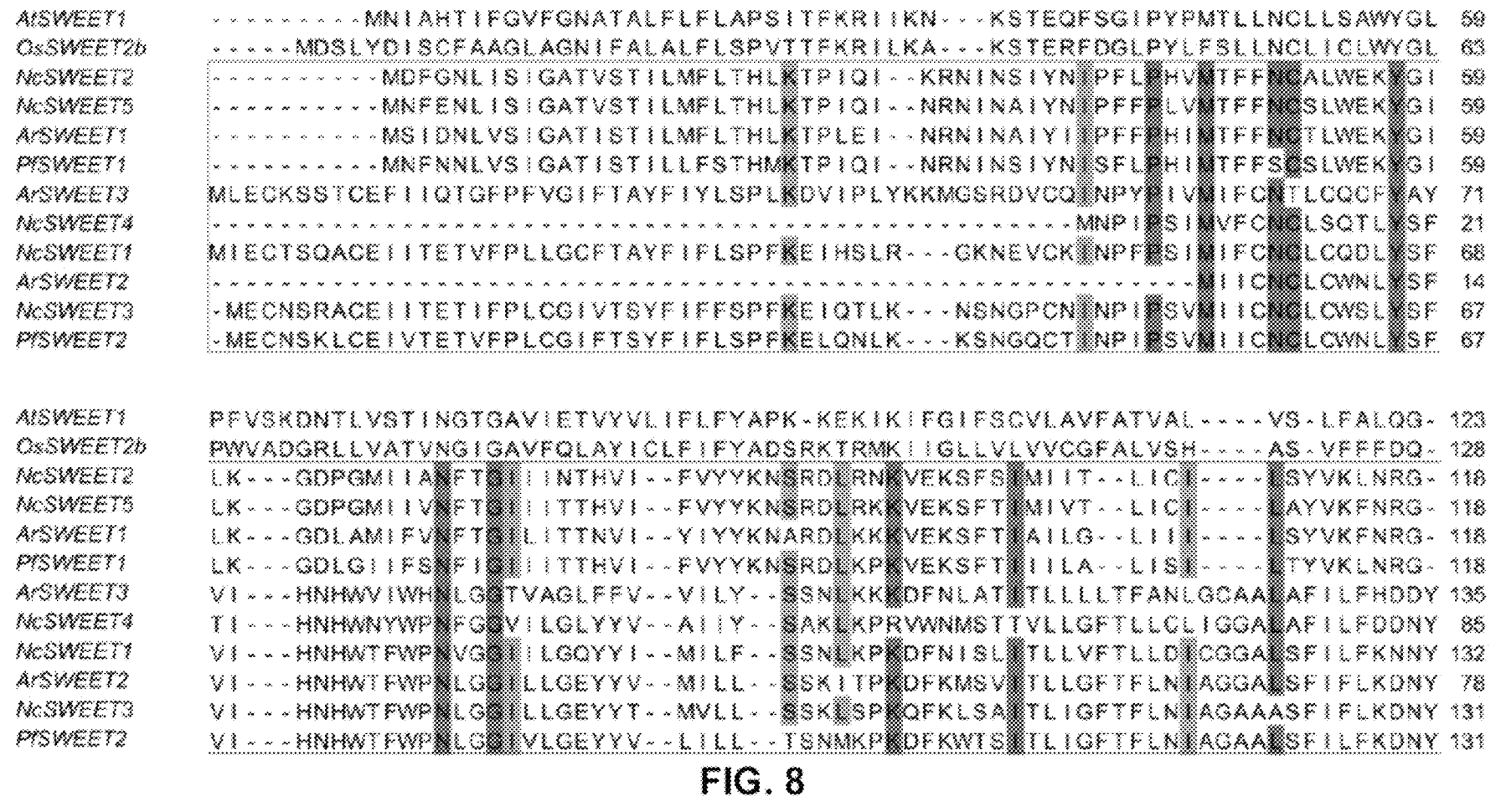
Figure 8:
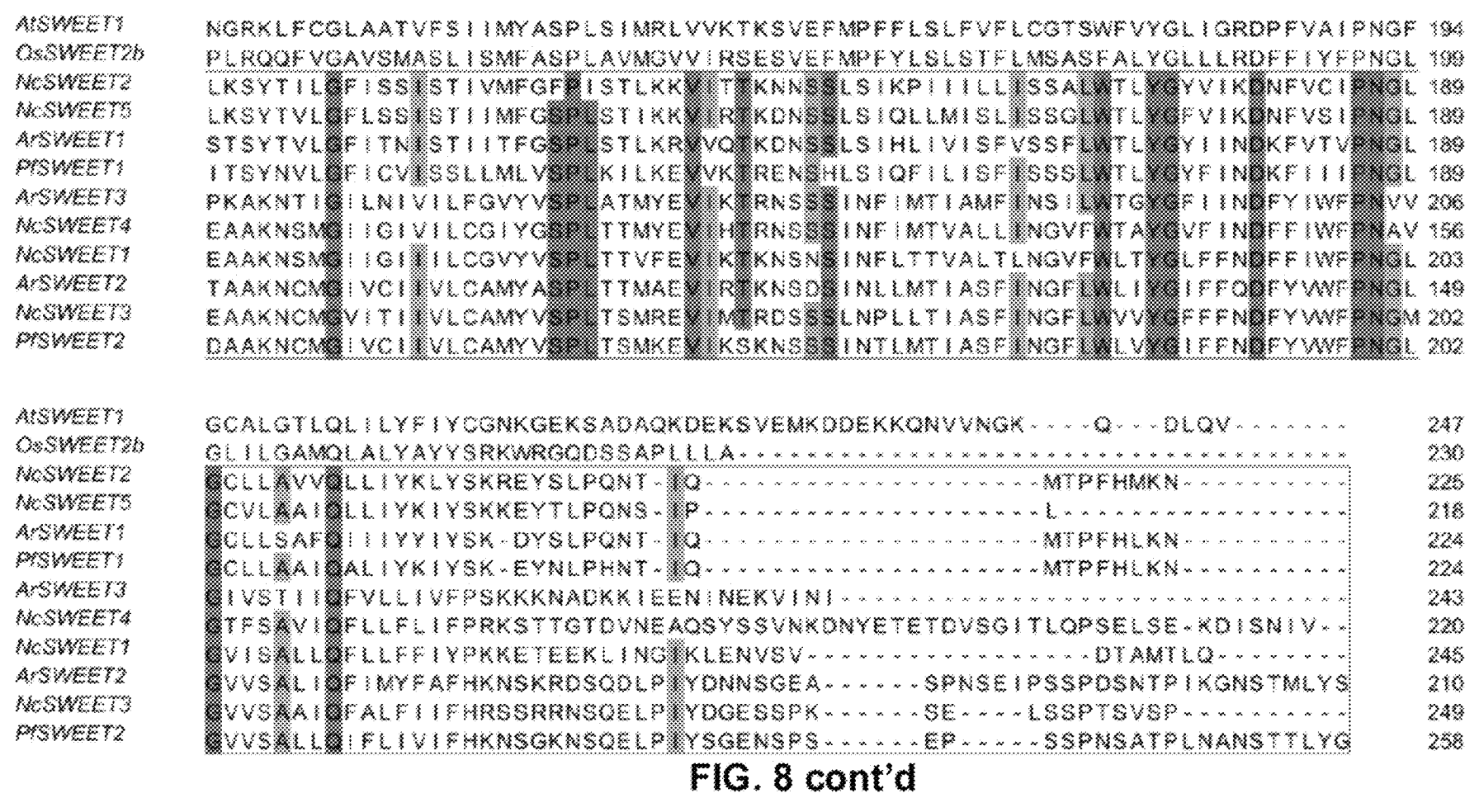
Figure 9:
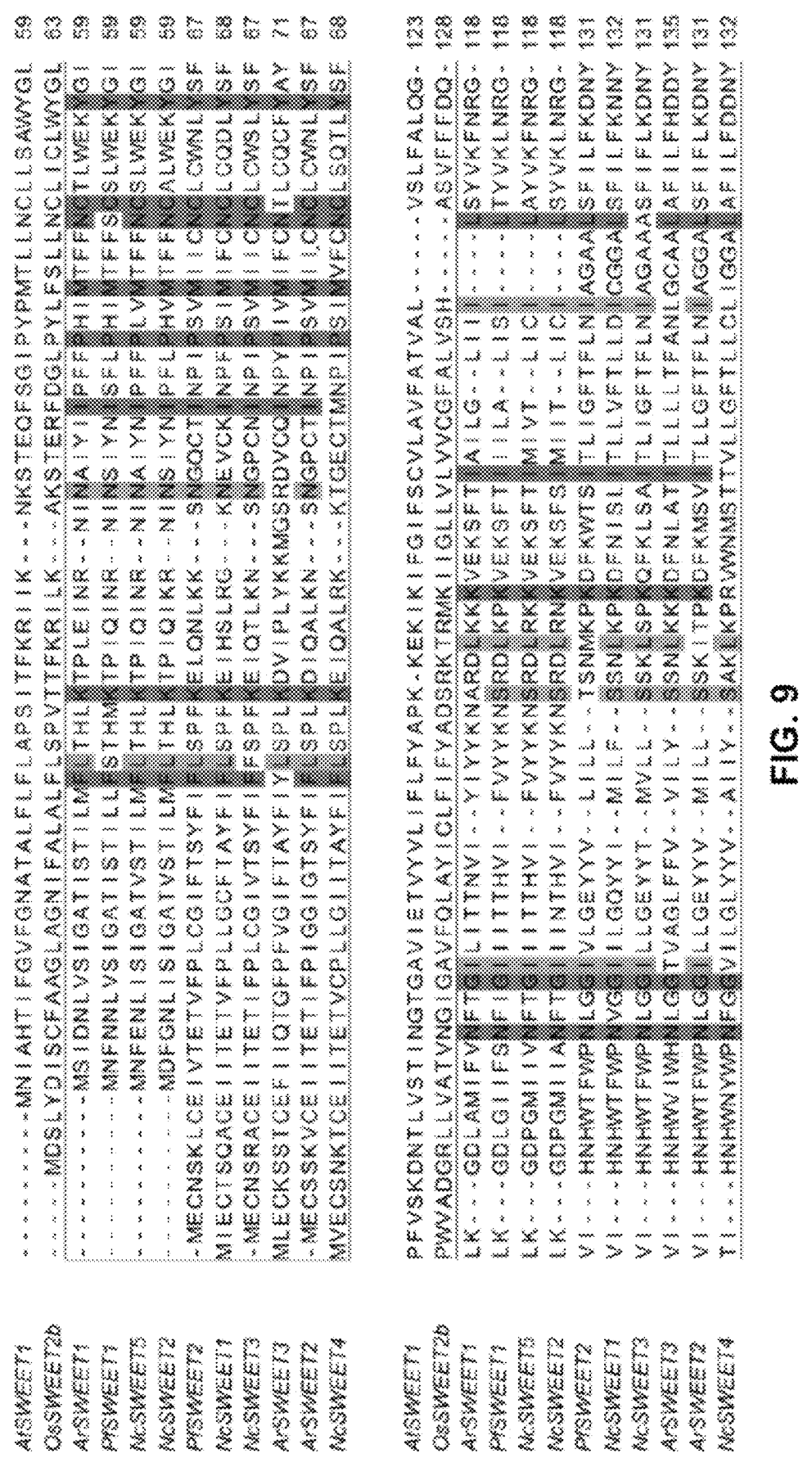
Figure 9:
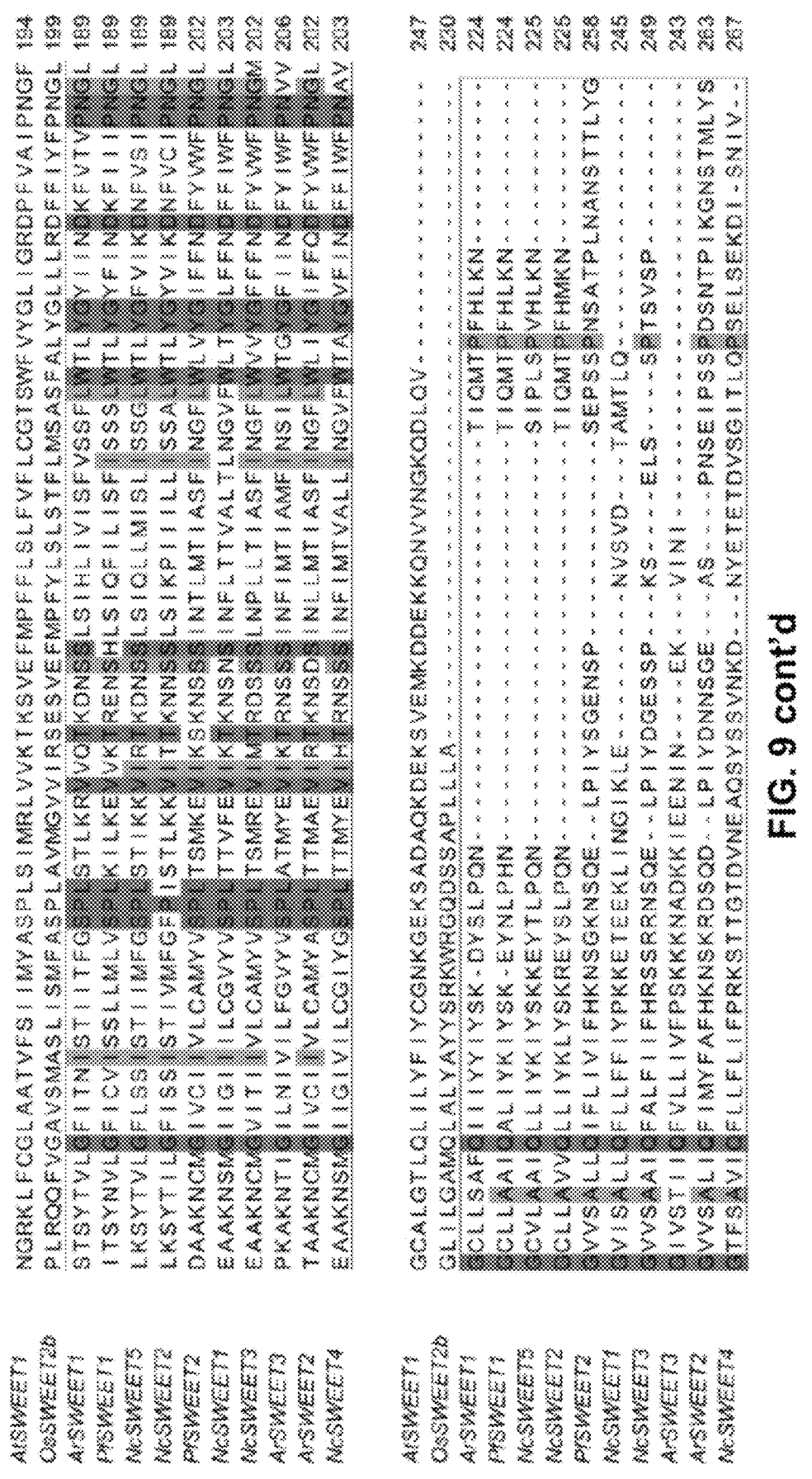

AGF SWEETs were selected for synthesis before any genomic sequencing, and thereby limited to nine sequences previously annotated in the transcriptomic data collected from the anaerobic gut fungi N. californiae (Nc), A. robustus (Ar), and P. finnis (N) (12): NcSWEET1-4, ArSWEET1-3, and PfSWEET1-2, respectively. Transmembrane (TM) topology prediction using the TOPCONS web server (24) revealed that NcSWEET4 and ArSWEET2 sequences were likely truncated at the amino (N)-terminus, encoding only six and five TMs, respectively (FIG. 8). Nevertheless, as the transcriptomic coding sequence appeared otherwise complete, NcSWEET4 and ArSWEET2 were included in this study. Full length sequences for NcSWEET4 and ArSWEET2 were subsequently resolved using corresponding genomes (45) (FIG. 9). All AGF SWEET sequences were codon optimized for expression in S. cerevisiae and subsequently synthesized. After cloning into a pRS316 vector encoding a C-terminal eGFP-His$_{10}$ fusion tag, the genes were expressed in the S. cerevisiae strain EBY.VW4000. Confocal micrographs were taken of cultures in mid-log growth to evaluate the capacity for heterologous production and intracellular trafficking to the plasma membrane (FIG. 2).

Fluorescent protein production is evident in all recombinant strains, but individual SWEETs display wide-ranging sub-cellular localization patterns. As seen in FIG. 2, only NcSWEET1, ArSWEET1, ArSWEET3, and PfSWEET1 demonstrate fluorescent signals at the cell periphery. Punctuation of this signal is similar to observations made by Seppälä et al. during heterologous expression of AGF fluoride transporters (13), attributed to possible retention of a pool of transporters within the cortical endoplasmic reticulum (ER). Accumulation in other intracellular compartments of ArSWEET1 and ArSWEET3 strains may reflect the burden on native translational and secretory pathway machinery exacerbated by strong constitutive expression. NcSWEET4 and ArSWEET2 appear to lack ER localization, a phenotype consistent with the predicted truncation of N-terminal features recognized by secretory pathway chaperone proteins during membrane protein biogenesis. Conversely, NcSWEET3 fails to localize to the ER despite high (~75%) shared sequence identity with NcSWEET1. Poor functional conservation of the AGF SWEET leader peptides in S. cerevisiae may contribute to inconsistencies in secretory pathway trafficking and thereby the capacity for heterologous production.

3.3 N. Californiae SWEET1 Transports Hexose Sugars

Figure 3:
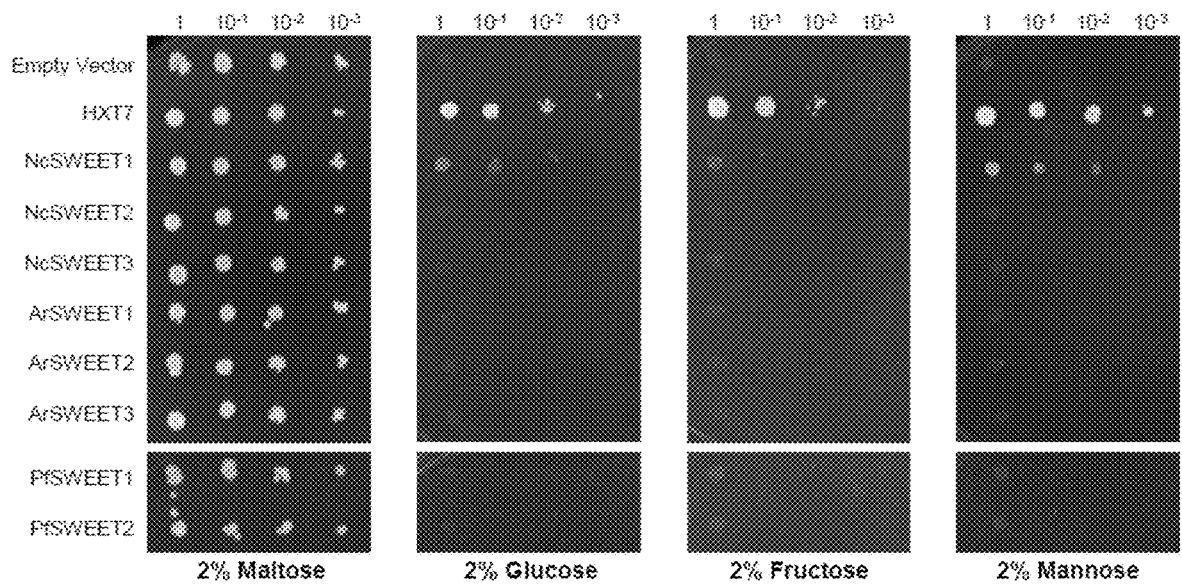
Figure 4:
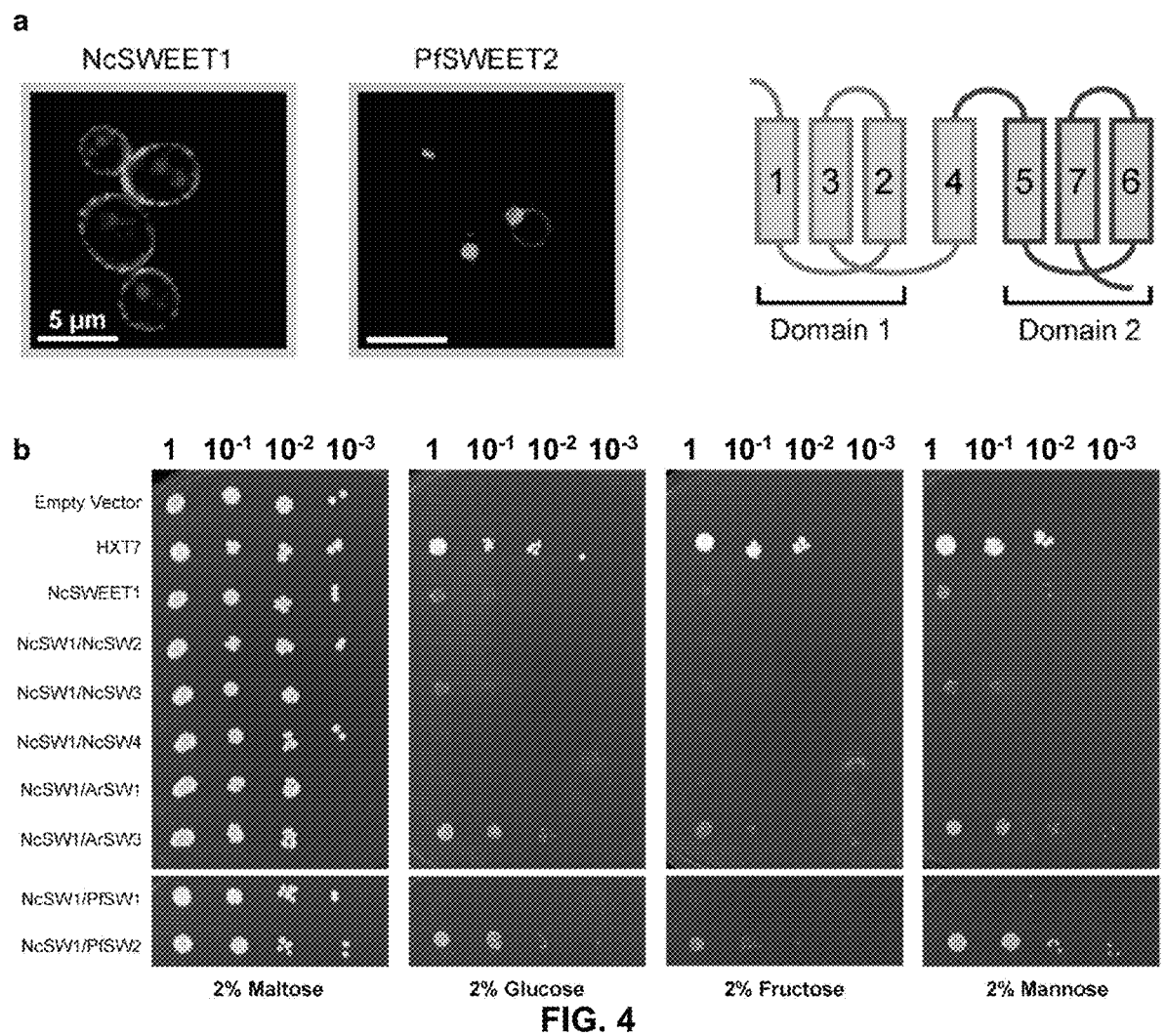
FIG. 4. SWEET chimera construction and spot growth assay. (a) Single cross-over chimeras were formed by swapping the second domain with that of other candidates; (b) Spot assay evaluation of SWEET chimera activity after a 4d incubation at 30° C.
Figure 10:
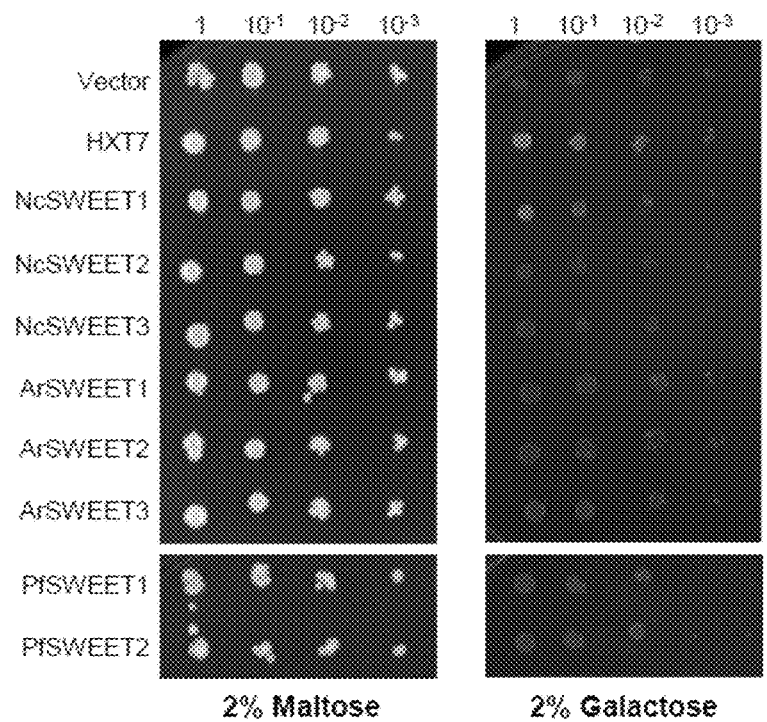
FIG. 10. Spot growth assay of AGF SWEET candidates on galactose. Growth on SD (-ura) plates with respective carbon sources was captured after incubation at 30 C for 4 d. Spotting was organized in tenfold serial dilutions from left to right.
Figure 11:
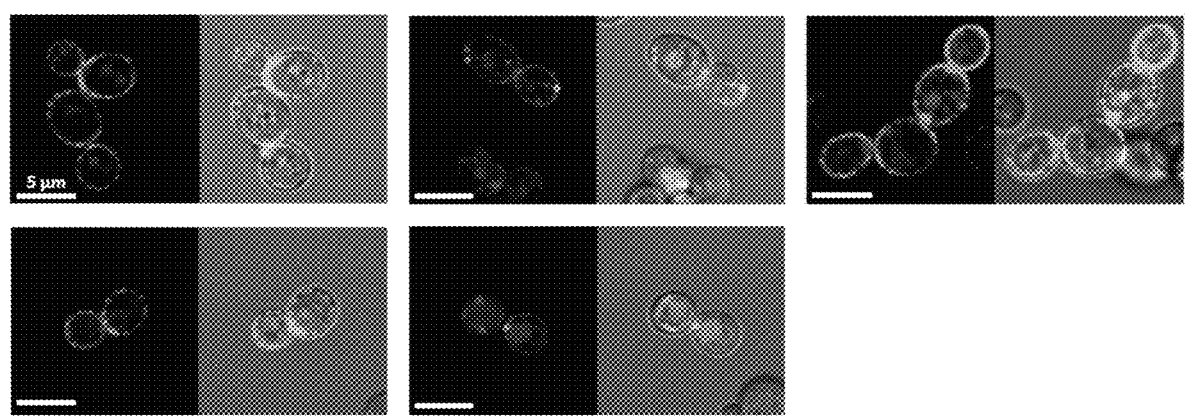
FIG. 11. Localization of NcSWEET1 point mutants. Confocal micrographs organized from left to right: (Top) NcSWEET1, P52A, P154A; (Bottom) W185G, N201A. Laser intensities were kept identical across samples.

The activity of AGF SWEETs on hexose sugars was assayed by growth complementation in the hexose transporter knock-out strain EBY.VW4000. Of the nine candidate AGF SWEETs, only NcSWEET1 recovered growth on media supplemented with 2% glucose, 2% fructose, or 2% mannose as sole carbon sources (FIG. 3). The NcSWEET1 strain also demonstrated growth above the control on 2% galactose (FIG. 10), suggestive of a broad native role as a general hexose transporter in N. californiae. Poor functional production of the remaining AGF SWEETs was consistent with observed plasma membrane trafficking incompatibilities in S. cerevisiae.

Figure 5:
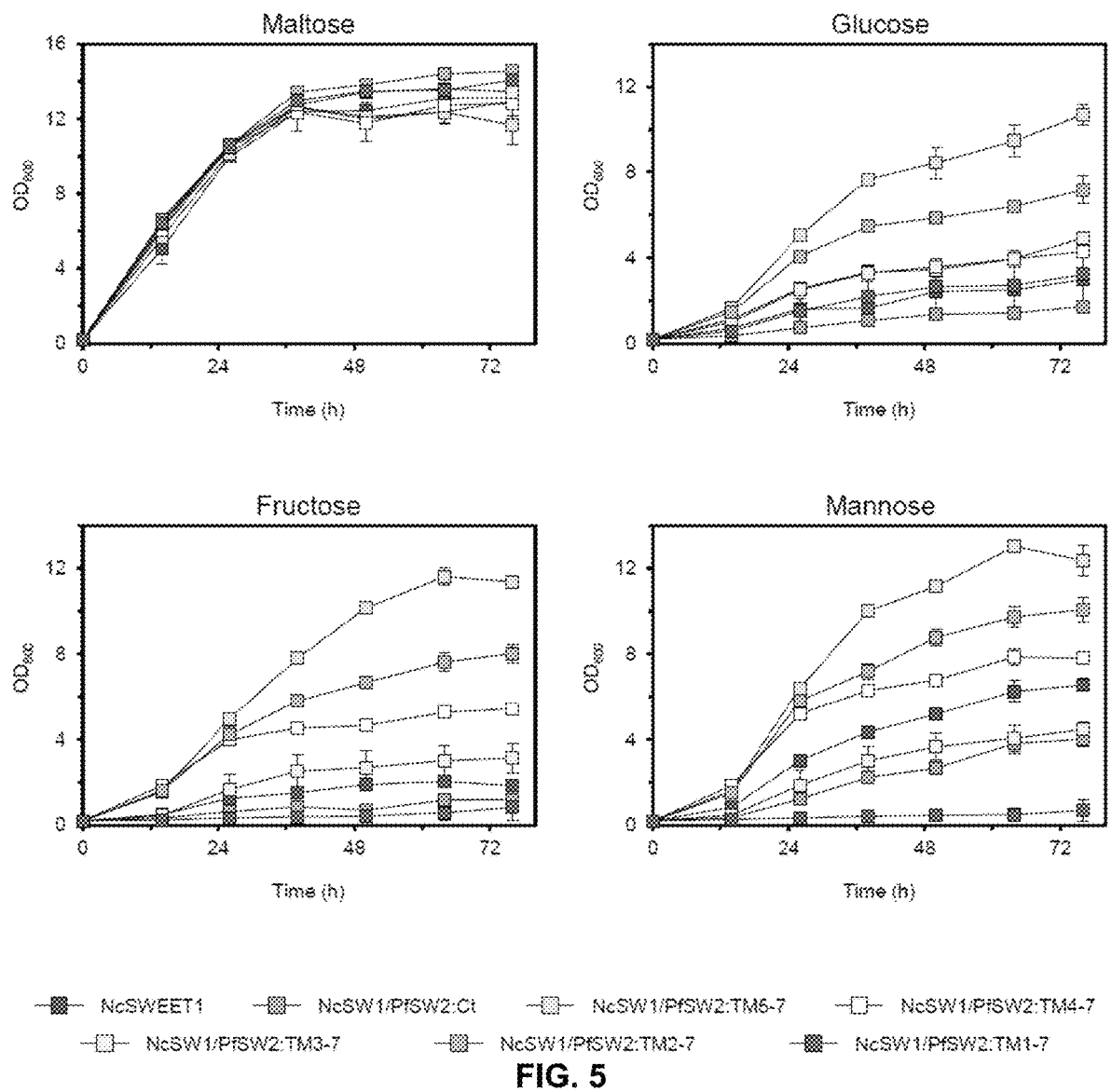
FIG. 5. Evaluation of NcSWEET1/PfSWEET2 chimera growth on hexose sugars.
Figure 6:
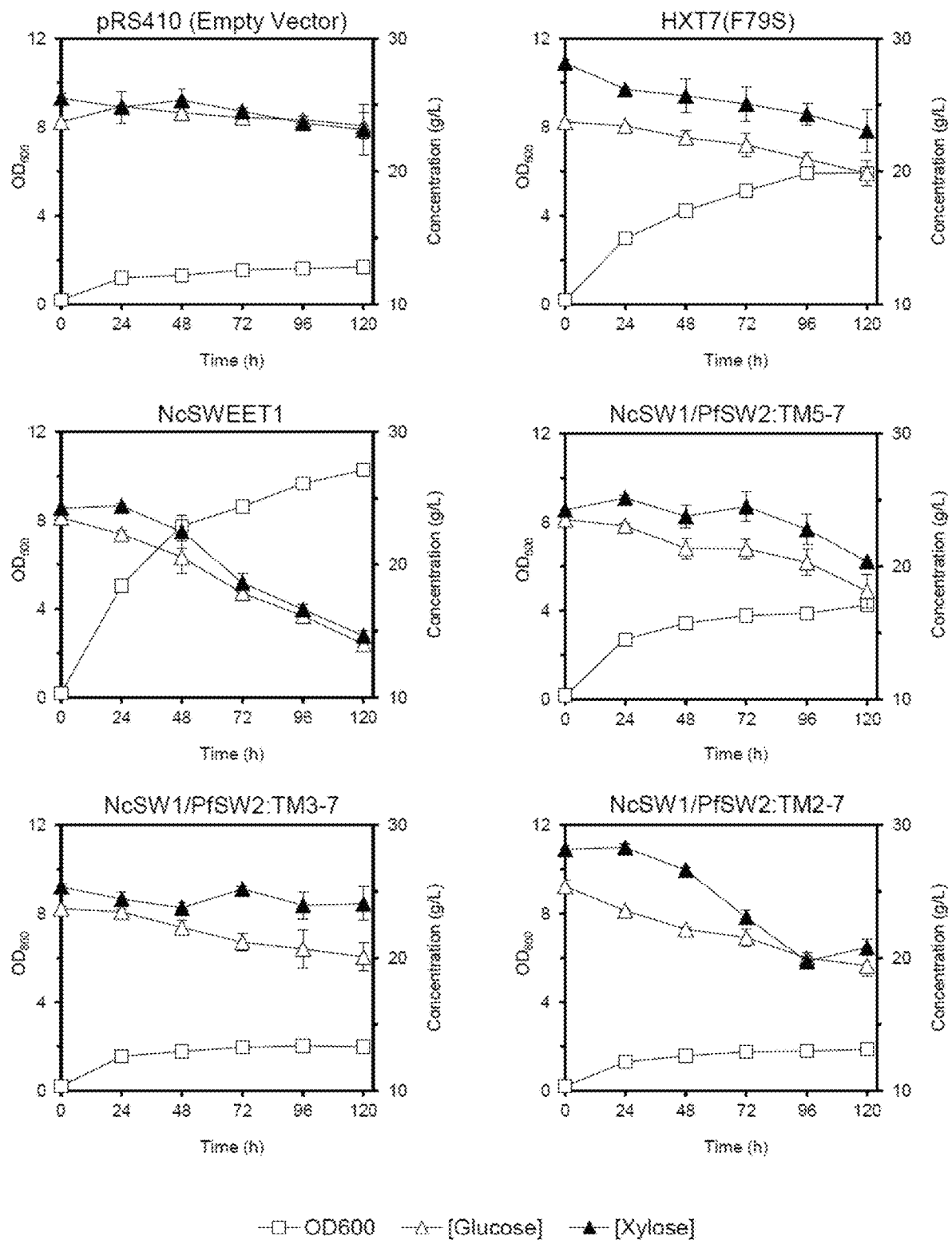
FIG. 6. Evaluation of glucose and xylose co-consumption by SR8D8 expressing AGF SWEETs.
Figure 12:
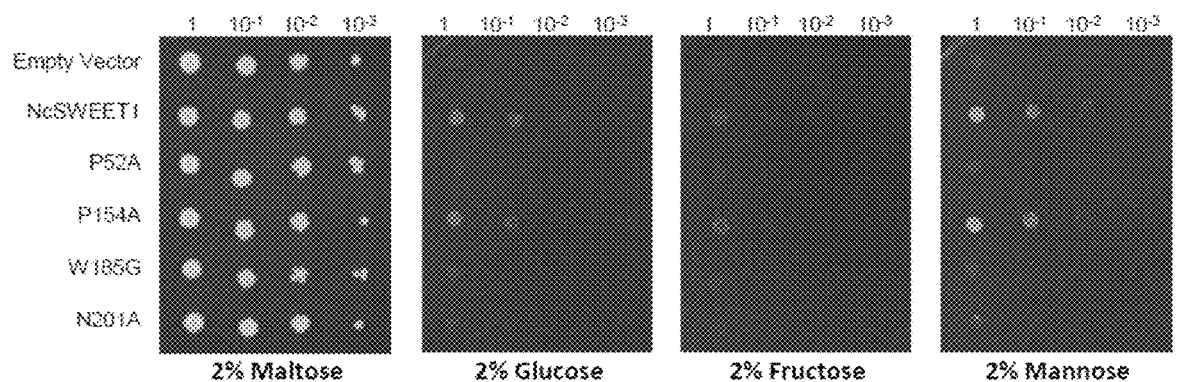
FIG. 12. Spot growth assay of NcSWEET1 point mutants. Growth on SD (-ura) plates with respective carbon sources was captured after incubation at 30 C for 4 d. Spotting was organized in ten-fold serial dilutions from left to right.
Figure 13:
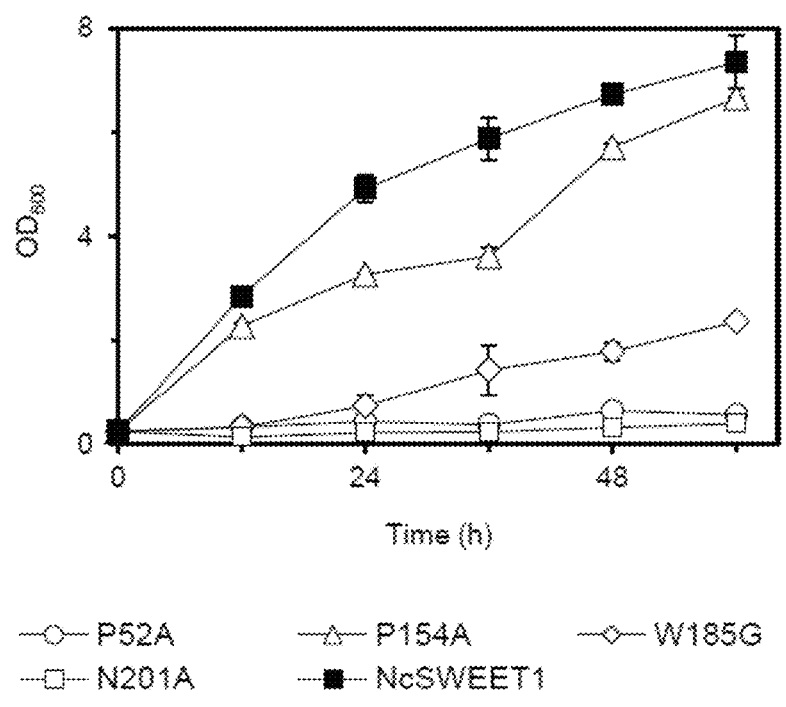
FIG. 13. NcSWEET1 point mutant and wild-type co-expression growth phenotypes. Growth of strains expressing NcSWEET1 point mutants. Cultures were grown in triplicate on SD(-ura) and SD(-ura,-trp) respectively, supplemented with 2% glucose.
Figure 14:
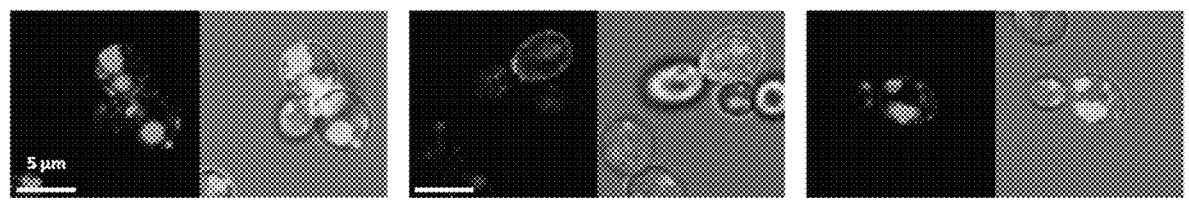
FIG. 14. Localization of NcSWEET1 chimeras. Confocal micrographs organized from left to right: NcSWEET1/NcSWEET5, NcSWEET1/ArSWEET3, NcSWEET1/PfSWEET2. Laser intensities were kept identical across samples.
Figure 15:
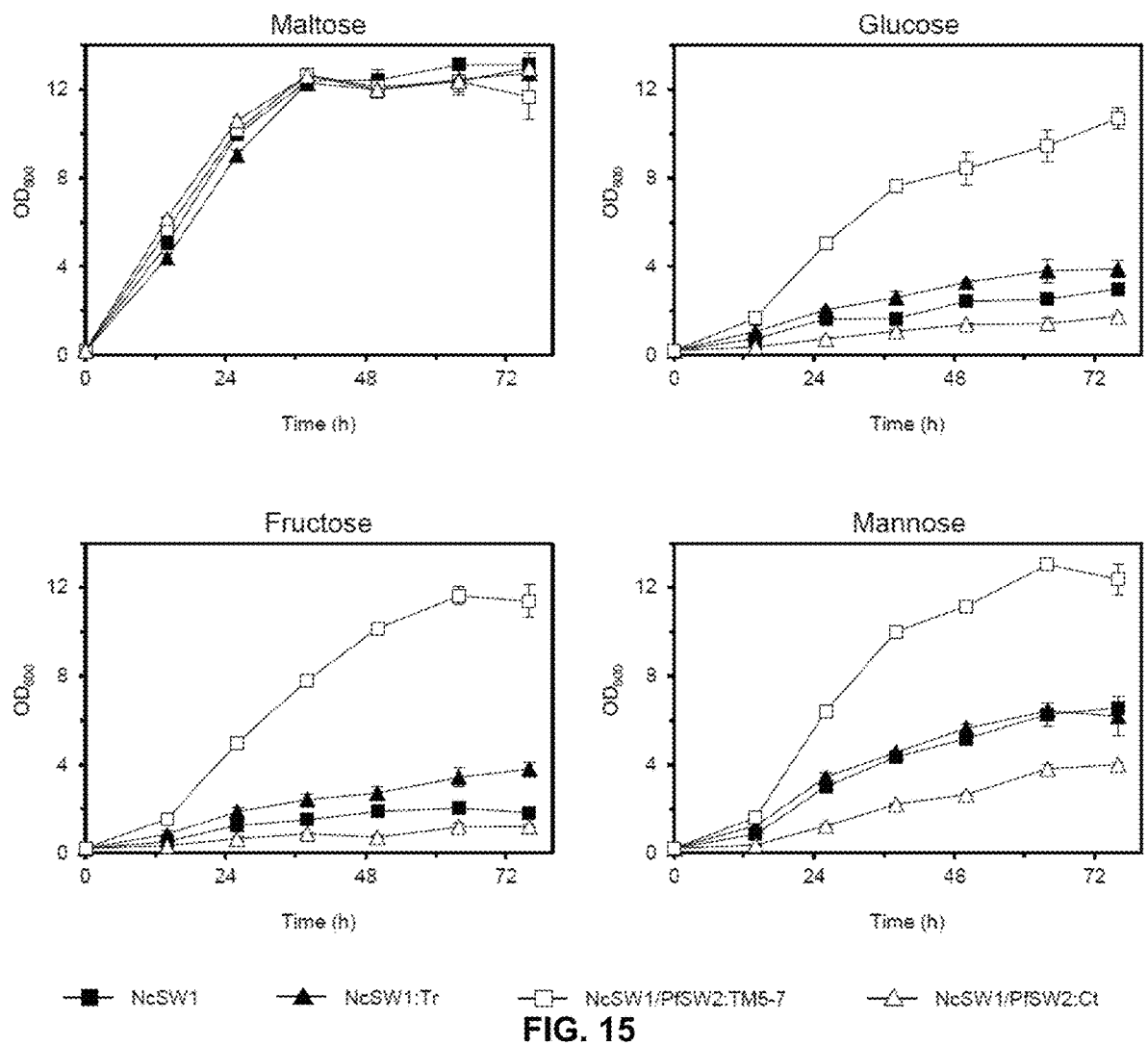
FIG. 15. Growth of NcSWEET1 C-terminal mutants.
Figure 16A:
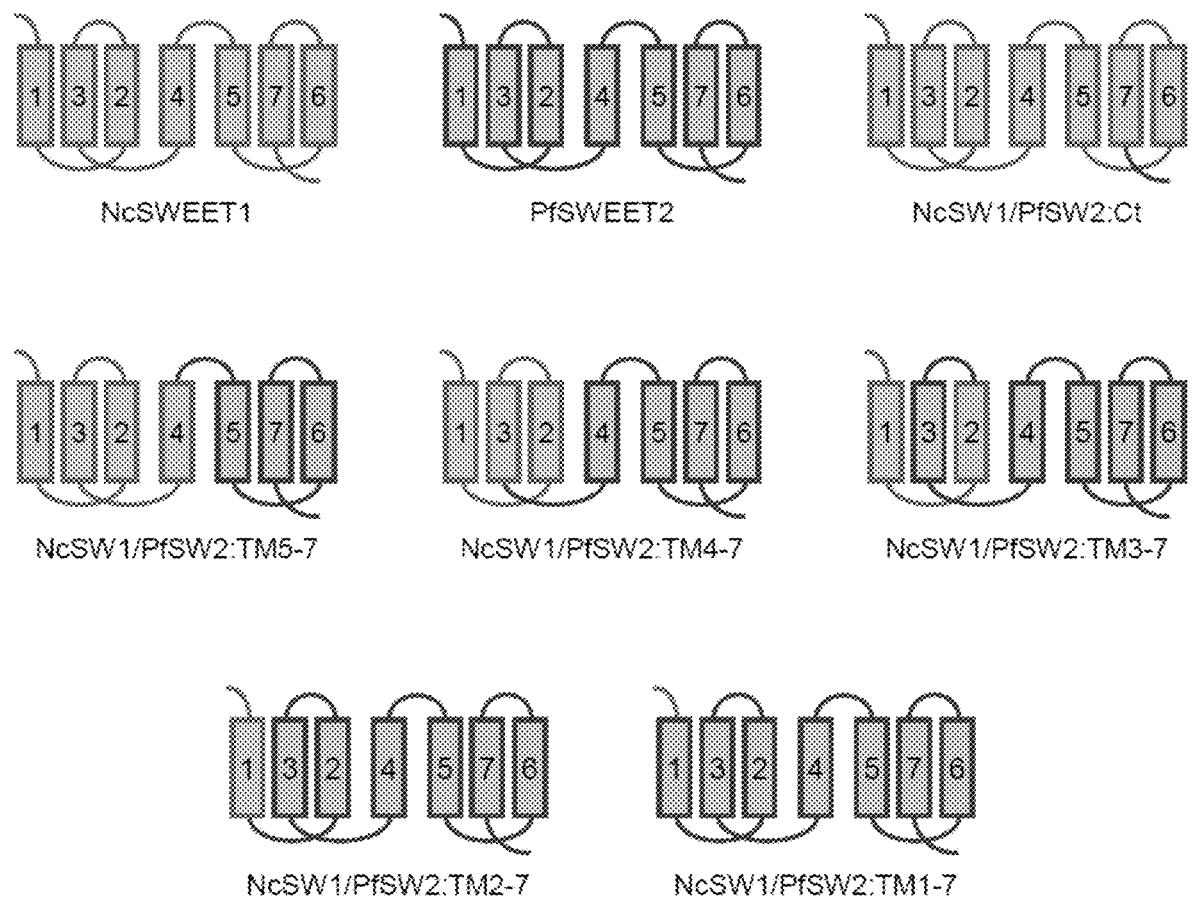
FIG. 16A. Schema of NcSWEET1 and PfSWEET2 chimera constructs. Chimeras formed between NcSWEET1 and PfSWEET2 with varied cross-over junction positions.
Figure 16B:
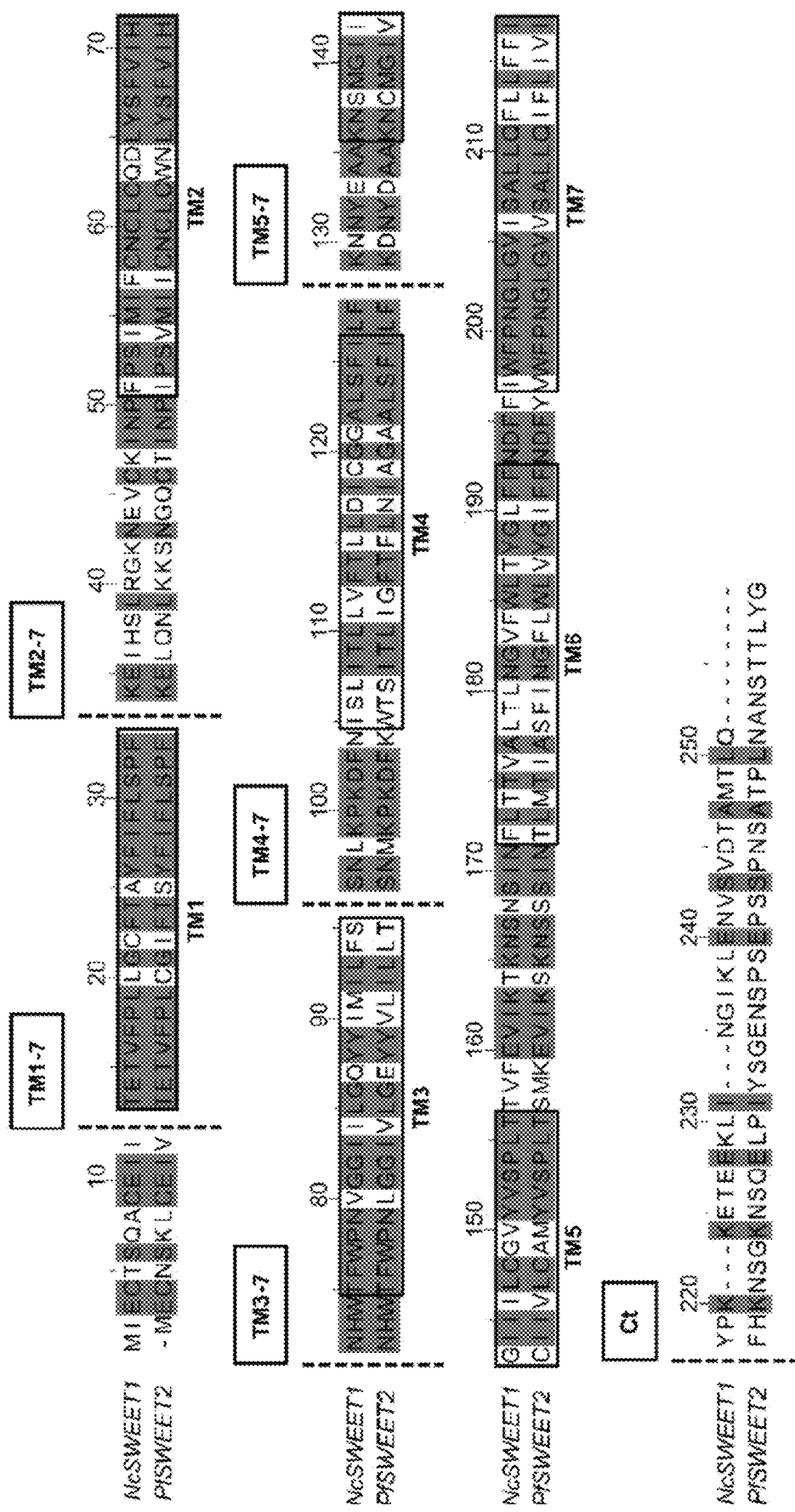
FIG. 16B. Alignment schema of NcSWEET1 and PfSWEET2 chimera sequences. Positions denoted in dark blue are identical in both sequences. Transmembrane domains were annotated according to a consensus TOP-CONS prediction. The amino acid sequence of NcSWEET1 is SEQ ID NO:1. The amino acid sequence of PfSWEET2 is SEQ ID NO:18.
Figure 17:
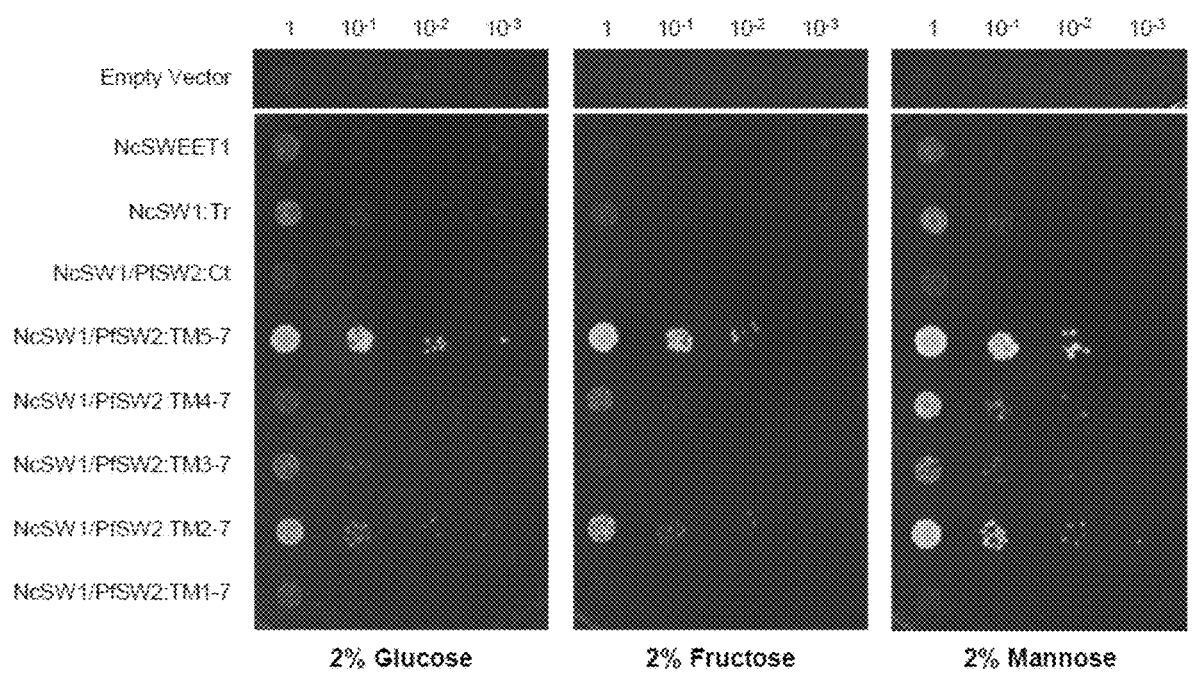
FIG. 17. Spot assay growth of NcSWEET1/PfSWEET2 chimeras. Growth captured after a 4d incubation at 30° C. on SD (-trp) plates supplemented with respective hexose carbon sources.
Figure 18:
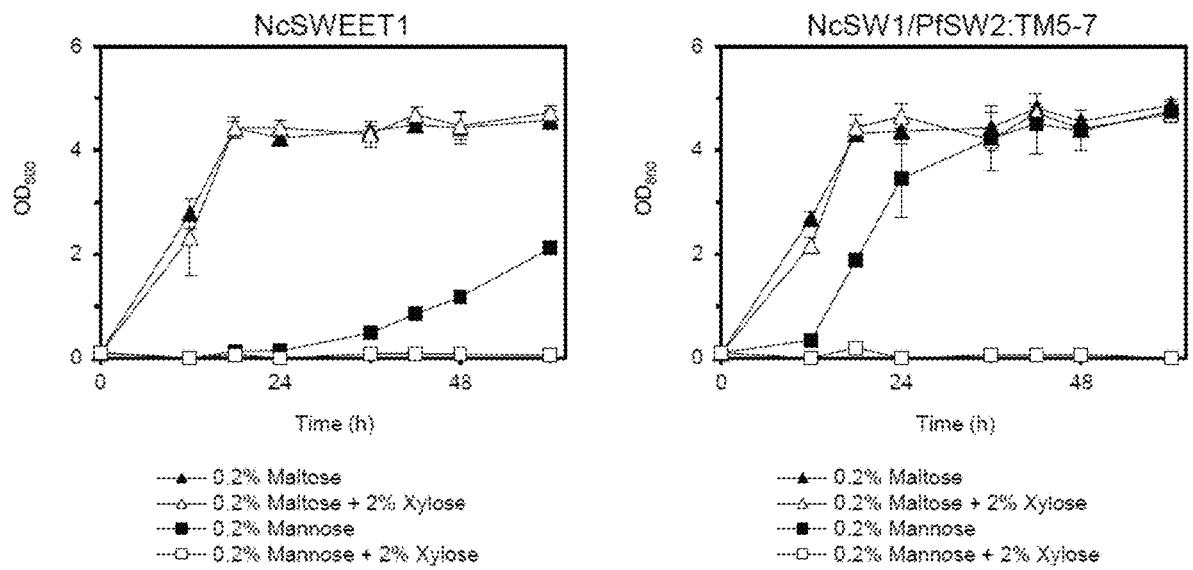
FIG. 18. Xylose inhibition assay of mannose uptake by AGF SWEETs. (a) Evaluation of strain growth mediated by endogenous MAL2/MAL3 (maltose) and AGF SWEETs (mannose) when supplemented with xylose sugar; (b) Growth with increasing xylose dosing.
Figure 18:
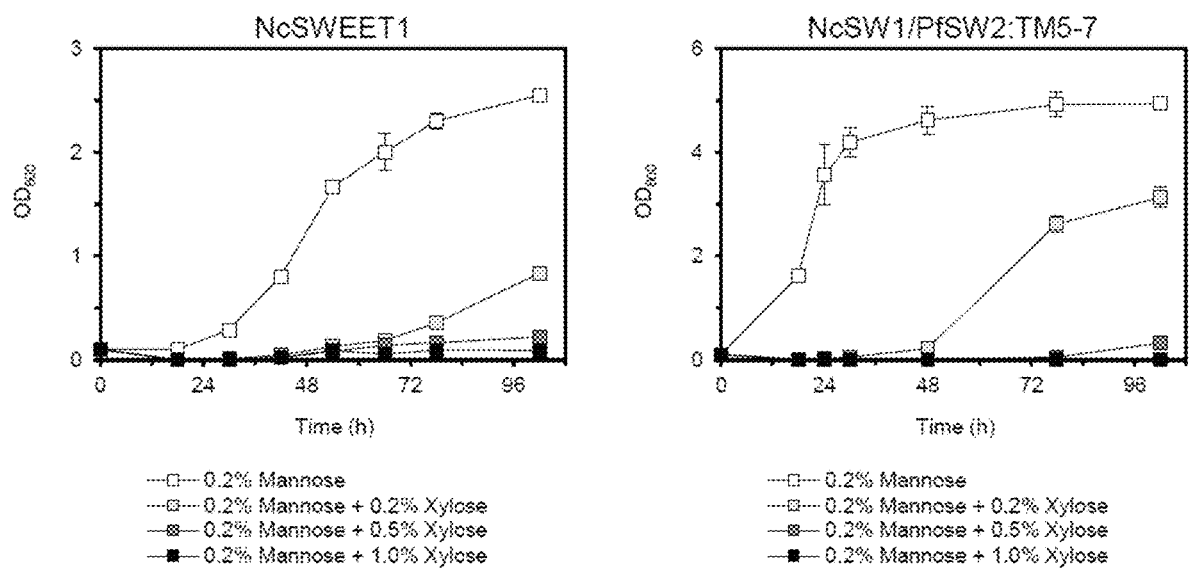
Figure 19:
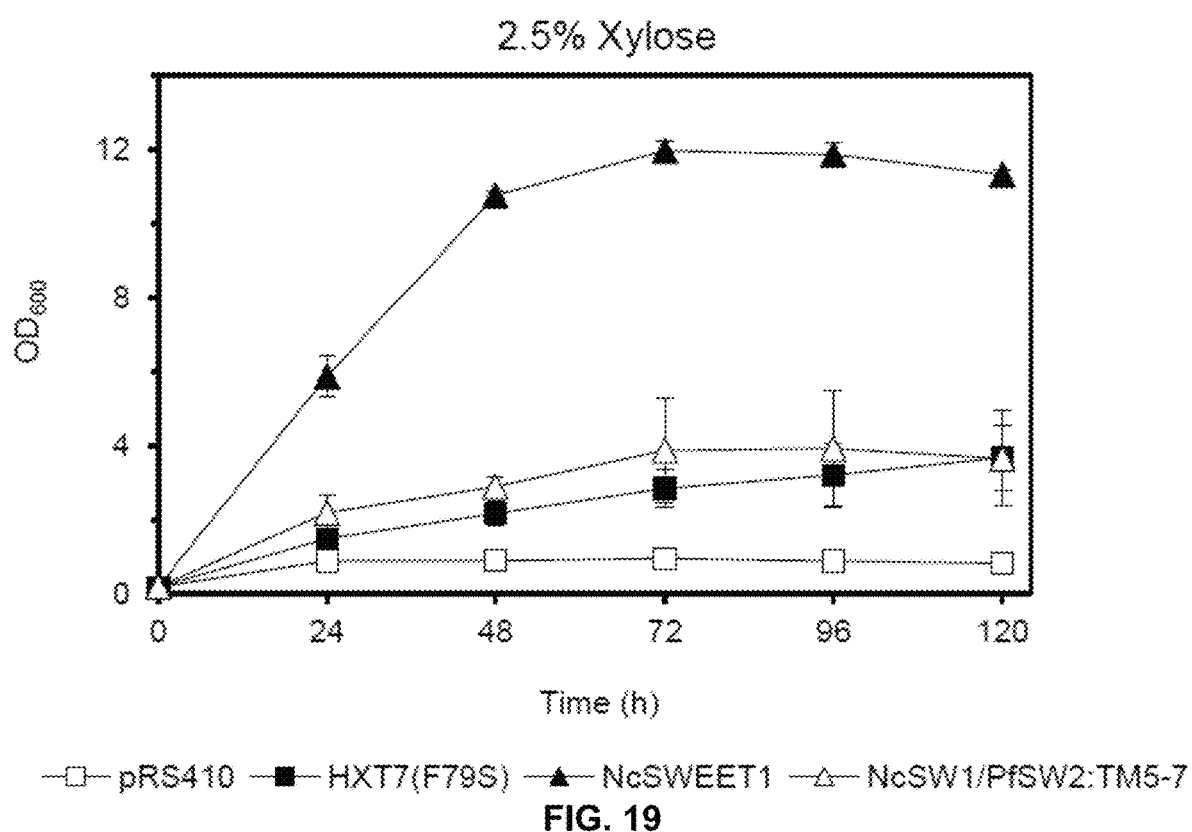
FIG. 19. Growth phenotype of SR8D8 strains on xylose.

Functional conservation of key SWEET residues in NcSWEET1 was probed by targeted mutagenesis. Four positions that correspond to substrate-binding pocket and intracellular gate features in the resolved crystal structure of the *Oryza sativa* SWEET2b (OsSWEET2b) were selected for mutagenesis (41): P52A, P154A, W185G, and N201A. While confocal micrographs revealed an increase in intracellular accumulation of the N201A variant, other mutations negligibly influenced trafficking (Supplementary FIG. 5). Loss-of-function was replicated for P52A and N201A mutants, while P154A and W185G demonstrated a reduction in activity (FIGS. 12 and 13). Plant SWEETs leverage a tetrad of proline residues as a key hinge during conformation changes (41), consistent with complete loss-of-function after mutagenesis in the homolog *Arabidopsis thaliana* SWEET1 (AtSWEET1). While these residues demonstrate high conservation in fungal SWEETs, our results suggest that the hinge may function differently in fungal SWEETs. Similarly, retention of activity by the W185G mutant is of interest given the conserved role of this aromatic residue in binding sugar substrates (16) and its high degree of conservation across all known SWEETs (30). The flexibility of the glycine substitution may enable residue F184 to act as a novel substitute for binding glucose. Further characterization of non-plant SWEETs is necessary to fully understand SWEET functional diversity.

3.4 Sampling AGF SWEET Diversity Using Protein Chimeras

Poor functional production of AGF SWEETs in *S. cerevisiae* motivated the development of alternative approaches to sample and alter functional diversity. Our approach was driven by a previous study conducted by Tao et al. which described a beneficial, single cross-over chimera formed between OsSWEET2b and a close homolog, OsSWEET1a (41). The cross-over position was placed between TM4 and TM5, consistent with observed functional benefit in retaining an association of the N-terminal domain (TM1-3) and TM4 (43). Residues both before and after the cross-over position contribute to the structure of the substrate-binding pocket and intra-, extracellular gates (30, 41), suggesting that such protein chimeras can broadly sample NcSWEET1 sequence space. Further, a leading NcSWEET1 chassis should contribute N-terminal sequence features that support robust trafficking to the ER.

Growth complementation in EBY.VW4000 was used to assay the activity of single cross-over chimeras between NcSWEET1 and other AGF SWEETs on glucose, fructose, and mannose sugars (FIG. 4). NcSW1/ArSW3 and NcSW1/PfSW2 chimeras demonstrated enhanced activity on all substrates; NcSW1/NcSW3 strains had lower growth rates than the wild-type NcSWEET1; all other pairings generated a loss of function. Confocal micrographs of strains expressing functional chimera tagged with eGFP showed negligible signal at the cell periphery, seemingly inconsistent with improved growth rates on hexose sugars (FIG. 14). Significant sequence identity to NcSWEET1 appeared to benefit the retention of transport function, however the fusion to the closest homolog, NcSWEET4, yielded a non-functional chimera. We speculate that the poorly conserved C-terminal tail may be consequential for heterologous expression, yielding observed degrees of production compatibility. Accordingly, a truncated NcSWEET1 variant (NcSW1:Tr) and an additional PfSWEET2 chimera, formed by replacing the tail of NcSWEET1 with the tail of PfSWEET2 (NcSW1/PfSW2:Ct), were assayed (FIG. 15). The Ct chimera demonstrated reduce growth on all substrates, whereas the truncation of the NcSWEET1 C-terminus was beneficial to growth. The poor growth of the Ct variant suggests that residues of the PfSWEET2 tail are unlikely to contribute to the robust phenotype demonstrated by the initial NcSW1/PfSW2 chimera, comprising the four N-terminal transmembrane segments of NcSW1 and the three C-terminal transmembrane segments of PfSW2.

An additional set of four NcSWEET1:PfSWEET2 chimeras, with cross-over positions increasingly closer to the N-terminus of NcSWEET1, were assembled to further sample PfSWEET2 sequence diversity and to identify key residues that govern function. Of particular interest are positions in the primary protein sequence that allow modulation of substrate preference. The corresponding fusions were named TM4-7, TM3-7, TM2-7, and TM1-7, and contain 95, 71, 33, and 12 amino-terminal NcSWEET1 residues, respectively (FIGS. 16A and 16B). Remarkably, all PfSWEET2 chimeras were functionally expressed in EBY.VW4000 and demonstrated differential changes to activity on assayed hexose sugars (FIGS. 5 and 17). Surprisingly, the changes in activity were not continuous across the chimera; construct TM2-7 exhibited a robust phenotype closest to the TM5-7 chimera, whereas TM1-7 only facilitated glucose uptake. Also notable is chimera TM4-7, which demonstrates significant improvement to growth on fructose and mannose relative to glucose. It follows that the residues that differ between NcSWEET1 and PfSWEET2, in the span between the TM5-7 junction and the TM4-7 junction, likely modulate sugar affinities. Yet, these positions are predominantly within the poorly conserved linker TM domain, which is distal to the transport pathway in resolved crystal structures [OsSWEET2b, AtSWEET13] (41, 42). Similarly, the role of the three residues that differ between TM2-7 and TM1-7 that generate significant phenotypic differences, including differential sugar affinities, is poorly understood.

The TM1-7 chimera also revealed the sensitivity of AGF SWEET expression in *S. cerevisiae*, as the wild-type PfSWEET2 that fails to functionally express differs from the TM1-7 chimera by only six amino-terminal residues. A possible culprit is the lysine residue at position 6, as it adds a positive charge to the amino-terminus of PfSWEET2 and also reduces the transmembrane charge differential of TM1, which may influence the relative transmembrane orientation of the protein (46, 47).

3.5 Anaerobic Fungal SWEETs Facilitate Xylose Transport

The functional characterization of SWEETs has revealed diverse substrate preferences for mono-, di-, tri-saccharides, and even plant hormones (18). However, studies have yet to assay the activity of any SWEET towards pentose sugar substrates, i.e., xylose. SWEETs may support low-affinity uptake akin to hexose transport systems in *S. cerevisiae* (48), even though xylose is not a native substrate. In fact, xylose appeared to inhibit AGF SWEET mediated mannose uptake in a dose-dependent manner indicative of competitive inhibition or transport (FIG. 18).

Genes encoding AGF SWEETs were expressed in a xylose-utilizing strain deficient in all native hexose and xylose transporters to validate preliminary evidence of xylose transport through growth complementation. Preliminary evaluation in strain SR8D8 revealed that both NcSWEET1 and the NcSW1/PfSW2:TM5-7 chimera supported growth on 2.5% xylose as the sole carbon source, indicative of xylose transport (FIG. 19).

Observed SWEET activity on xylose motivated the evaluation of glucose/xylose co-utilization by NcSWEET1 and robust PfSWEET2 chimeras. SR8D8 expressing various SWEETs were sub-cultured after growth on glycerol & ethanol into cultures supplemented with both 2.5% w/v glucose and 2.5% w/v xylose. In addition to monitoring culture growth, the consumption of both sugars was simultaneously measured using a YSI bioanalyzer (FIG. 7). SR8D8 expressing wild-type NcSWEET1 demonstrated a robust capacity for xylose utilization and co-consumption with glucose. Remarkably, NcSWEET1 significantly outperformed by the HXT7(F79S) variant. Co-utilization of glucose and xylose was also evident in SR8DR expressing TM5-7 or TM2-7 chimera. SR8D8 expressing TM3-7 chimera exhibited negligible xylose and moderate glucose utilization. SR8D8 expressing TM2-7 chimera demonstrated xylose utilization, unlike the TM3-7 variant, signifying that the three novel positions on TM2 can modulate the affinity for xylose. Diminished xylose utilization by SR8D8 expressing PfSWEET2 chimeras is consistent with the strong preference in PfSWEET2 for solely glucose sugar.

NcSWEET1 demonstrated broad activity on hexose sugars and xylose, which was improved by forming chimeras with other anaerobic fungal SWEETs. The wild-type NcSWEET1 and the best performing chimera derived from it, NcSW1/PfSW2:TM5-7, supported the co-utilization of glucose and xylose sugars. Additional chimeras have identified narrow sets of residues that appear to control substrate specificity. This work demonstrates that as few as three substitutions can toggle between activity solely on glucose or both on hexose sugars and xylose. These results show that anaerobic fungal SWEETs are useful for not only improving xylose uptake but also co-utilization of glucose and xylose in *S. cerevisiae*. We foresee that protein engineering methods can improve the activity of the best performing candidate, wild-type NcSWEET1, on xylose.

TABLE 5

Conservation of residues in fungal SWEETs at the 19 most conserved positions across eukaryotic SWEETs. Alignment to OsSWEET2 putatively assigned positions forming (or proximal to) the substrate-binding pocket and intra-, extra-facial gates.

| Position in AtSWEET1 | Mutated Amino Acids | Mutant Activity | Reference | Position in NcSWEET1 | Eukaryotic SWEETs[a] | Fungal SWEETs |
|---|---|---|---|---|---|---|
| Extracellular Gate[b] | | | | | | |
| Y57 | A | Abolished | (1) | Y66 | 96% (Y) | 98% (Y) |
| G58 | D | Abolished | (2) | S67 | 60% (G) | 57% (G) |
| G131 | D | Abolished | (3) | G140 | 98% (G) | 95% (G) |
| Y179 | A | Reduced | (2) | Y188 | 94% (Y) | 74% (D) |
| D185 | A | Wild-Type | (1) | D194 | 93% (D) | 66% (F) |
| Substrate Binding Pocket[b] | | | | | | |
| S54 | A or C | Wild-Type | (1) | Q63 | 68% (W) | 81% (W) |
| N73 | A | Abolished | (1) | N79 | 96% (N) | 100% (N) |
| W176 | A | Abolished | (1) | W185 | 90% (W) | 100% (W) |
| P191 | T | Abolished | (3) | P200 | 89% (P) | 100% (P) |
| N192 | A | Abolished | (1) | N201 | 96% (N) | 98% (N) |
| Intracellular Gate[b] | | | | | | |
| P23 | A | Abolished | (1) | P18 | 77% (G) | 73% (P) |
| P43 | A | Abolished | (1) | P52 | 97% (P) | 88% (P) |
| Y83 | A | Reduced | (3) | Y89 | 90% (Y) | 61% (Y) |
| F87 | A | Abolished | (3) | M91 | Not Conserved | Not Conserved |
| Y90 | A | Wild-Type | (3) | F94 | 41% (L) | Not Conserved |
| P145 | A | Abolished | (1) | P154 | 97% (P) | 100% (P) |
| K156 | R | Wild-Type | (3) | K165 | 78% (K) | 50% (K) |
| M161 | A | Abolished | (3) | I170 | 83% (M) | Not Conserved |
| P162 | A | Abolished | (1) | N171 | 94% (P) | Not Conserved |
| Q202 | D | Abolished | (3) | Q211 | 96% (Q) | 95% (Q) |

[a] Determined from Clustal Omega sequence alignment using protein sequences detailed in (3).
[b] From alignment to OsSWEET2b (1) and AtSWEET13 (4) sequences with resolved crystal structures
(1) Tao Y, Cheung L S, Li S, Eom J-S, Chen L-Q, et al. 2015. Structure of a eukaryotic SWEET transporter in a homotrimeric complex. Nature. 527(7577): 259-63
(2) Xuan Y H, Hu Y B, Chen L-Q, Sosso D, Ducat D C, et al. 2013. Functional role of oligomerization for bacterial and plant SWEET sugar transporter family. Proc. Natl. Acad. Sci. U.S.A. 110(39): E3685-94
(3) Jia B, Zhu X F, Pu Z J, Duan Y X, Hao L J, et al. 2017. Integrative View of the Diversity and Evolution of SWEET and SemiSWEET Sugar Transporters. Front. Plant Sci. 8: 2178
(4) Han L, Zhu Y, Liu M, Zhou Y, Lu G, et al. 2017. Molecular mechanism of substrate recognition and transport by the AtSWEET13 sugar transporter. Proc. Natl. Acad. Sci. U.S.A. 114(38): 10089-94

CONCLUSIONS

In this work, we produce functional anerobic gut fungal SWEET transporters in *S. cerevisiae* for characterization. To our knowledge, this is the first study to evaluate the utility of SWEETs in engineering *S. cerevisiae* sugar transport. Further, this is the first evaluation of the capacity of SWEETs to facilitate xylose transport. The transporter

REFERENCES CITED HEREIN

1. Sharma N K, Behera S, Arora R, Kumar S, Sani R K. 2018. Xylose transport in yeast for lignocellulosic ethanol production: Current status. *J. Biosci. Bioeng.* 125(3):259-67
2. Lian J, Li Y, HamediRad M, Zhao H. 2014. Directed evolution of a cellodextrin transporter for improved biofuel production under anaerobic conditions in *Saccharomyces cerevisiae*. *Biotechnol. Bioeng.* 111(8): 1521-31

3. Gárdonyi M, Jeppsson M, Lidén G, Gorwa-Grauslund M F, Hahn-Hagerdal B. 2003. Control of xylose consumption by xylose transport in recombinant *Saccharomyces cerevisiae. Biotechnol. Bioeng.* 82(7):818-24

4. Kim S R, Ha S-J, Wei N, Oh E J, Jin Y-S. 2012. Simultaneous co-fermentation of mixed sugars: a promising strategy for producing cellulosic ethanol. *Trends Biotechnol.* 30(5):274-82

5. Jeffries T W. 1983. Utilization of xylose by bacteria, yeasts, and fungi. In *Pentoses and Lignin*, pp. 1-32. Berlin/Heidelberg: Springer-Verlag 6. Eliasson A, Christensson C, Wahlbom C F, Hahn-Hagerdal B. 2000. Anaerobic xylose fermentation by recombinant *Saccharomyces cerevisiae* carrying XYL1, XYL2, and XKS1 in mineral medium chemostat cultures. *Appl. Environ. Microbiol.* 66(8):3381-86

7. Kim B, Du J, Eriksen D T, Zhao H. 2013. Combinatorial design of a highly efficient xylose-utilizing pathway in *Saccharomyces cerevisiae* for the production of cellulosic biofuels. *Appl. Environ. Microbiol.* 79(3):931-41

8. Shen Y, Chen X, Peng B, Chen L, Hou J, Bao X. 2012. An efficient xylose-fermenting recombinant *Saccharomyces cerevisiae* strain obtained through adaptive evolution and its global transcription profile. *Appl. Microbiol. Biotechnol.* 96(4): 1079-91

9. Young E, Poucher A, corner A, Bailey A, Alper H. 2011. Functional survey for heterologous sugar transport proteins, using *Saccharomyces cerevisiae* as a host. *Appl. Environ. Microbiol.* 77(10):3311-19

10. Moysés D N, Reis V C B, de Almeida J R M, de Moraes L M P, Torres F A G. 2016. Xylose Fermentation by *Saccharomyces cerevisiae*: Challenges and Prospects. *Int. J. Mol. Sci.* 17(3):207

11. Hou J, Qiu C, Shen Y, Li H, Bao X. 2017. Engineering of *Saccharomyces cerevisiae* for the efficient co-utilization of glucose and xylose. *FEMS Yeast Res.* 17(4):

12. Seppälä S, Solomon K V., Gilmore S P, Henske J K, O'Malley M A. 2016. Mapping the membrane proteome of anaerobic gut fungi identifies a wealth of carbohydrate binding proteins and transporters. *Microb. Cell Fact.* 15(1):212

13. Seppala S, Yoo J I, Yur D, O'Malley M A. 2019. Heterologous transporters from anaerobic fungi bolster fluoride tolerance in *Saccharomyces cerevisiae. Metab. Eng. Commun.* 9:e00091

14. Yoo J I, Seppälä S, O'Malley M A. 2020. Engineered fluoride sensitivity enables biocontainment and selection of genetically-modified yeasts. *Nat. Commun.*

15. Flint H J. 1997. The rumen microbial ecosystem—some recent developments. *Trends Microbiol.* 5(12):483-88

16. Theodorou M K, Mennim G, Davies D R, Zhu W-Y, Trinci A P J, Brookman J L. 1996. Anaerobic fungi in the digestive tract of mammalian herbivores and their potential for exploitation. *Proc. Nutr. Soc.* 55(03):913-26

17. Henske J K, Gilmore S P, Haitjema C H, Solomon K V., O'Malley M A. 2018. Biomass-degrading Enzymes are Catabolite Repressed in Anaerobic Gut Fungi. *AIChE J.* 00(0):1-8

18. Jeena G S, Kumar S, Shukla R K. 2019. Structure, evolution and diverse physiological roles of SWEET sugar transporters in plants. *Plant Mol. Biol.* 100(4-5):351-65

19. Solomon K V., Haitjema C H, Henske J K, Gilmore S P, Borges-Rivera D, et al. 2016. Early-branching gut fungi possess a large, comprehensive array of biomass-degrading enzymes. *Science* (80-.). 351(6278):1192-96

20. El-Gebali S, Mistry J, Bateman A, Eddy S R, Luciani A, et al. 2018. The Pfam protein families database in 2019. *Nucleic Acids Res.* 47:427-32

21. Finn R D, Clements J, Eddy S R. HMMER web server: interactive sequence similarity searching 22. Chen L-Q, Hou B-H, Lalonde S, Takanaga H, Hartung M L, et al. 2010. Sugar transporters for intercellular exchange and nutrition of pathogens. *Nature.* 468(7323):527-32

23. Grigoriev I V, Nikitin R, Haridas S, Kuo A, Ohm R, et al. 2014. MycoCosm portal: gearing up for 1000 fungal genomes. *Nucleic Acids Res.* 42 (Database issue):D699-704

24. Tsirigos K D, Peters C, Shu N, Kall L, Elofsson A. 2015. The TOPCONS web server for consensus prediction of membrane protein topology and signal peptides. *Nucleic Acids Res.* 43(W1):W401-7

25. Fu L, Niu B, Zhu Z, Wu S, Li W. 2012. CD-HIT: Accelerated for clustering the next-generation sequencing data. *Bioinformatics.* 28(23):3150-52

26. Sievers F, Wilm A, Dineen D, Gibson T J, Karplus K, et al. 2014. Fast, scalable generation of high-quality protein multiple sequence alignments using Clustal Omega. *Mol. Syst. Biol.* 7(1):539-539

27. Stamatakis A. 2014. RAxML version 8: a tool for phylogenetic analysis and post-analysis of large phylogenies. *Bioinformatics.* 30(9): 1312-13

28. Miller M A, Pfeiffer W, Schwartz T. 2010. Creating the CIPRES Science Gateway for inference of large phylogenetic trees 29. Kumar S, Stecher G, Tamura K. 2016. MEGA7: Molecular Evolutionary Genetics Analysis Version 7.0 for Bigger Datasets. *Mol. Biol. Evol.* 33(7):1870-74

30. Jia B, Zhu X F, Pu Z J, Duan Y X, Hao L J, et al. 2017. Integrative View of the Diversity and Evolution of SWEET and SemiSWEET Sugar Transporters. *Front. Plant Sci.* 8:2178

31. Wieczorke R, Krampe S, Weierstall T, Freidel K, Hollenberg C P, Boles E. 1999. Concurrent knock-out of at least 20 transporter genes is required to block uptake of hexoses in *Saccharomyces cerevisiae. FEBS Lett.* 464(3):123-28

32. Kim S R, Skerker J M, Kang W, Lesmana A, Wei N, et al. 2013. Rational and Evolutionary Engineering Approaches Uncover a Small Set of Genetic Changes Efficient for Rapid Xylose Fermentation in *Saccharomyces cerevisiae. PLoS One.* 8(2):e57048

33. Xu H. 2015. ENGINEERING *SACCHAROMYCES CEREVISIAE* FOR CELLULOSIC ETHANOL PRODUCTION. University of Illinois at Urbana-Champaign. 1-87 pp.

34. Reider Apel A, Ouellet M, Szmidt-Middleton H, Keasling J D, Mukhopadhyay A. 2016. Evolved hexose transporter enhances xylose uptake and glucose/xylose co-utilization in *Saccharomyces cerevisiae. Sci. Rep.* 6(1):19512

35. Gietz R D, Woods R A. 2002. Transformation of yeast by lithium acetate/single-stranded carrier DNA/polyethylene glycol method. *Methods Enzymol.* 350:87-96

36. Nørholm MEM. 2010. A mutant Pfu DNA polymerase designed for advanced uracil-excision DNA engineering. *BMC Biotechnol.* 10(1):21

37. Cavaleiro A M, Kim S H, Seppala S, Nielsen M T, Norholm M H H. 2015. Accurate DNA Assembly and Genome Engineering with Optimized Uracil Excision Cloning. *ACS Synth. Biol.* 4(9): 1042-46

38. Solomon K V, Haitjema C H, Henske J K, Gilmore S P, Borges-Rivera D, et al. 2016. Early-branching gut fungi possess a large, comprehensive array of biomass-degrading enzymes. *Science* (80-.). 351(6278): 1192-95
39. Henske J K, Gilmore S P, Knop D, Cunningham F J, Sexton J A, et al. 2017. Transcriptomic characterization of *Caecomyces churrovis*: A novel, non-rhizoid-forming lignocellulolytic anaerobic fungus. *Biotechnol. Biofuels.* 10(1):1-12
40. Hu Y-B, Sosso D, Qu X-Q, Chen L-Q, Ma L, et al. 2016. Phylogenetic evidence for a fusion of archaeal and bacterial SemiSWEETs to form eukaryotic SWEETs and identification of SWEET hexose transporters in the amphibian chytrid pathogen Batrachochytrium dendrobatidis. *FASEB J.*
41. Tao Y, Cheung L S, Li S, Eom J-S, Chen L-Q, et al. 2015. Structure of a eukaryotic SWEET transporter in a homotrimeric complex. *Nature.* 527(7577):259-63
42. Han L, Zhu Y, Liu M, Zhou Y, Lu G, et al. 2017. Molecular mechanism of substrate recognition and transport by the AtSWEET13 sugar transporter. *Proc. Natl. Acad. Sci. U.S.A* 114(38): 10089-94
43. Xuan Y H, Hu Y B, Chen L-Q, Sosso D, Ducat D C, et al. 2013. Functional role of oligomerization for bacterial and plant SWEET sugar transporter family. *Proc. Natl. Acad. Sci.* U.S.A 110(39):E3685-94
44. Chorev M, Carmel L. 2012. The Function of Introns. *Front. Genet.* 3:55
45. Haitjema C H, Gilmore S P, Henske J K, Solomon K V., de Groot R, et al. 2017. A parts list for fungal cellulosomes revealed by comparative genomics. *Nat. Microbiol.* 2(8):17087
46. Wallin E, von Heijne G. 1998. Genome-wide analysis of integral membrane proteins from eubacterial, archaean, and eukaryotic organisms. *Protein Sci.* 7(4):1029-38
47. Harley C A, Holt J A, Turner R, Tipper D J. 1998. Transmembrane protein insertion orientation in yeast depends on the charge difference across transmembrane segments, their total hydrophobicity, and its distribution. *J. Biol. Chem.* 273(38):24963-71
48. Hamacher T, Boles E, Gardonyi M, Hahn-Hagerdal B, Becker J. 2002. Characterization of the xylose-transporting properties of yeast hexose transporters and their influence on xylose utilization. *Microbiology.* 148(9): 2783-88

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A hybrid sugar transporter having an altered sugar transporter activity and comprising an amino acid sequence having the following structure:

| NT | TMD1 | J1 | TMD2 | J2 | **** | TMDn | CT |;

wherein NT is a N-terminal domain, TMD1 is a first transmembrane domain (TMD), J1 is a first junction domain, the dotted line represents further TMDx and Jx pairs wherein x is an integer and is less than n, TMDn is the nth TMD, CT is a C-terminal domain, n is 7 to 9, wherein at least one TMD is from a first sugar transporter and a second TMD is from a second sugar transporter, wherein the first sugar transporter and the second sugar transporter are heterologous to each other; wherein (a) the altered sugar transporter activity is the increased or enhanced activity for transporting a pentose; (b) NT is about 3 to 20 amino acid residues in length, each TMD is about 19 or 22 amino acid residues in length, each J is about 3 to 25 amino acid residues in length, CT is about 10 to 70 amino acid residues in length; and (c) each TMD is a TMD of AmSWEET1, AmSWEET2, AmSWEET3, AmSWEET4, AmSWEET5, AmSWEET6, ArSWEET1, ArSWEET2, ArSWEET3, BbSWEET1, BbSWEET2, BdSWEET1, BdSWEET2, CaSWEET1, CaSWEET2, CaSWEET3, CcSWEET1, CcSWEET2, ChSWEET1, ChSWEET2, ChSWEET3, ClSWEET1, CmSWEET1, CpSWEET1, CspSWEET1, CsSWEET1, DcSWEET1, EhSWEET1, EhSWEET2, EhSWEET3, EhSWEET4, GhSWEET1, GhSWEET2, GhSWEET3, GppSWEET1, GppSWEET2, GppSWEET3, GprSWEET1, GprSWEET2, GprSWEET3, HcSWEET1, HcSWEET2, HcSWEET3, HcSWEET4, HcSWEET5, HpSWEET1, HpSWEET2, JspSWEET1, KaSWEET1, NcSWEET1, NcSWEET1A, NcSWEET1B, NcSWEET1C, NcSWEET1D, NcSWEET2, NcSWEET3, NcSWEET4, NcSWEET5, OmSWEET1, OmSWEET2, PfSWEET1, PfSWEET2, PgSWEET1, PspSWEET1, PsSWEET1, PsSWEET2, RaSWEET1, RbSWEET1, RgSWEET1, RgSWEET2, or RgSWEET3.

2. The hybrid sugar transporter of claim 1, wherein each TMD is a TMD of a sugar transporter of *Neocallimastix californiae, Anaeromyces robustus,* or *Piromyces finnis*.

3. A nucleic acid molecule comprising an open reading frame (ORF) encoding the hybrid sugar transporter of claim 1.

4. A vector comprising the nucleic acid of claim 3.

5. An isolated host cell comprising the vector of claim 4.

6. A method for constructing the vector of claim 4, the method comprising: introducing the ORF encoding the hybrid sugar transporter into a vector to produce the vector encoding the hybrid sugar transporter.

7. A method for producing the hybrid sugar transporter, the method comprising: (a) providing the vector of claim 4, (b) introducing the vector into an isolated host cell, and (c) culturing or growing the host cell in a culture medium such that the host cell expresses the hybrid sugar transporter and the host cell has an altered capability for transporting sugar into the host cell.

8. The hybrid sugar transporter of claim 1, wherein n=7.

9. The hybrid sugar transporter of claim 1, wherein TMD1, TMD2, TMD3, or TMD4 are SEQ ID NO: 3, SEQ ID NO: 4, SEQ ID NO: 5, or SEQ ID NO: 6, respectively.

10. The hybrid sugar transporter of claim 9, wherein TMD1, TMD2, TMD3, or TMD4 are TMD1, TMD2, TMD3, or TMD4, respectively, of *Neocallimastix californiae* SWEET1.

11. The hybrid sugar transporter of claim 1, wherein TMD5, TMD6, or TMD7 are TMD5, TMD6, or TMD7, respectively, of *Piromyces finnis* SWEET2.

12. The hybrid sugar transporter of claim 9, wherein n=7; TMD1, TMD2, TMD3, and TMD4 are TMD1, TMD2, TMD3, and TMD4, respectively, of *Neocallimastix californiae* SWEET1; and TMD5, TMD6, and TMD7 are TMD5, TMD6, and TMD7, respectively, of *Piromyces finnis* SWEET2.

13. The hybrid sugar transporter of claim 1, wherein the NT comprises SEQ ID NO:2.

14. The hybrid sugar transporter of claim 1, wherein the CT comprises SEQ ID NO: 16 or SEQ ID NO: 17.

15. The hybrid sugar transporter of claim 1, wherein at least one TMD is from NcSWEET1 and a second TMD is from a second sugar transporter heterologous to NcSWEET1.

\* \* \* \* \*

SEQUENCE LISTING

<160> NUMBER OF SEQ ID NOS: 74

<210> SEQ ID NO 1
<211> LENGTH: 245
<212> TYPE: PRT
<213> ORGANISM: Neocallimastix californiae

<400> SEQUENCE: 1

```
Met Ile Glu Cys Thr Ser Gln Ala Cys Glu Ile Ile Thr Glu Thr Val
1               5                   10                  15

Phe Pro Leu Leu Gly Cys Phe Thr Ala Tyr Phe Ile Phe Leu Ser Pro
            20                  25                  30

Phe Lys Glu Ile His Ser Leu Arg Gly Lys Asn Glu Val Cys Lys Thr
        35                  40                  45

Asn Pro Phe Pro Ser Ile Met Ile Phe Cys Asn Cys Leu Cys Gln Asp
    50                  55                  60

Leu Tyr Ser Phe Val Ile His Asn His Trp Thr Phe Trp Pro Asn Val
65                  70                  75                  80

Gly Gly Ile Ile Leu Gly Gln Tyr Tyr Ile Met Ile Leu Phe Ser Ser
                85                  90                  95

Asn Leu Lys Pro Lys Asp Phe Asn Ile Ser Leu Ile Thr Leu Leu Val
            100                 105                 110

Phe Thr Leu Leu Asp Ile Cys Gly Gly Ala Leu Ser Phe Ile Leu Phe
        115                 120                 125

Lys Asn Asn Tyr Glu Ala Ala Lys Asn Ser Met Gly Ile Ile Gly Ile
    130                 135                 140
```

-continued

Ile Ile Leu Cys Gly Val Tyr Val Ser Pro Leu Thr Thr Val Phe Glu
145                 150                 155                 160

Val Ile Lys Thr Lys Asn Ser Asn Ser Ile Asn Phe Leu Thr Thr Val
                165                 170                 175

Ala Leu Thr Leu Asn Gly Val Phe Trp Leu Thr Tyr Gly Leu Phe Phe
            180                 185                 190

Asn Asp Phe Phe Ile Trp Phe Pro Asn Gly Leu Gly Val Ile Ser Ala
        195                 200                 205

Leu Leu Gln Phe Leu Leu Phe Phe Ile Tyr Pro Lys Lys Glu Thr Glu
    210                 215                 220

Glu Lys Leu Ile Asn Gly Ile Lys Leu Glu Asn Val Ser Val Asp Thr
225                 230                 235                 240

Ala Met Thr Leu Gln
                245

<210> SEQ ID NO 2
<211> LENGTH: 9
<212> TYPE: PRT
<213> ORGANISM: Neocallimastix californiae
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 2

Glu Cys Xaa Ser Xaa Xaa Cys Glu Ile
1               5

<210> SEQ ID NO 3
<211> LENGTH: 21
<212> TYPE: PRT
<213> ORGANISM: Neocallimastix californiae
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 3

Thr Glu Thr Val Phe Pro Leu Xaa Gly Xaa Phe Thr Xaa Tyr Phe Ile
1               5                   10                  15

Phe Leu Ser Pro Phe
            20

<210> SEQ ID NO 4
<211> LENGTH: 20
<212> TYPE: PRT
<213> ORGANISM: Neocallimastix californiae
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

```
<220> FEATURE:
<221> NAME/KEY: misc_feature
<222> LOCATION: (12)..(13)
<223> OTHER INFORMATION: Xaa can be any naturally occurring amino acid

<400> SEQUENCE: 4

Pro Ser Xaa Met Ile Xaa Cys Asn Cys Leu Cys Xaa Xaa Leu Tyr Ser
1               5                   10                  15

Phe Val Leu His
            20

<210> SEQ ID NO 5
<211> LENGTH: 19
<212> TYPE: PRT
<213> ORGANISM: Neocallimastix californiae
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 5

Thr Phe Trp Pro Asn Xaa Gly Gly Ile Xaa Leu Gly Xaa Tyr Tyr Xaa
1               5                   10                  15

Xaa Ile Leu

<210> SEQ ID NO 6
<211> LENGTH: 19
<212> TYPE: PRT
<213> ORGANISM: Neocallimastix californiae
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 6

Ile Thr Leu Xaa Xaa Phe Thr Xaa Leu Xaa Ile Xaa Gly Xaa Ala Leu
1               5                   10                  15

Ser Phe Ile

<210> SEQ ID NO 7
<211> LENGTH: 21
<212> TYPE: PRT
```

```
<213> ORGANISM: Neocallimastix californiae
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 7

Lys Asn Xaa Met Gly Ile Xaa Xaa Ile Ile Xaa Leu Cys Xaa Xaa Tyr
1               5                   10                  15

Val Ser Pro Leu Thr
            20

<210> SEQ ID NO 8
<211> LENGTH: 20
<212> TYPE: PRT
<213> ORGANISM: Neocallimastix californiae
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 8

Leu Xaa Thr Xaa Ala Xaa Xaa Xaa Asn Gly Xaa Xaa Trp Leu Xaa Tyr
1               5                   10                  15

Gly Xaa Phe Phe
            20

<210> SEQ ID NO 9
<211> LENGTH: 20
<212> TYPE: PRT
<213> ORGANISM: Neocallimastix californiae
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
```

```
<222> LOCATION: (18)..(19)
<223> OTHER INFORMATION: Xaa can be any naturally occurring amino acid

<400> SEQUENCE: 9

Trp Phe Pro Asn Gly Leu Gly Val Xaa Ser Ala Leu Leu Gln Xaa Xaa
1               5                   10                  15

Leu Xaa Xaa Ile
            20

<210> SEQ ID NO 10
<211> LENGTH: 17
<212> TYPE: PRT
<213> ORGANISM: Neocallimastix californiae
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 10

Lys Glu Xaa Xaa Xaa Leu Xaa Xaa Xaa Asn Xaa Xaa Cys Xaa Ile Asn
1               5                   10                  15

Pro

<210> SEQ ID NO 11
<211> LENGTH: 41
<212> TYPE: DNA
<213> ORGANISM: Artificial Sequence
<220> FEATURE:
<223> OTHER INFORMATION: Primer MFA SalI, Rev

<400> SEQUENCE: 11
catagtcgac aattctctta ggattcgatt cacattcatc t                41

<210> SEQ ID NO 12
<211> LENGTH: 8
<212> TYPE: PRT
<213> ORGANISM: Neocallimastix californiae
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Ser Asn Xaa Lys Pro Lys Asp Phe
1               5

<210> SEQ ID NO 13
<211> LENGTH: 7
<212> TYPE: PRT
<213> ORGANISM: Neocallimastix californiae
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
```

<223> OTHER INFORMATION: Xaa can be any naturally occurring amino acid

<400> SEQUENCE: 13

Lys Xaa Asn Tyr Xaa Ala Ala
1               5

<210> SEQ ID NO 14
<211> LENGTH: 12
<212> TYPE: PRT
<213> ORGANISM: Neocallimastix californiae
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 14

Glu Val Ile Lys Xaa Lys Asn Ser Xaa Ser Ile Asn
1               5                   10

<210> SEQ ID NO 15
<211> LENGTH: 35
<212> TYPE: DNA
<213> ORGANISM: Artificial Sequence
<220> FEATURE:
<223> OTHER INFORMATION: Primer TEF1p, BamHI, Fwd

<400> SEQUENCE: 15
cataggatcc agatctgttt agcttgcctc gtccc                                35

<210> SEQ ID NO 16
<211> LENGTH: 8
<212> TYPE: PRT
<213> ORGANISM: Neocallimastix californiae
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 16

Lys Xaa Xaa Xaa Glu Xaa Xaa Ile
1               5

<210> SEQ ID NO 17
<211> LENGTH: 11
<212> TYPE: PRT
<213> ORGANISM: Neocallimastix californiae
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 17

Glu Xaa Xaa Ser Xaa Xaa Xaa Ala Xaa Xaa Leu
1               5                   10

<210> SEQ ID NO 18
<211> LENGTH: 257
<212> TYPE: PRT
<213> ORGANISM: Piromyces finnis

<400> SEQUENCE: 18

Met Glu Cys Asn Ser Lys Leu Cys Glu Ile Val Thr Glu Val Phe Pro
1               5                   10                  15

Leu Cys Gly Ile Phe Thr Ser Tyr Ile Phe Leu Ser Pro Phe Lys
            20                  25                  30

Glu Leu Gln Asn Leu Lys Lys Ser Asn Gly Gln Cys Thr Ile Asn Pro
            35                  40                  45

Ile Pro Ser Val Val Ile Ile Cys Asn Cys Leu Cys Trp Asn Leu Tyr
50                  55                  60

Ser Phe Val Ile His Asn His Trp Thr Phe Trp Pro Asn Leu Gly Gly
65                  70                  75                  80

Ile Val Leu Gly Glu Tyr Tyr Val Leu Ile Leu Leu Thr Ser Asn Met
                85                  90                  95

Lys Pro Lys Asp Phe Lys Trp Thr Ser Ile Thr Leu Ile Gly Phe Thr
            100                 105                 110

Phe Leu Asn Ile Ala Gly Ala Ala Leu Ser Phe Ile Leu Phe Lys Asp
            115                 120                 125

Asn Tyr Asp Ala Ala Lys Asn Cys Met Gly Ile Val Cys Ile Ile Val
        130                 135                 140

Leu Cys Ala Met Tyr Val Ser Pro Leu Thr Ser Met Lys Glu Val Ile
145                 150                 155                 160

Lys Ser Lys Asn Ser Ser Ser Ile Asn Thr Leu Met Thr Ile Ala Ser
                165                 170                 175

Phe Ile Asn Gly Phe Leu Trp Leu Val Tyr Gly Ile Phe Phe Asn Asp
            180                 185                 190

Phe Tyr Val Trp Phe Pro Asn Gly Leu Gly Val Val Ser Ala Leu Leu
            195                 200                 205

Gln Ile Phe Leu Ile Val Ile Phe His Lys Asn Ser Gly Lys Asn Ser
        210                 215                 220

Gln Glu Leu Pro Ile Tyr Ser Gly Glu Asn Ser Pro Ser Glu Pro Ser
225                 230                 235                 240

Ser Pro Asn Ser Ala Thr Pro Leu Asn Ala Asn Ser Thr Thr Leu Tyr
                245                 250                 255

Gly

<210> SEQ ID NO 19
<211> LENGTH: 246
<212> TYPE: PRT
<213> ORGANISM: Arabidopsis thaliana

<400> SEQUENCE: 19

Met Asn Ile Ala His Thr Ile Phe Gly Val Phe Gly Asn Ala Thr Ala
1               5                   10                  15

Leu Phe Leu Phe Leu Ala Pro Ser Ile Thr Lys Arg Ile Ile Lys Asn
            20                  25                  30

Lys Ser Thr Glu Gln Phe Ser Gly Ile Pro Tyr Pro Met Thr Leu Leu
            35                  40                  45

Asn Cys Leu Leu Ser Ala Trp Tyr Gly Leu Pro Phe Val Ser Lys Asp
50                  55                  60

```
Asn Thr Leu Val Ser Thr Ile Asn Gly Thr Gly Ala Val Ile Glu Thr
 65                  70                  75                  80

Val Tyr Val Leu Ile Phe Leu Phe Tyr Ala Pro Lys Lys Glu Lys Ile
                 85                  90                  95

Lys Ile Phe Gly Ile Phe Ser Cys Val Leu Ala Val Phe Ala Thr Val
            100                 105                 110

Ala Leu Val Ser Leu Phe Ala Leu Gln Cys Asn Gly Arg Lys Leu Phe
        115                 120                 125

Cys Gly Leu Ala Ala Thr Val Phe Ser Ile Ile Met Tyr Ala Ser Pro
    130                 135                 140

Leu Ser Ile Met Arg Leu Val Val Lys Thr Lys Ser Val Glu Phe Met
145                 150                 155                 160

Pro Phe Phe Leu Ser Leu Phe Val Phe Leu Cys Gly Thr Ser Trp Phe
                165                 170                 175

Val Tyr Gly Leu Ile Gly Arg Asp Pro Phe Val Ala Ile Pro Asn Gly
            180                 185                 190

Phe Gly Cys Ala Leu Gly Thr Leu Gln Leu Ile Leu Tyr Phe Ile Tyr
        195                 200                 205

Cys Gly Asn Lys Gly Glu Lys Ser Ala Asp Ala Gln Lys Asp Glu Lys
    210                 215                 220

Ser Val Glu Met Lys Asp Asp Glu Lys Lys Gln Asn Val Val Asn Gly
225                 230                 235                 240

Lys Gln Asp Leu Gln Val
                245

<210> SEQ ID NO 20
<211> LENGTH: 230
<212> TYPE: PRT
<213> ORGANISM: Oryza sativa

<400> SEQUENCE: 20

Met Asp Ser Leu Tyr Asp Ile Ser Cys Phe Ala Ala Gly Leu Ala Gly
  1               5                  10                  15

Asn Ile Phe Ala Leu Ala Leu Phe Leu Ser Pro Val Thr Thr Phe Lys
                 20                  25                  30

Arg Ile Leu Lys Ala Lys Ser Thr Glu Arg Phe Asp Gly Leu Pro Tyr
             35                  40                  45

Leu Phe Ser Leu Leu Asn Cys Leu Ile Cys Leu Trp Tyr Gly Leu Pro
         50                  55                  60

Trp Val Ala Asp Gly Arg Leu Leu Val Ala Thr Val Asn Gly Ile Gly
 65                  70                  75                  80

Ala Val Phe Gln Leu Ala Tyr Ile Cys Leu Phe Ile Phe Tyr Ala Asp
                 85                  90                  95

Ser Arg Lys Thr Arg Met Lys Ile Ile Gly Leu Leu Val Leu Val Val
            100                 105                 110

Cys Gly Phe Ala Leu Val Ser His Ala Ser Val Phe Phe Phe Asp Gln
        115                 120                 125

Pro Leu Arg Gln Gln Phe Val Gly Ala Val Ser Met Ala Ser Leu Ile
    130                 135                 140

Ser Met Phe Ala Ser Pro Leu Ala Val Met Gly Val Val Ile Arg Ser
145                 150                 155                 160

Glu Ser Val Glu Phe Met Pro Phe Tyr Leu Ser Leu Ser Thr Phe Leu
                165                 170                 175

Met Ser Ala Ser Phe Ala Leu Tyr Gly Leu Leu Leu Arg Asp Phe Phe
            180                 185                 190
```

```
Ile Tyr Phe Pro Asn Gly Leu Gly Leu Ile Leu Gly Ala Met Gln Leu
        195                 200                 205

Ala Leu Tyr Ala Tyr Tyr Ser Arg Lys Trp Arg Gly Gln Asp Ser Ser
210                 215                 220

Ala Pro Leu Leu Leu Ala
225                 230

<210> SEQ ID NO 21
<211> LENGTH: 224
<212> TYPE: PRT
<213> ORGANISM: Neocallimastix californiae

<400> SEQUENCE: 21

Met Asp Phe Gly Asn Leu Ser Ile Gly Ala Thr Val Ser Thr Ile Leu
1               5                   10                  15

Met Phe Leu Thr His Leu Lys Thr Pro Ile Gln Ile Lys Arg Asn Ile
                20                  25                  30

Asn Ser Ile Tyr Asn Ile Pro Phe Leu Pro His Val Met Thr Phe Phe
            35                  40                  45

Asn Cys Ala Leu Trp Glu Lys Tyr Gly Ile Leu Lys Gly Asp Pro Gly
50                  55                  60

Met Ile Ile Ala Asn Phe Thr Gly Ile Ile Ile Asn Thr His Val Ile
65                  70                  75                  80

Phe Val Tyr Tyr Lys Asn Ser Arg Asp Leu Arg Asn Lys Val Glu Lys
                85                  90                  95

Ser Phe Ser Ile Met Ile Ile Thr Leu Ile Cys Ile Leu Ser Tyr Val
            100                 105                 110

Lys Leu Asn Arg Gly Leu Lys Ser Tyr Thr Ile Leu Gly Phe Ile Ser
        115                 120                 125

Ser Ile Ser Thr Ile Val Met Phe Gly Phe Pro Ile Ser Thr Leu Lys
130                 135                 140

Lys Val Ile Thr Thr Lys Asn Asn Ser Ser Leu Ser Ile Lys Pro Ile
145                 150                 155                 160

Ile Ile Leu Leu Ile Ser Ser Ala Leu Trp Thr Leu Tyr Gly Tyr Val
                165                 170                 175

Ile Lys Asp Asn Phe Val Cys Ile Pro Asn Gly Leu Gly Cys Leu Leu
            180                 185                 190

Ala Val Val Gln Leu Leu Ile Tyr Lys Leu Tyr Ser Lys Arg Glu Tyr
        195                 200                 205

Ser Leu Pro Gln Asn Thr Ile Gln Met Thr Pro Phe His Met Lys Asn
210                 215                 220

<210> SEQ ID NO 22
<211> LENGTH: 218
<212> TYPE: PRT
<213> ORGANISM: Neocallimastix californiae

<400> SEQUENCE: 22

Met Asn Phe Glu Asn Leu Ile Ser Ile Gly Ala Thr Val Ser Thr Ile
1               5                   10                  15

Leu Met Phe Leu Thr His Leu Lys Thr Pro Ile Gln Ile Asn Arg Asn
                20                  25                  30

Ile Asn Ala Ile Tyr Asn Ile Pro Phe Phe Pro Leu Val Met Thr Phe
            35                  40                  45

Phe Asn Cys Ser Leu Trp Glu Lys Tyr Gly Ile Leu Lys Gly Asp Pro
50                  55                  60
```

Gly Met Ile Ile Val Asn Phe Thr Gly Ile Ile Thr Thr His Val
65                  70                  75                  80

Ile Phe Val Tyr Tyr Lys Asn Ser Arg Asp Leu Arg Lys Lys Val Glu
                85                  90                  95

Lys Ser Phe Thr Ile Met Ile Val Thr Leu Ile Cys Ile Glu Ala Tyr
                100                 105                 110

Val Lys Phe Asn Arg Gly Leu Lys Ser Tyr Thr Val Leu Gly Phe Leu
                115                 120                 125

Ser Ser Ile Ser Thr Ile Ile Met Phe Gly Ser Pro Leu Ser Thr Leu
                130                 135                 140

Lys Lys Val Ile Arg Thr Lys Asp Asn Ser Ser Leu Ser Ile Gln Leu
145                 150                 155                 160

Leu Met Ile Ser Leu Ile Ser Ser Gly Leu Trp Thr Leu Tyr Gly Phe
                165                 170                 175

Val Ile Lys Asp Asn Phe Val Ser Ile Pro Asn Gly Leu Gly Cys Val
                180                 185                 190

Leu Ala Ala Ile Gln Leu Leu Ile Tyr Lys Thr Tyr Ser Lys Lys Glu
                195                 200                 205

Tyr Thr Leu Pro Gln Asn Ser Ile Pro Leu
    210                 215

<210> SEQ ID NO 23
<211> LENGTH: 224
<212> TYPE: PRT
<213> ORGANISM: Anaeromyces robutus

<400> SEQUENCE: 23

Met Ser Thr Asp Asn Leu Val Ser Ile Gly Ala Thr Ile Ser Thr Ile
1               5                   10                  15

Leu Met Phe Leu Thr His Leu Lys Thr Pro Leu Glu Ile Asn Arg Asn
                20                  25                  30

Ile Asn Ala Ile Tyr Ile Ile Pro Phe Pro His Ile Met Thr Phe
                35                  40                  45

Phe Asn Cys Thr Leu Trp Glu Lys Tyr Gly Ile Leu Lys Gly Asp Leu
        50                  55                  60

Ala Met Ile Phe Val Asn Phe Thr Gly Ile Leu Ile Thr Thr Asn Val
65                  70                  75                  80

Ile Tyr Ile Tyr Tyr Lys Asn Ala Arg Asp Leu Lys Lys Lys Val Glu
                85                  90                  95

Lys Ser Phe Thr Ile Ala Ile Leu Gly Leu Ile Ile Leu Ser Tyr
                100                 105                 110

Val Lys Phe Asn Arg Gly Ser Thr Ser Tyr Thr Val Leu Gly Phe Leu
                115                 120                 125

Thr Asn Ile Ser Thr Ile Ile Thr Phe Gly Ser Pro Leu Ser Thr Leu
130                 135                 140

Lys Arg Val Val Gln Thr Lys Asp Asn Ser Ser Leu Ser Ile His Leu
145                 150                 155                 160

Ile Val Ile Ser Phe Val Ser Ser Phe Leu Trp Thr Leu Tyr Gly Tyr
                165                 170                 175

Ile Ile Asn Asp Lys Phe Val Thr Val Pro Asn Gly Leu Gly Cys Leu
                180                 185                 190

Leu Ser Ala Phe Gln Ile Ile Tyr Tyr Ile Tyr Ser Lys Asp Tyr
                195                 200                 205

Ser Leu Pro Gln Asn Thr Ile Gln Met Thr Pro Phe His Leu Lys Asn

<210> SEQ ID NO 24
<211> LENGTH: 224
<212> TYPE: PRT
<213> ORGANISM: Piromyces finnis

<400> SEQUENCE: 24

Met Asn Phe Asn Asn Leu Val Ser Ile Gly Ala Thr Ile Ser Thr Ile
1               5                   10                  15

Leu Leu Phe Ser Thr His Met Lys Thr Pro Ile Gln Ile Asn Arg Asn
            20                  25                  30

Ile Asn Ser Ile Tyr Asn Ile Ser Phe Leu Pro His Ile Met Thr Phe
        35                  40                  45

Phe Ser Cys Ser Leu Trp Glu Lys Tyr Gly Ile Leu Lys Gly Asp Leu
    50                  55                  60

Gly Ile Ile Phe Ser Asn Phe Ile Gly Ile Ile Thr Thr His Val
65                  70                  75                  80

Ile Phe Val Tyr Tyr Lys Asn Ser Arg Asp Leu Lys Pro Lys Val Glu
                85                  90                  95

Lys Ser Phe Thr Ile Ile Leu Ala Leu Ile Ser Ile Leu Thr Tyr
            100                 105                 110

Val Lys Leu Asn Arg Gly Ile Thr Ser Tyr Asn Val Leu Gly Phe Ile
        115                 120                 125

Cys Val Ile Ser Ser Leu Leu Met Leu Val Ser Pro Leu Lys Ile Leu
    130                 135                 140

Lys Glu Val Val Lys Thr Arg Glu Asn Ser His Leu Ser Ile Gln Phe
145                 150                 155                 160

Ile Leu Ile Ser Phe Ile Ser Ser Ser Leu Trp Thr Leu Tyr Gly Tyr
                165                 170                 175

Phe Ile Asn Asp Lys Phe Ile Ile Pro Asn Gly Leu Gly Cys Leu
            180                 185                 190

Leu Ala Ala Ile Gln Ala Leu Ile Tyr Lys Ile Tyr Ser Lys Glu Tyr
        195                 200                 205

Asn Leu Pro His Asn Thr Ile Gln Met Thr Pro Phe His Leu Lys Asn
    210                 215                 220

<210> SEQ ID NO 25
<211> LENGTH: 244
<212> TYPE: PRT
<213> ORGANISM: Anaeromyces robutus

<400> SEQUENCE: 25

Met Leu Glu Cys Lys Ser Ser Thr Cys Glu Phe Ile Ile Gln Thr Gly
1               5                   10                  15

Phe Pro Phe Val Gly Ile Phe Thr Ala Tyr Phe Ile Tyr Leu Ser Pro
            20                  25                  30

Leu Lys Asp Val Ile Pro Leu Tyr Lys Lys Met Gly Ser Arg Asp Val
        35                  40                  45

Cys Gln Ile Asn Pro Tyr Pro Ile Val Met Ile Phe Cys Asn Thr Leu
    50                  55                  60

Cys Gln Cys Phe Tyr Ala Tyr Val Ile His Asn His Trp Val Ile Trp
65                  70                  75                  80

His Asn Leu Gly Gly Thr Val Ala Gly Leu Phe Phe Val Val Ile Val
                85                  90                  95

Leu Tyr Ser Ser Asn Leu Lys Lys Lys Asp Phe Asn Leu Ala Thr Ile

```
                  100                 105                 110
Thr Leu Leu Leu Leu Thr Phe Ala Asn Leu Gly Cys Ala Ala Leu Ala
            115                 120                 125

Phe Ile Leu Phe His Asp Asp Tyr Pro Lys Ala Lys Asn Thr Ile Gly
            130                 135                 140

Ile Leu Asn Ile Val Ile Leu Phe Gly Val Tyr Val Ser Pro Leu Ala
145                 150                 155                 160

Thr Met Tyr Glu Val Ile Lys Thr Arg Asn Ser Ser Ile Asn Phe
            165                 170                 175

Ile Met Thr Ile Ala Met Phe Ile Asn Ser Ile Leu Trp Thr Gly Tyr
            180                 185                 190

Gly Phe Ile Ile Asn Asp Phe Tyr Ile Trp Phe Pro Asn Val Val Gly
            195                 200                 205

Ile Val Ser Thr Ile Ile Gln Phe Val Leu Leu Ile Val Phe Pro Ser
            210                 215                 220

Lys Lys Lys Asn Ala Asp Lys Lys Ile Glu Glu Asn Ile Asn Glu Lys
225                 230                 235                 240

Val Ile Asn Ile

<210> SEQ ID NO 26
<211> LENGTH: 220
<212> TYPE: PRT
<213> ORGANISM: Neocallimastix californiae

<400> SEQUENCE: 26

Met Asn Pro Ile Pro Ser Ile Met Val Phe Cys Asn Cys Leu Ser Gln
1               5                   10                  15

Thr Leu Tyr Ser Phe Thr Ile His Asn His Trp Asn Tyr Trp Pro Asn
            20                  25                  30

Phe Gly Gly Val Ile Leu Gly Leu Tyr Tyr Val Ala Ile Ile Val Ser
        35                  40                  45

Ala Lys Leu Lys Pro Arg Val Trp Asn Met Ser Thr Thr Val Leu Leu
    50                  55                  60

Gly Phe Thr Leu Leu Cys Leu Ile Gly Gly Ala Leu Ala Phe Ile Leu
65                  70                  75                  80

Phe Asp Asp Asn Tyr Glu Ala Ala Lys Asn Ser Met Gly Ile Ile Gly
                85                  90                  95

Ile Val Ile Leu Cys Gly Ile Tyr Gly Ser Pro Leu Thr Thr Met Tyr
            100                 105                 110

Glu Met Ile His Thr Arg Asn Ser Ser Ile Asn Phe Ile Met Thr
            115                 120                 125

Val Ala Leu Leu Ile Asn Gly Val Phe Trp Thr Ala Tyr Gly Val Phe
130                 135                 140

Ile Asn Asp Phe Phe Ile Trp Phe Pro Asn Ala Val Gly Thr Phe Ser
145                 150                 155                 160

Ala Val Ile Gln Phe Leu Leu Phe Leu Ile Phe Pro Arg Lys Ser Thr
            165                 170                 175

Thr Gly Thr Asp Val Asn Glu Ala Gln Ser Tyr Ser Ser Val Asn Lys
            180                 185                 190

Asp Asn Tyr Glu Thr Glu Thr Asp Val Ser Gly Ile Thr Leu Gln Pro
            195                 200                 205

Ser Glu Leu Ser Glu Lys Asp Ile Ser Asn Ile Val
210                 215                 220
```

```
<210> SEQ ID NO 27
<211> LENGTH: 210
<212> TYPE: PRT
<213> ORGANISM: Anaeromyces robutus

<400> SEQUENCE: 27
```

Met Ile Ile Cys Asn Cys Leu Cys Trp Asn Leu Tyr Ser Phe Val Ile
1               5                   10                  15

His Asn His Trp Thr Phe Trp Pro Asn Leu Gly Gly Ile Leu Leu Gly
            20                  25                  30

Glu Tyr Tyr Val Met Ile Leu Leu Ser Ser Lys Ile Thr Pro Lys Asp
        35                  40                  45

Phe Lys Met Ser Val Ile Thr Leu Leu Gly Phe Thr Phe Leu Asn Ile
    50                  55                  60

Ala Gly Gly Ala Leu Ser Phe Ile Phe Leu Lys Asp Asn Tyr Thr Ala
65                  70                  75                  80

Ala Lys Asn Cys Met Gly Ile Val Cys Ile Ile Val Leu Cys Ala Met
                85                  90                  95

Tyr Ala Ser Pro Leu Thr Thr Met Ala Glu Val Ile Arg Thr Lys Asn
            100                 105                 110

Ser Asp Ser Ile Asn Leu Leu Met Thr Ile Ala Ser Phe Ile Asn Gly
        115                 120                 125

Phe Leu Trp Leu Ile Tyr Gly Ile Phe Phe Gln Asp Phe Tyr Val Trp
    130                 135                 140

Phe Pro Asn Gly Leu Gly Val Val Ser Ala Leu Ile Gln Phe Ile Met
145                 150                 155                 160

Tyr Phe Ala Phe His Lys Asn Ser Lys Arg Asp Ser Gln Asp Leu Pro
                165                 170                 175

Ile Tyr Asp Asn Asn Ser Gly Glu Ala Ser Pro Asn Ser Glu Ile Pro
            180                 185                 190

Ser Ser Pro Asp Ser Asn Thr Pro Ile Lys Gly Asn Ser Thr Met Leu
        195                 200                 205

Tyr Ser
    210

```
<210> SEQ ID NO 28
<211> LENGTH: 248
<212> TYPE: PRT
<213> ORGANISM: Neocallimastix californiae

<400> SEQUENCE: 28
```

Met Glu Cys Asn Ser Arg Ala Cys Glu Ile Ile Thr Glu Thr Ile Phe
1               5                   10                  15

Pro Leu Cys Gly Ile Val Thr Ser Tyr Phe Ile Phe Ser Pro Phe
            20                  25                  30

Lys Glu Ile Gln Thr Leu Lys Asn Ser Asn Gly Pro Cys Asn Ile Asn
        35                  40                  45

Pro Ile Pro Ser Val Met Ile Cys Asn Cys Leu Cys Trp Ser Leu
    50                  55                  60

Tyr Ser Phe Val Ile His Asn His Trp Thr Phe Trp Pro Asn Leu Gly
65                  70                  75                  80

Gly Ile Leu Leu Gly Glu Tyr Tyr Thr Met Val Leu Leu Ser Ser Lys
                85                  90                  95

Leu Ser Pro Lys Gln Phe Lys Leu Ser Ala Ile Thr Leu Ile Gly Phe
            100                 105                 110

Thr Phe Leu Asn Ile Ala Gly Ala Ala Ala Ser Phe Ile Phe Leu Lys

```
            115                 120                 125
Asp Asn Tyr Glu Ala Ala Lys Asn Cys Met Gly Val Ile Thr Ile Ile
    130                 135                 140

Val Leu Cys Ala Met Tyr Val Ser Pro Leu Thr Ser Met Arg Glu Val
145                 150                 155                 160

Ile Met Thr Arg Asp Ser Ser Ser Leu Asn Pro Leu Leu Thr Ile Ala
                165                 170                 175

Ser Phe Ile Asn Gly Phe Trp Val Val Tyr Gly Phe Phe Phe Asn Asp
                180                 185                 190

Phe Tyr Val Trp Phe Pro Asn Gly Met Gly Val Val Ser Ala Ala Ile
            195                 200                 205

Gln Phe Ala Leu Phe Ile Ile Phe His Arg Ser Ser Arg Arg Asn Ser
    210                 215                 220

Gln Glu Leu Pro Ile Tyr Asp Gly Glu Ser Ser Pro Lys Ser Glu Leu
225                 230                 235                 240

Ser Ser Pro Thr Ser Val Ser Pro
                245
```

<210> SEQ ID NO 29
<211> LENGTH: 41
<212> TYPE: DNA
<213> ORGANISM: Artificial Sequence
<220> FEATURE:
<223> OTHER INFORMATION: Primer MFalt, SacI, Rev

<400> SEQUENCE: 29
catagagctc aattctctta ggattcgatt cacattcatc t         41

<210> SEQ ID NO 30
<211> LENGTH: 35
<212> TYPE: DNA
<213> ORGANISM: Artificial Sequence
<220> FEATURE:
<223> OTHER INFORMATION: Primer TEF1p, EcoRI, Fwd

<400> SEQUENCE: 30
catagaattc agatctgttt agcttgcctc gtccc         35

<210> SEQ ID NO 31
<211> LENGTH: 46
<212> TYPE: DNA
<213> ORGANISM: Artificial Sequence
<220> FEATURE:
<223> OTHER INFORMATION: Primer MFalt, SpeI, Fwd

<400> SEQUENCE: 31
cataactagt gaaaatgttt cagttgatac agctatgact ttacaa         46

<210> SEQ ID NO 32
<211> LENGTH: 46
<212> TYPE: DNA
<213> ORGANISM: Artificial Sequence
<220> FEATURE:
<223> OTHER INFORMATION: Primer NcSW1, SpeI, Rev

<400> SEQUENCE: 32
cataactagt gaaaatgttt cagttgatac agctatgact ttacaa         46

<210> SEQ ID NO 33
<211> LENGTH: 52
<212> TYPE: DNA
<213> ORGANISM: Artificial Sequence
<220> FEATURE:
<223> OTHER INFORMATION: Primer NcSW2, SpeI, Rev

<400> SEQUENCE: 33
cataactagt taataataac ttaagagttg aagacatggg tatctattac tg        52

<210> SEQ ID NO 34
<211> LENGTH: 51
<212> TYPE: DNA
<213> ORGANISM: Artificial Sequence
<220> FEATURE:
<223> OTHER INFORMATION: Primer NcSW3, SpeI, Rev

<400> SEQUENCE: 34
cataactagt attttcata tgaaatggtg tcatttgaat agtattttgt g         51

<210> SEQ ID NO 35
<211> LENGTH: 46
<212> TYPE: DNA
<213> ORGANISM: Artificial Sequence
<220> FEATURE:
<223> OTHER INFORMATION: Primer ArSW1, SpeI, Rev

<400> SEQUENCE: 35
cataactagt attttcaaa tgaaatggag tcatttgaat tgtatt              46

<210> SEQ ID NO 36
<211> LENGTH: 42
<212> TYPE: DNA
<213> ORGANISM: Artificial Sequence
<220> FEATURE:
<223> OTHER INFORMATION: Primer ArSW2, SpeI, Rev

<400> SEQUENCE: 36
cataactagt ccatggagaa tacaacatag ttgagttacc tt                  42

<210> SEQ ID NO 37
<211> LENGTH: 58
<212> TYPE: DNA
<213> ORGANISM: Artificial Sequence
<220> FEATURE:
<223> OTHER INFORMATION: Primer ArSW3, SpeI, Rev

<400> SEQUENCE: 37
cataactagt aatattaata accttttcat taatattttc ttcaattttc ttatctgc    58

<210> SEQ ID NO 38
<211> LENGTH: 52
<212> TYPE: DNA
<213> ORGANISM: Artificial Sequence
<220> FEATURE:
<223> OTHER INFORMATION: Primer PfSW1, SpeI, Rev

<400> SEQUENCE: 38
cataactagt attttttaaa tgaaatggag tcatttgaat agtattatgt gg        52

<210> SEQ ID NO 39
<211> LENGTH: 43
<212> TYPE: DNA
<213> ORGANISM: Artificial Sequence
<220> FEATURE:
<223> OTHER INFORMATION: Primer PfSW2, SpeI, Rev

<400> SEQUENCE: 39
cataactagt accatacaaa gtagtagaat tagcgttcaa tgg                 43

<210> SEQ ID NO 40
<211> LENGTH: 35
<212> TYPE: DNA
<213> ORGANISM: Artificial Sequence
<220> FEATURE:
<223> OTHER INFORMATION: Primer HXT7, EagI, Fwd

<400> SEQUENCE: 40
catacggccg atgtcacaag acgctgctat tgcag        35

<210> SEQ ID NO 41
<211> LENGTH: 40
<212> TYPE: DNA
<213> ORGANISM: Artificial Sequence
<220> FEATURE:
<223> OTHER INFORMATION: Primer HXT7, SpeI, Rev

<400> SEQUENCE: 41
cataactagt tttggtgctg aacattctct tgtacaatgg        40

<210> SEQ ID NO 42
<211> LENGTH: 27
<212> TYPE: DNA
<213> ORGANISM: Artificial Sequence
<220> FEATURE:
<223> OTHER INFORMATION: Primer pRS, USER, Fwd

<400> SEQUENCE: 42
acacagacaa gaugaaacaa ttcggca        27

<210> SEQ ID NO 43
<211> LENGTH: 28
<212> TYPE: DNA
<213> ORGANISM: Artificial Sequence
<220> FEATURE:
<223> OTHER INFORMATION: Primer pRS, USER, Rev

<400> SEQUENCE: 43
atcttgtctg tguagaagac cacacacg        28

<210> SEQ ID NO 44
<211> LENGTH: 39
<212> TYPE: DNA
<213> ORGANISM: Artificial Sequence
<220> FEATURE:
<223> OTHER INFORMATION: Primer N1/N2, USER, Rev

<400> SEQUENCE: 44
acctctattg aacaaaauaa aagacaaagc accaccaca        39

<210> SEQ ID NO 45
<211> LENGTH: 36
<212> TYPE: DNA
<213> ORGANISM: Artificial Sequence
<220> FEATURE:
<223> OTHER INFORMATION: Primer N1/N3, USER, Rev

<400> SEQUENCE: 45
atctttgaac aaaauaaaag acaaagcacc accaca        36

<210> SEQ ID NO 46
<211> LENGTH: 38
<212> TYPE: DNA
<213> ORGANISM: Artificial Sequence
<220> FEATURE:
<223> OTHER INFORMATION: Primer N1/N4, USER, Rev

```
<400> SEQUENCE: 46
attgtcatcg aacaaaauaa aagacaaagc accaccac                              38

<210> SEQ ID NO 47
<211> LENGTH: 38
<212> TYPE: DNA
<213> ORGANISM: Artificial Sequence
<220> FEATURE:
<223> OTHER INFORMATION: Primer N1/A1, USER, Rev

<400> SEQUENCE: 47
agaaccattg ttcutgaaca aaataaaaga caaagcac                              38

<210> SEQ ID NO 48
<211> LENGTH: 35
<212> TYPE: DNA
<213> ORGANISM: Artificial Sequence
<220> FEATURE:
<223> OTHER INFORMATION: Primer N1/A2, USER, Rev

<400> SEQUENCE: 48
tctttgaaca aaauaaaaga caaagcacca ccaca                                 35

<210> SEQ ID NO 49
<211> LENGTH: 36
<212> TYPE: DNA
<213> ORGANISM: Artificial Sequence
<220> FEATURE:
<223> OTHER INFORMATION: Primer N1/A3, USER, Rev

<400> SEQUENCE: 49
atcatggaac aaaauaaaag acaaagcacc accaca                                36

<210> SEQ ID NO 50
<211> LENGTH: 38
<212> TYPE: DNA
<213> ORGANISM: Artificial Sequence
<220> FEATURE:
<223> OTHER INFORMATION: Primer N1/P1, USER, Rev

<400> SEQUENCE: 50
acctctattg aacaaauaa aagacaaagc accaccac                               38

<210> SEQ ID NO 51
<211> LENGTH: 36
<212> TYPE: DNA
<213> ORGANISM: Artificial Sequence
<220> FEATURE:
<223> OTHER INFORMATION: Primer N1/P2, USER, Rev

<400> SEQUENCE: 51
atctttgaac aaaauaaaag acaaagcacc accaca                                36

<210> SEQ ID NO 52
<211> LENGTH: 53
<212> TYPE: DNA
<213> ORGANISM: Artificial Sequence
<220> FEATURE:
<223> OTHER INFORMATION: Primer N1/N2, USER, Fwd

<400> SEQUENCE: 52
attttgttca atagaggutt gaaatcttat actattttag gttttatttc ttc             53

<210> SEQ ID NO 53
```

-continued

```
<211> LENGTH: 43
<212> TYPE: DNA
<213> ORGANISM: Artificial Sequence
<220> FEATURE:
<223> OTHER INFORMATION: Primer N1/N3, USER, Fwd

<400> SEQUENCE: 53
attttgttca aagauaacta tgaagctgca aaaaactgta tgg          43

<210> SEQ ID NO 54
<211> LENGTH: 43
<212> TYPE: DNA
<213> ORGANISM: Artificial Sequence
<220> FEATURE:
<223> OTHER INFORMATION: Primer N1/N4, USER, Fwd

<400> SEQUENCE: 54
attttgttcg atgacaauta tgaagctgct aaaaactcta tgg          43

<210> SEQ ID NO 55
<211> LENGTH: 43
<212> TYPE: DNA
<213> ORGANISM: Artificial Sequence
<220> FEATURE:
<223> OTHER INFORMATION: Primer N1/A1, USER, Fwd

<400> SEQUENCE: 55
agaacaatgg ttcuacttct tatactgttt tgggttttat tac          43

<210> SEQ ID NO 56
<211> LENGTH: 45
<212> TYPE: DNA
<213> ORGANISM: Artificial Sequence
<220> FEATURE:
<223> OTHER INFORMATION: Primer N1/A2, USER, Fwd

<400> SEQUENCE: 56
attttgttca agauaatta tacagctgct aaaaattgta tgggt         45

<210> SEQ ID NO 57
<211> LENGTH: 43
<212> TYPE: DNA
<213> ORGANISM: Artificial Sequence
<220> FEATURE:
<223> OTHER INFORMATION: Primer N1/A3, USER, Fwd

<400> SEQUENCE: 57
attttgttcc atgaugacta cccaaaagct aaaaacacta ttg          43

<210> SEQ ID NO 58
<211> LENGTH: 50
<212> TYPE: DNA
<213> ORGANISM: Artificial Sequence
<220> FEATURE:
<223> OTHER INFORMATION: Primer N1/P1, USER, Fwd

<400> SEQUENCE: 58
attttgttca atagagguat tacttcttat aatgttttgg gttttatttg    50

<210> SEQ ID NO 59
<211> LENGTH: 45
<212> TYPE: DNA
<213> ORGANISM: Artificial Sequence
<220> FEATURE:
<223> OTHER INFORMATION: Primer N1/P2, USER, Fwd

<400> SEQUENCE: 59
```
attttgttca aagauaatta tgatgctgct aaaaactgta tgggt    45

<210> SEQ ID NO 60
<211> LENGTH: 50
<212> TYPE: DNA
<213> ORGANISM: Artificial Sequence
<220> FEATURE:
<223> OTHER INFORMATION: Primer NcSW3, SacII, Rev

<400> SEQUENCE: 60
cataccgcgg tttttcatat gaatggtgt catttgaata gtattttgtg    50

<210> SEQ ID NO 61
<211> LENGTH: 58
<212> TYPE: DNA
<213> ORGANISM: Artificial Sequence
<220> FEATURE:
<223> OTHER INFORMATION: Primer ArSW3, SacII, Rev

<400> SEQUENCE: 61
cataccgcgg aatattaata accttttcat taatattttc ttcaattttc ttatctgc    58

<210> SEQ ID NO 62
<211> LENGTH: 43
<212> TYPE: DNA
<213> ORGANISM: Artificial Sequence
<220> FEATURE:
<223> OTHER INFORMATION: Primer PfSW2, SacII, Rev

<400> SEQUENCE: 62
cataccgcgg accatacaaa gtagtagaat tagcgttcaa tgg    43

<210> SEQ ID NO 63
<211> LENGTH: 44
<212> TYPE: DNA
<213> ORGANISM: Artificial Sequence
<220> FEATURE:
<223> OTHER INFORMATION: Primer N1/P2:Ct, USER, Fwd

<400> SEQUENCE: 63 attttatgg aaaauaaaaa acaacaagaa ttgcaacaaa gcag    44

<210> SEQ ID NO 64
<211> LENGTH: 39
<212> TYPE: DNA
<213> ORGANISM: Artificial Sequence
<220> FEATURE:
<223> OTHER INFORMATION: Primer N1/P2:Ct, USER, Rev

<400> SEQUENCE: 64
attttccata aaaautctgg taagaattct caagaattg    39

<210> SEQ ID NO 65
<211> LENGTH: 41
<212> TYPE: DNA
<213> ORGANISM: Artificial Sequence
<220> FEATURE:
<223> OTHER INFORMATION: Primer NcSW1:Tr, USER, Fwd

<400> SEQUENCE: 65
aagaaactag ttaauaataa cttaagagtt gaagacatgg g    41

<210> SEQ ID NO 66
<211> LENGTH: 46
<212> TYPE: DNA

```
<213> ORGANISM: Artificial Sequence
<220> FEATURE:
<223> OTHER INFORMATION: Primer NcSW1:Tr, USER, Rev

<400> SEQUENCE: 66
attaactagt ttctutttta ggataaataa aaacaacaa gaattg                    46

<210> SEQ ID NO 67
<211> LENGTH: 45
<212> TYPE: DNA
<213> ORGANISM: Artificial Sequence
<220> FEATURE:
<223> OTHER INFORMATION: Primer N1/P2:TM4-7, USER, Fwd

<400> SEQUENCE: 67
attttgtttt cttcuaacat gaagccaaaa gattttaaat ggact                    45

<210> SEQ ID NO 68
<211> LENGTH: 30
<212> TYPE: DNA
<213> ORGANISM: Artificial Sequence
<220> FEATURE:
<223> OTHER INFORMATION: Primer N1/P2:TM3-7, USER, Fwd

<400> SEQUENCE: 68
acaatcattg gacuttctgg ccaaacttgg                                     30

<210> SEQ ID NO 69
<211> LENGTH: 45
<212> TYPE: DNA
<213> ORGANISM: Artificial Sequence
<220> FEATURE:
<223> OTHER INFORMATION: Primer N1/P2:TM2-7, USER, Fwd

<400> SEQUENCE: 69
accatttaag gaautacaaa atttgaaaaa atctaatggt caatg                    45

<210> SEQ ID NO 70
<211> LENGTH: 34
<212> TYPE: DNA
<213> ORGANISM: Artificial Sequence
<220> FEATURE:
<223> OTHER INFORMATION: Primer N1/P2:TM1-7, USER, Fwd

<400> SEQUENCE: 70
aattattact gaaacugttt ttccattgtg tggt                                34

<210> SEQ ID NO 71
<211> LENGTH: 47
<212> TYPE: DNA
<213> ORGANISM: Artificial Sequence
<220> FEATURE:
<223> OTHER INFORMATION: Primer N1/P2:TM4-7, USER, Rev

<400> SEQUENCE: 71
agaagaaaac aaaaucataa tataatattg acccaaaata ataccac                  47

<210> SEQ ID NO 72
<211> LENGTH: 43
<212> TYPE: DNA
<213> ORGANISM: Artificial Sequence
<220> FEATURE:
<223> OTHER INFORMATION: Primer N1/P2:TM3-7, USER, Rev

<400> SEQUENCE: 72
agtccaatga ttgugaataa caaaagaata caagtcttgg cac                      43
```

```
<210> SEQ ID NO 73
<211> LENGTH: 46
<212> TYPE: DNA
<213> ORGANISM: Artificial Sequence
<220> FEATURE:
<223> OTHER INFORMATION: Primer N1/P2:TM2-7, USER, Rev

<400> SEQUENCE: 73
attccttaaa tggugataaa aagataaaat aagctgtaaa acaacc          46

<210> SEQ ID NO 74
<211> LENGTH: 35
<212> TYPE: DNA
<213> ORGANISM: Artificial Sequence
<220> FEATURE:
<223> OTHER INFORMATION: Primer N1/P2:TM1-7, USER, Rev

<400> SEQUENCE: 74
agtttcagta ataatutcac aagcttgaga agtgc          35
```